US011371093B2

(12) United States Patent
Lehto et al.

(10) Patent No.: US 11,371,093 B2
(45) Date of Patent: *Jun. 28, 2022

(54) BIOLOGICAL ANALYSIS SYSTEMS, DEVICES, AND METHODS

(71) Applicant: LIFE TECHNOLOGIES CORPORATION, Carlsbad, CA (US)

(72) Inventors: Dennis Lehto, Santa Clara, CA (US); Steven J. Boege, San Mateo, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/246,990

(22) Filed: Jan. 14, 2019

(65) Prior Publication Data

US 2019/0390270 A1    Dec. 26, 2019

Related U.S. Application Data

(63) Continuation of application No. 14/997,956, filed on Jan. 18, 2016, now Pat. No. 10,184,149, which is a
(Continued)

(51) Int. Cl.
*C12Q 1/6874* (2018.01)
*B01L 3/00* (2006.01)
(Continued)

(52) U.S. Cl.
CPC ............ *C12Q 1/6874* (2013.01); *B01L 3/502* (2013.01); *B01L 3/50851* (2013.01); *B01L 7/00* (2013.01);
(Continued)

(58) Field of Classification Search
CPC ................................ G03B 27/42; B01L 9/527
See application file for complete search history.

(56) References Cited

U.S. PATENT DOCUMENTS 2,942,520 A   6/1960  Rose et al.
3,029,695 A   4/1962  Wolf et al.
(Continued)

FOREIGN PATENT DOCUMENTS

DE    3505334 A1    10/1985
DE    3619596 A1    12/1987
(Continued)

OTHER PUBLICATIONS

Brochure entitled "Introducing The Polonator G.007," from Danaher Motion-Dover.
(Continued)

*Primary Examiner* — Kathryn Wright

(57) ABSTRACT

A device for performing biological sample reactions may include a plurality of flow cells configured to be mounted to a common microscope translation stage, wherein each flow cell is configured to receive at least one sample holder containing biological sample. Each flow cell also may be configured to be selectively placed in an open position for positioning the at least one sample holder into the flow cell and a closed position for reacting biological sample contained in the at least one sample holder. The plurality of flow cells may be configured to be selectively placed in the open position and the closed position independently of each other.

19 Claims, 26 Drawing Sheets

Related U.S. Application Data continuation of application No. 12/575,004, filed on Oct. 7, 2009, now abandoned, which is a continuation of application No. 12/244,701, filed on Oct. 2, 2008, now abandoned.

(60) Provisional application No. 60/977,858, filed on Oct. 5, 2007.

(51) Int. Cl.

| | | |
|---|---|---|
| *B01L 7/00* | (2006.01) | |
| *G01N 21/05* | (2006.01) | |
| *G03B 27/42* | (2006.01) | |
| *B01L 9/00* | (2006.01) | |
| *G01N 15/14* | (2006.01) | |
| *G01N 21/03* | (2006.01) | |

(52) U.S. Cl.
CPC ............... *B01L 7/52* (2013.01); *G01N 21/05* (2013.01); *B01J 2219/005* (2013.01); *B01J 2219/00286* (2013.01); *B01J 2219/00306* (2013.01); *B01J 2219/00533* (2013.01); *B01J 2219/00596* (2013.01); *B01J 2219/00648* (2013.01); *B01L 9/527* (2013.01); *B01L 2200/10* (2013.01); *B01L 2300/043* (2013.01); *B01L 2300/0822* (2013.01); *B01L 2300/0877* (2013.01); *B01L 2300/1805* (2013.01); *B01L 2300/1811* (2013.01); *B01L 2300/1894* (2013.01); *G01N 15/1459* (2013.01); *G01N 15/1463* (2013.01); *G01N 15/1484* (2013.01); *G01N 21/0332* (2013.01); *G01N 2021/0346* (2013.01); *G01N 2021/058* (2013.01); *G01N 2201/02* (2013.01); *G03B 27/42* (2013.01)

(56) References Cited

U.S. PATENT DOCUMENTS

| | | |
|---|---|---|
| 3,031,924 A | 5/1962 | Lamal et al. |
| 3,141,547 A | 7/1964 | Newby et al. |
| 4,059,405 A | 11/1977 | Sodickson et al. |
| 4,159,875 A | 7/1979 | Hauser et al. |
| 4,349,275 A | 9/1982 | Ayotte et al. |
| 4,436,385 A | 3/1984 | Fischer et al. |
| 4,641,930 A | 2/1987 | Podvin et al. |
| 5,125,544 A | 6/1992 | Millner et al. |
| 5,281,516 A | 1/1994 | Stapleton et al. |
| 5,346,672 A | 9/1994 | Stapleton et al. |
| 5,393,494 A | 2/1995 | Greenfield et al. |
| 5,417,576 A | 5/1995 | Hill |
| 5,430,542 A | 7/1995 | Shepherd |
| 5,592,289 A | 1/1997 | Norris |
| 5,656,501 A | 8/1997 | Yedgar et al. |
| 5,677,133 A | 10/1997 | Oberhardt |
| 6,251,601 B1 | 6/2001 | Bao et al. |
| 6,315,958 B1 | 11/2001 | Singh-Gasson et al. |
| 6,316,610 B2 | 11/2001 | Lee et al. |
| 6,406,848 B1 | 6/2002 | Bridgham et al. |
| 6,646,243 B2 | 11/2003 | Pirrung et al. |
| 6,654,505 B2 | 11/2003 | Bridgham et al. |
| 6,673,620 B1 | 1/2004 | Loeffler et al. |
| 6,677,131 B2 | 1/2004 | Yuen |
| 6,806,052 B2 | 10/2004 | Bridgham et al. |
| 6,806,954 B2 | 10/2004 | Sandstrom |
| 6,844,929 B2 | 1/2005 | Glenn et al. |
| 6,864,097 B1 | 3/2005 | Schembri et al. |
| 7,070,740 B1 | 7/2006 | Matson et al. |
| 7,072,105 B2 | 7/2006 | Delaage |
| 7,081,954 B2 | 7/2006 | Sandstrom |
| 7,083,975 B2 | 8/2006 | Green et al. |
| 7,125,523 B2 | 10/2006 | Sillman |
| 2002/0131167 A1 | 9/2002 | Nguyen et al. |
| 2003/0017081 A1 | 1/2003 | Trulson et al. |
| 2003/0087455 A1 | 5/2003 | Eggers et al. |
| 2003/0096423 A1 | 5/2003 | Ryan et al. |
| 2004/0022677 A1 | 2/2004 | Wohlstadter |
| 2004/0051854 A1 | 3/2004 | Tanaka et al. |
| 2004/0086428 A1 | 5/2004 | Loeffler et al. |
| 2004/0091393 A1 | 5/2004 | Richardson |
| 2004/0101950 A1 | 5/2004 | Yuen |
| 2004/0114227 A1 | 6/2004 | Henderson et al. |
| 2005/0186598 A1 | 8/2005 | Schembri et al. |
| 2005/0196857 A1 | 9/2005 | Lee |
| 2005/0239195 A1 | 10/2005 | Oram et al. |
| 2005/0270642 A1 | 12/2005 | Mclellan et al. |
| 2006/0012784 A1 | 1/2006 | Ulmer |
| 2006/0088839 A1 | 4/2006 | Matsui et al. |
| 2006/0141507 A1 | 6/2006 | Kronick et al. |
| 2006/0257993 A1 | 11/2006 | Mcdevitt et al. |
| 2007/0009389 A1 | 1/2007 | Seppo et al. |
| 2007/0183943 A1 | 8/2007 | Golovkina et al. |
| 2008/0038163 A1 | 2/2008 | Boege et al. |
| 2009/0021728 A1* | 1/2009 | Heinz ................ B01F 11/0045 356/244 |
| 2009/0139311 A1 | 6/2009 | Lehto et al. |
| 2010/0035358 A1 | 2/2010 | Lehto et al. |

FOREIGN PATENT DOCUMENTS

| | | |
|---|---|---|
| JP | S5844412 A | 3/1983 |
| WO | WO-1998005330 | 2/1998 |
| WO | WO-2002072264 | 9/2002 |
| WO | WO-2006084132 A2 | 8/2006 |
| WO | WO-2006127852 A2 | 11/2006 |

OTHER PUBLICATIONS

PCT/US2008/078817, Search Report and Written Opinion, dated Feb. 5, 2009, 15 pgs.

* cited by examiner

BIOLOGICAL ANALYSIS SYSTEMS, DEVICES, AND METHODS

CROSS REFERENCE TO RELATED APPLICATIONS

This application is a continuation of U.S. application Ser. No. 14/997,956 filed Jan. 18, 2016, which is a continuation of U.S. application Ser. No. 12/575,004 filed Oct. 7, 2009 (abandoned), which is a continuation of U.S. application Ser. No. 12/244,701 filed Oct. 2, 2008 (abandoned), that claims a priority benefit under 35 U.S.C. § 119(e) from U.S. Provisional Application No. 60/977,858 filed Oct. 5, 2007. The entire contents of the aforementioned applications are incorporated by referenced herein.

TECHNICAL FIELD

The present teachings pertain generally to devices, systems, and methods for performing biological and/or biochemical reactions and/or analyses. More particularly, the present teachings are directed to various instruments useful in performing large scale parallel reactions on solid phase supports, such as, for example, performing sequencing by synthesis on beaded microarrays.

INTRODUCTION

The section headings used herein are for organizational purposes only and are not to be construed as limiting the subject matter described in any way.

Increasing efficiency and throughput are significant considerations in the development of tools and techniques for performing various aspects of biological and/or biochemical analysis. In the field of genomic sequencing, for example, various approaches have evolved in an attempt to obtain faster and less costly techniques that may be applied to perform sequencing for research applications and/or on an individualized basis. One approach to such sequencing, often referred to as sequencing-by-synthesis, uses microarrays comprising a plurality of small (e.g., from 1 micron to several hundred microns) analysis sites arranged on a surface of a support. Depending on the particular technique used, one or more single nucleic acid strands of interest (e.g., template nucleic acids strands) are attached to the analysis site. Bases are added either by polymerase to a complementary primer sequence to the template or by recognition of ligase as a match, and the sequence of the template strand is revealed. Typically some sort of optical signal, such as, for example, fluorescence, is detected by a microscope to determine the sequence in these techniques. The analysis sites of the microarrays may be in the form of small solid elements (e.g., beads) on each of which numerous identical oligonucleotides may be synthesized, with the solid elements being in turn placed on a support (e.g., substrate surface). Alternatively, the analysis sites may be sites directly on the substrate surface itself.

To perform sequencing, the microarrays of template nucleic acid strands to be synthesized may be loaded into a flow cell chamber mounted on a microscope stage and a mixture of sample, reagents and/or buffers may be introduced into the chamber to react with the microarrays. Massively parallel sequencing of the same or differing templates may occur using the microarray format due to the ability to place large numbers (e.g., millions) of template strands on a substrate, which may be in the form of a microscope slide, for example. Reactions occurring between the microarray templates and the loaded sample, reagents, and/or buffers within the flow cell may be analyzed using conventional fluorescence detection and microscopy techniques with which those having skill in the art are familiar.

In some configurations, flow cells may include a reaction chamber in which a sample holder, such as, for example, a microarrayed microscope slide or similar substrate with nucleic acid templates bound thereto, is configured to be seated and held in position. The reaction chamber may be defined between a sample holder (e.g., a substrate, such as, for example, a microscope slide, holding a sample) and a heater block configured to transfer heat to the chamber from various temperature control and heat exchange mechanisms (e.g., Peltier devices, cooling components, heat sinks, and/or feedback controllers, etc.) external to the chamber. A body on which the block is supported may be configured to move relative to a microscope stage and/or other frame to place the flow cell in a position for performing reactions in the reaction chamber and imaging the reaction chamber. One or more sealing members, such as, for example, O-rings, gaskets, or the like, may be provided, for example, on the surface of the block that faces the reaction chamber and may be configured to surround at least a portion of the sample holder to provide sealing of the portion of the sample holder within the chamber and where the reactions occur. Such gaskets may be configured to engage an outer region of a surface of a microarray substrate to define the outer perimeter of the area of the substrate at which reactions may take place. In such configurations, the reaction chamber (e.g., the chamber into which substances are introduced to the flow cell) is defined between the heater block and the substrate, with the sealing mechanism on the heater block forming a seal to seal the chamber. Various inlet and outlet ports may be provided on the flow cell to permit the flow of desired substances (e.g., samples, reagents, lysis chemicals, and/or buffers, etc.) into and out of the reaction chamber and into reactive contact with the microarray and the templates thereon.

Additionally, the flow cell may include one or more optically transparent regions such that the sample holder, and in particular the reactions occurring between the sample held by the sample holder and the substances introduced into the flow cell reaction chamber, may be detected and observed via mechanisms located external to the flow cell (e.g., various microscope and optical fluorescent detectors). In some configurations, the surface of a microarray substrate that faces the chamber and where the reactions take place faces in a direction opposite to where the optics used for analysis and detection are positioned.

Flow cells may be mounted on a microscope stage that can translate in three dimensions, and may be oriented either in a horizontal or vertical position, with the microscope optics, light sources, and/or imaging devices being positioned appropriately relative thereto.

Conventional flow cell systems used for sequencing-by-synthesis and/or other biological analysis applications may permit a reduction in the amount of reagents, sample, and/or buffers needed for reactions and/or analysis and relatively high throughput for sequencing Nonetheless, it may be desirable to improve such systems to help achieve more efficient biological analysis (e.g., sequencing).

For example, it may be desirable to modify conventional flow cell systems to increase throughput of sample analysis. It also may be desirable to modify conventional flow cell systems to improve accuracy of imaging of the reaction chamber. It may further be desirable to improve thermal features of conventional flow cell systems. In addition, it may be desirable to improve on the efficiency with which microarrayed substrates or other sample holders may be transported and mounted to flow cell systems for analysis (e.g., sequencing).

SUMMARY OF EXEMPLARY EMBODIMENTS

The present invention may satisfy one or more of the above-mentioned desirable features. Other features and/or advantages may become apparent from the description which follows.

According to various embodiments, the present teachings include a device for performing biological sample reactions may include a plurality of flow cells configured to be mounted to a common microscope translation stage, wherein each flow cell is configured to receive at least one sample holder containing biological sample. Each flow cell also may be configured to be selectively placed in an open position for positioning the at least one sample holder into the flow cell and a closed position for reacting biological sample contained in the at least one sample holder. The plurality of flow cells may be configured to be selectively placed in the open position and the closed position independently of each other.

In various exemplary embodiments, the present teachings include a carrier for retaining a substrate holding at least one biological sample, the carrier comprising a frame defining a recess configured to receive a substrate holding at least one biological sample on a surface thereof. The carrier may further include a plurality of retaining fingers configured to move into and out of engagement with the substrate to retain the substrate in the recess and at least two extension portions extending from the frame in a direction away from the recess, each of the extension portions comprising a surface with which a respective clamping mechanism can engage to clamp the frame in position in a reaction chamber.

In accordance with yet other exemplary embodiments, the present teachings may include a flow cell configured to hold the carrier described above and the flow cell may include a heater block configured to mate with the frame of the carrier, wherein a reaction chamber is formed between the heater block and a substrate in the recess of the carrier. The flow cell may include a plurality of clamping mechanisms configured to engage with the plurality of extension portions to hold the carrier on the heater block.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive.

The accompanying drawings, which are incorporated in and constitute a part of this specification, illustrate some exemplary embodiments and, together with the description, serve to explain the principles.

DESCRIPTION OF EXEMPLARY EMBODIMENTS

Reference will now be made in detail to various exemplary embodiments of the present teachings, examples of which are illustrated in the accompanying drawings. Wherever possible, the same reference numbers will be used throughout the drawings to refer to the same or like parts.

Flow cells in accordance with exemplary embodiments of the present teachings may have a variety of forms and configurations. In general, a flow cell may include any structure configured to define a reaction chamber to receive a biological sample for analysis and various flow control structures and mechanisms to permit sample, reagents, buffers and/or other substances from a source external to the flow cell into the reaction chamber to react with the biological sample (e.g., template nucleic acids when performing sequencing) contained in the reaction chamber. In various exemplary configurations, flow cells may also include or be associated with various thermal components configured to heat and/or cool the reaction chamber. Also, various exemplary flow cell configurations may have optically transparent portions that permit imaging and/or other detection of the reaction chamber, for example, to perform analysis of various reactions that may be performed in the reaction chamber. Those having skill in the art are familiar with various flow cell configurations. For further details regarding flow cell arrangements, reference may be made to WO 2006/084132, U.S. Pat. Nos. 6,406,848 and 6,654,505, and PCT Publication No. WO 98/05330, which are incorporated by reference herein.

Figure 1:
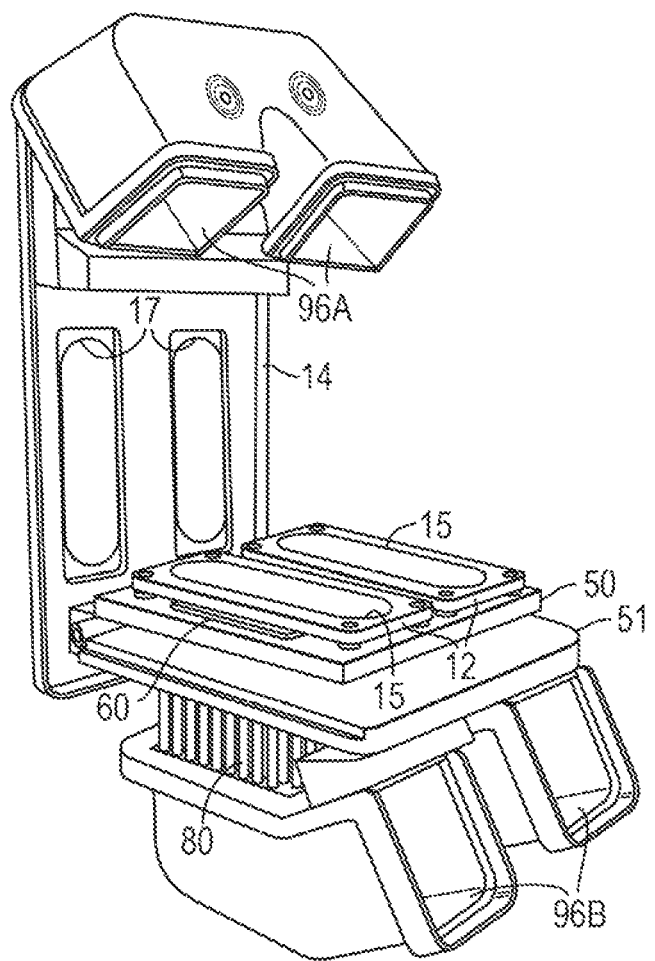
FIG. 1 is a perspective view of an exemplary embodiment of a dual flow cell system in accordance with the present teachings.

To increase throughput during biological reactions and analysis, such as, for example, performing sequencing-by-synthesis, a dual flow cell system has been described that includes two segregated reaction chambers such that processing (e.g., reactions) may occur separately within each formed chamber. For example, each reaction chamber may receive a different sample and/or reagents for processing. Exemplary embodiments of such a dual flow cell system are described in U.S. application Ser. No. 11/757,286, filed on Jun. 1, 2007 and entitled "SYSTEMS AND METHODS FOR COOLING IN BIOLOGICAL ANALYSIS INSTRUMENTS", which is incorporated by reference in its entirety herein. With reference to FIG. 1, the dual flow cell configuration described in U.S. application Ser. No. 11/757,286, includes two separate sample blocks (also referred to as heater blocks) 12 each provided with a sealing mechanism 15 configured to engage with a surface, such as a microscope slide surface forming a microarray (not shown in FIG. 1), to create the segregated reaction chambers into which various substances (e.g., samples, buffers, reagents, lysis solutions, etc.) could be introduced to react with the microarrayed samples (e.g., template nucleic acids) within each formed chamber. The elements 15 may be any of a variety of mechanisms useful for forming a seal, such as, for example, gaskets, O-rings, and/or other sealing mechanisms with which those having ordinary skill in the art would be familiar.

The sample blocks 12 may be made of a material that has a relatively high thermal conductivity. In various exemplary embodiments, the sample blocks 12 may be stainless steel, lapped on one side and passivated. Other suitable materials for the sample blocks 12 include, but are not limited to, for example, silver, aluminum, copper, and/or various alloys and/or other metals. The blocks 12 are mounted on frame 50 attached to a pivotable support plate 51 which generally forms a door with which to open and close the flow cells (FIG. 1 illustrating the open position). The pivotable support plate 51 is configured to move into engagement with a frame (e.g., cover) 14 to close the flow cells and to apply pressure against the substrates (e.g., by clamping them between the sealing mechanisms 15 and the surface of the cover 14 on which the substrates are mounted, thereby forming the reaction chambers when the support plate 51 is closed against the cover). In an exemplary embodiment, a thumb screw positioned between the ducts 96B (not shown in FIG. 1) is configured to engage with screw threading on the cover 14 to keep the support plate 51 in a closed position.

The cover 14 may define two optically transparent regions 17, such as, for example, openings. In various exemplary embodiments, the openings may be covered with a transparent material, such as, for example a glass or plastic material or other suitable transparent composition. The optically transparent regions 17 are configured to substantially align with each of the blocks 12 when the instrument is in the closed position to perform optical detection and/or imaging of the flow cell reaction chambers and the substrates therein. Various optical detection and imaging systems may be used (components of which are not illustrated) and may be positioned external to the cover 14 to detect and gather, for example, in real-time, images of reactions and samples in the reaction chambers through the openings 17. For details regarding an exemplary detection and imaging system that may be used in conjunction with the biological instruments in FIG. 1 and described herein, reference is made to WO 2006/081432, incorporated by reference in its entirety herein. In an exemplary embodiment, retaining clips or other securement mechanisms (not shown) may be provided to mount a microarray substrate or other sample holder to cover 14 proximate (e.g., in alignment with) the regions 17. For example, suitable securement mechanisms may comprise small plastic tabs (not shown) configured to slide sideways to engage the top of the substrate to prevent the substrate from tipping over until the support plate 51 is closed.

The dual flow cell arrangement of FIG. 1 may be configured to be mounted to a common microscope translation stage (not shown) capable of translation in two dimensions, with the objective lens of the microscope being focused in a direction normal to the plane defined by those two dimensions. In general, the microscope stage is configured to move in a plane parallel to a plane of a substrate placed on the microscope stage for analysis. Although the flow cell may be mounted to a translation stage that is in a horizontal position (e.g., the larger planar surface area of the stage is configured to be parallel to the ground), in various exemplary embodiments, the dual flow cell embodiment is configured to be mounted to a microscope translation stage positioned in a vertical direction (e.g., such that the larger planar work surface area of the stage is substantially perpendicular to the ground). In such a position, the cover 14 (or a plate positioned substantially parallel and adjacent to the cover 14) may be mounted to the surface of the vertically positioned translation stage. Thus, when the support 51 is closed, the reaction chambers and any sample holders therein (e.g., microarrayed substrates) are in a substantially vertical position during processing. Such a vertical orientation may have advantages during biological reaction and/or analysis (e.g., including detection and/or imaging). For example, by orienting the reaction chambers vertically, gas (e.g., air) bubbles that may be formed in the reaction chamber may flow to the top of the chamber and exit an output port positioned toward the chamber top, permitting gravimetric bubble displacement. For further details regarding advantages of substantially vertically oriented flow cell instruments, reference is made to WO 2006/084132, incorporated by reference herein. Those having skill in the art are familiar with the mounting of flow cells to a vertically positioned microscope translation stage. It should be understood, however, that the flow cells may have orientations other than vertical during reaction and analysis. Those skilled in the art would understand various modifications could be made to provide a flow cell in another orientation without departing from the scope of the present teachings.

Various thermal components (some of which are not shown in FIG. 1), such as, for example, a Peltier device 60, a heat sink 80, and ducts 96A and 96B also are mounted to provide thermal cycling of each of the flow cells of FIG. 1. Other components also may be used to provide temperature control and exchange heat with the reaction chambers of the dual flow cell arrangement of FIG. 1 and are described in more detail in U.S. application Ser. No. 11/757,286, incorporated by reference herein. It should be noted that for simplicity the various ports and flow structures used to introduce substances to and remove substances from the flow cell chambers to react with the microarrayed substrates therein are not shown in FIG. 1. Those ordinarily skilled in the art are familiar with various flow control mechanisms, including but not limited to, for example, ports, piping, conduits, valves, and/or other flow control devices (not shown), that may be used to flow various samples, buffers, reagents and/or other substances into and out of the reaction chambers. Those having skill in the art would understand how such flow control mechanisms may be configured and disposed to flow substances into and out of the reaction chambers.

A dual flow cell configuration such as that shown in the exemplary embodiment of FIG. 1 permits differing reactions and/or analysis to be taking place at the same time within the different reaction chambers. A dual flow cell arrangement such as that illustrated in the exemplary embodiment FIG. 1 also may permit one flow cell to be imaged while other process steps such as, for example, extension, ligation, and/or cleavage, are being performed in another flow cell. This may maximize utilization of the optical system while increasing throughput. Further, a dual flow cell arrangement may permit the processing and/or analysis of differing samples to occur.

In the exemplary configuration of FIG. 1, the dual flow cell chambers are accessible via a common door. In other words, when support 51 is released from cover 14 and placed into the open position of FIG. 1, both flow cell chambers also are in an open position. It may be desirable in some circumstances, however, to permit independent access to each of the flow cell reaction chambers of a dual flow cell assembly. By permitting independent access to each flow cell, various loading and/or unloading steps may take place in one reaction chamber while the other reaction chamber is undergoing processing and/or imaging steps. Permitting the flow cell reaction chambers to be accessed (e.g, opened and closed) independently of each other also may permit each microarray substrate to be loaded into and closed within the flow cell reaction chamber more quickly, thereby hindering drying out of the substrates during loading. Further, in cases where a reaction and/or processing occurring in one flow cell chamber needs to be terminated for whatever reason and sample removed therefrom, the reaction and/or processing in the other flow cell chamber may continue uninterrupted. Moreover, by allowing the flow cells to be independently accessed and providing them with independent thermal components, reagent inlet and outlet ports, and thermal isolation from each other, processing of two differing samples at differing temperature cycles may occur without the temperature variation affecting the focus of the optics and detection equipment. More specifically, changes in temperature of various portions of the flow cell (e.g., metal portions) may cause those portions to expand and/or buckle, which may disturb the focus of the microscope optics. Utilizing independent flow cells that are thermally isolated from each other may permit the flow cells to be maintained at a substantially constant temperature for each processing cycle and thereby minimize the risk of adversely affecting the focusing of the microscope.

Figure 2A:
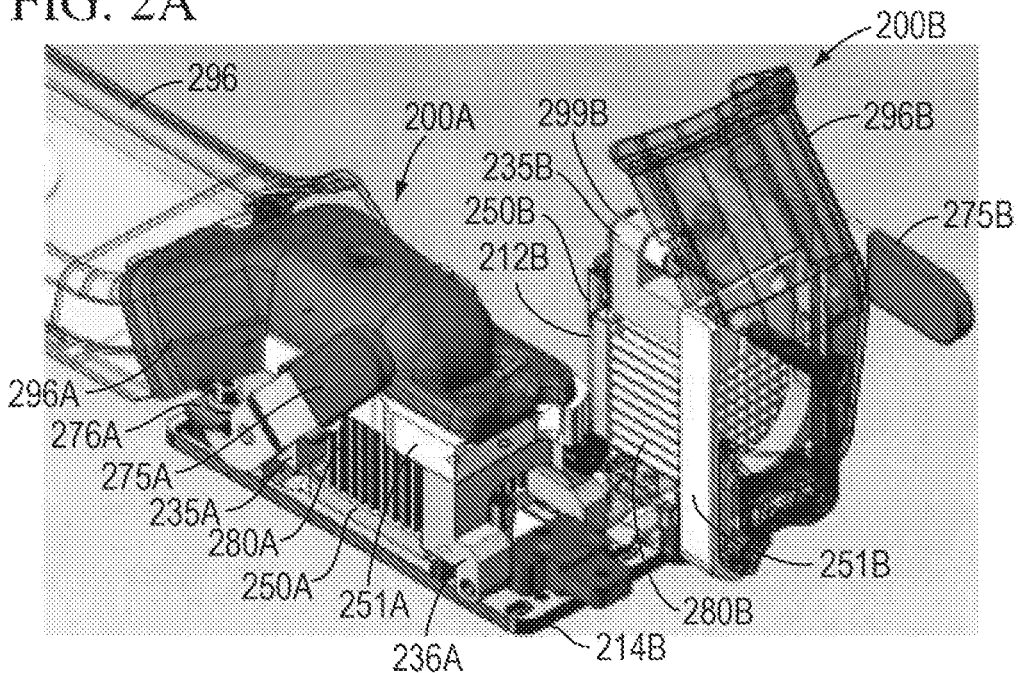
FIGS. 2A and 2B are perspective views of another exemplary embodiment of a dual flow cell system in accordance with the present teachings.
Figure 2B:
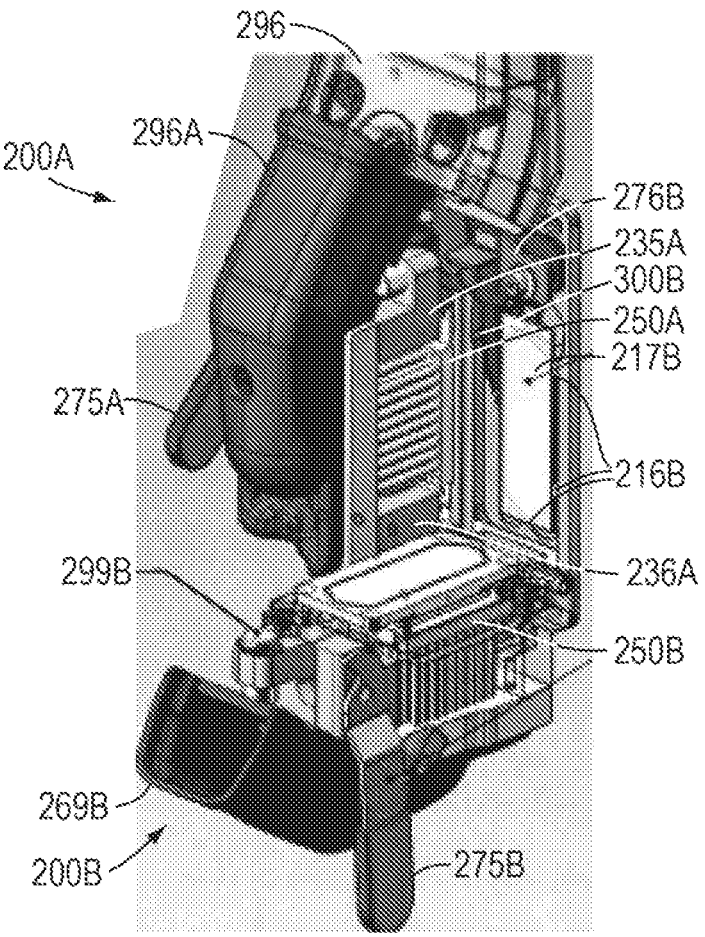

FIGS. 2A and 2B illustrate one exemplary embodiment that permits independent access to each flow cell chamber of a dual flow cell instrument. FIGS. 2A and 2B illustrate different views of an independently accessible dual flow cell instrument with one flow cell chamber 200A in a closed position and one flow cell chamber 200B in an open position. In the exemplary embodiment of FIGS. 2A and 2B, the cooling system used to cool the flow cells 200A and 200B incorporates a remote fan and duct assembly similar to that described in U.S. patent application Ser. No. 11/757,286, incorporated by reference herein. Those having ordinary skill in the art would understand, however, that other cooling systems, such as, for example, recirculating chilling fluid-based systems, may be used in combination with the dual door configuration of FIGS. 2A and 2B. Modifications to replace the cooling components, other thermal components, and/or flow control mechanisms for introducing various reagents, sample, buffers, etc. to each flow cell chamber 200A and 200B independently would be obvious to those having ordinary skilled in the art and are not described in detail herein.

In the exemplary embodiment of FIGS. 2A and 2B, each sample block (with only 212B being visible in the illustrations) is ultimately supported on a substantially U-shaped frame comprising frame elements 235, 251, and 236 (labeled with references A and B accordingly in FIGS. 2A and 2B). Via elements 236A and 236B, which are pivotably engaged via a hinged arrangement relative to a common frame (e.g., cover) 214, the support frame and therefore the blocks 212A and 212B and any thermal or other components respectively mounted thereto, may be moved into an open position away from cover 214, as shown by flow cell 200B, and into a closed position and into engagement with cover 214, as shown by flow cell 200A. As was described above with reference to the exemplary embodiment of FIG. 1, when in the closed position, a closure mechanism, an exemplary embodiment of which is described in more detail below, between the frame elements 235, 251, and 236 and the cover 214 is configured to provide a clamping force between the block (only block 212B is shown) and the respective slides 210 mounted relative to the cover 214 such that an isolated reaction chamber is formed between the sample block, a gasket on each block (only gasket 215B is shown) and the slide 210 with which it engages. Each support frame (formed respectively by elements 235A, 236A, and 251A, and elements 235B, 236B, and 251B) may support the blocks and the various thermal and other support components associated with the blocks, and may be configured to move relative to the cover 214 mounting plate to open and close the flow cells 200A and 200B.

As mentioned above, each of the flow cell chambers 200A and 200B also may have independently mounted thermal elements, such as, for example, a Peltier device (shown for flow cell 200B as 260B) disposed underneath the sample block 212B, a heat sink 280A, 280B, and ducts 296A and 296B configured to circulate air to the respective heat sinks 250A and 250B with heat sink pins 280A and 280B. The ducts 296A and 296B and heat sinks 280A and 280B are separately mounted to the respective flow cells 200A and 200B so that each can be moved between the open position (as shown by flow cell 200B) and closed position (as shown by flow cell 200A).

A sensor (e.g. 299B shown in FIG. 2B) may be provided on each flow cell 200A and 200B so that when the flow cells 200A or 200B are in the open position, the fan and Peltier device are turned off to prevent the air blown from duct 296 from drying out a substrate mounted in the open flow cell and to prevent overheating of the heater block. In an exemplary embodiment, the sensor (e.g., 299B) may be an air flow sensor with a standard mechanical limit switch and a lever mounted to the frame 235B. The lever tip strikes part of the duct 296 when the flow cells 200A or 200B are put in the closed position and another feature on the lever actuates the switch upon opening the flow cells 200A or 200B.

The cover 214 may be provided with recessed regions, within which each sample block is configured to be received when the respective flow cell is in a closed position.

As shown in FIGS. 2A and 2B, each flow cell 200A and 200B is provided with a closure mechanism, which in various exemplary embodiments may be lever locks 275A and 275B. The lever locks can be pivotably mounted to the frame elements 235A and 235B. As shown in FIG. 2A, the levers 275A and 275B are provided with a hook-type mechanism on one end thereof configured to respectively engage with a lip on protruding flanges 276A and 276B provided on the cover 214 to secure the flow cells 200A and 200B in a closed position. The engagement between the lever 275A and the flange 276A is shown in FIG. 2A. To release the lever lock and open the flow cell chambers 200A and 200B, a handle is provided on each lever lock 275A and 275B on an end substantially opposite to the locking end. The handle portion of the lever 275A may be pushed upward toward the duct 296 in FIG. 2A to release the engagement between the lever lock 275A and the flange 276A, thereby allowing the frame elements and various components mounted thereto to pivot downwardly away from the cover 214 to open the flow cell 200A. The lever locks 275A and 275B are held in place with the flanges 276A and 276B by a combination of friction and gravity—gravity due to the need to lift the handle portions of the lever locks 275A and 275B up to open them and friction between the lever locks 275A and 275B and flanges 276A and 276B. In various exemplary embodiments, the engagement between the lever locks 275A and 275B and flanges 276A and 276B may be selected so as to apply a set force to compress the gaskets on the heater blocks.

The lever locks 275A and 275B are configured to facilitate opening and closing of the flow cells 200A and 200B by offering a relatively simple mechanical mechanism that is easy to access and relatively quickly latch and unlatch. Further, by positioning the lever locks 275A and 275B such that their engagement with the flanges 276A and 276B is viewable by a user of the flow cells 200A and 200B, it is readily apparent whether they are in a locked, engaged position or an unlocked, disengaged position with the flanges 276A and 276B. Those having skill in the art would recognize, however, that securing mechanisms other than lever locks 275A and 275B and mating flanges 276A and 276B may be employed that offer similar features such as, for example, ease of accessibility, apparent indication of whether or not the securing mechanism is in a locked or unlocked position, etc.

Since in the exemplary embodiments of FIGS. 2A and 2B, the sample substrate 210 (the substrate in flow cell 200B is not shown in FIGS. 2A and 2B) is configured to be mounted vertically relative to each of the optically transparent regions (217B being shown) of each of the flow cells 200A and 200B, the flow cells 200A and 200B also may include a retaining mechanism 300B for retaining the substrate 210B (e.g., microscope slide) in an appropriate orientation and position. As shown in FIG. 2B, the substrate 210 is configured to be positioned in a recessed region of the cover 214 and the retaining mechanism 300B acts on the substrate 210B to provide a clamping force on the substrate 210B between the retaining mechanism 300B and protrusions 216B provided around the perimeter of the recessed region in which the substrate 210B is disposed. The retaining mechanism 300B thus serves to push the substrate 210B downwardly and toward the right in FIG. 2B, with the protrusions 216B being disposed to engage the right side and bottom edges of the substrate 210B, as depicted in FIG. 2B. As will be realized from the description of FIGS. 3 and 4 which follows, a similar retaining mechanism is used to push the substrate in the flow cell 200A down and to the left.

Figure 3:
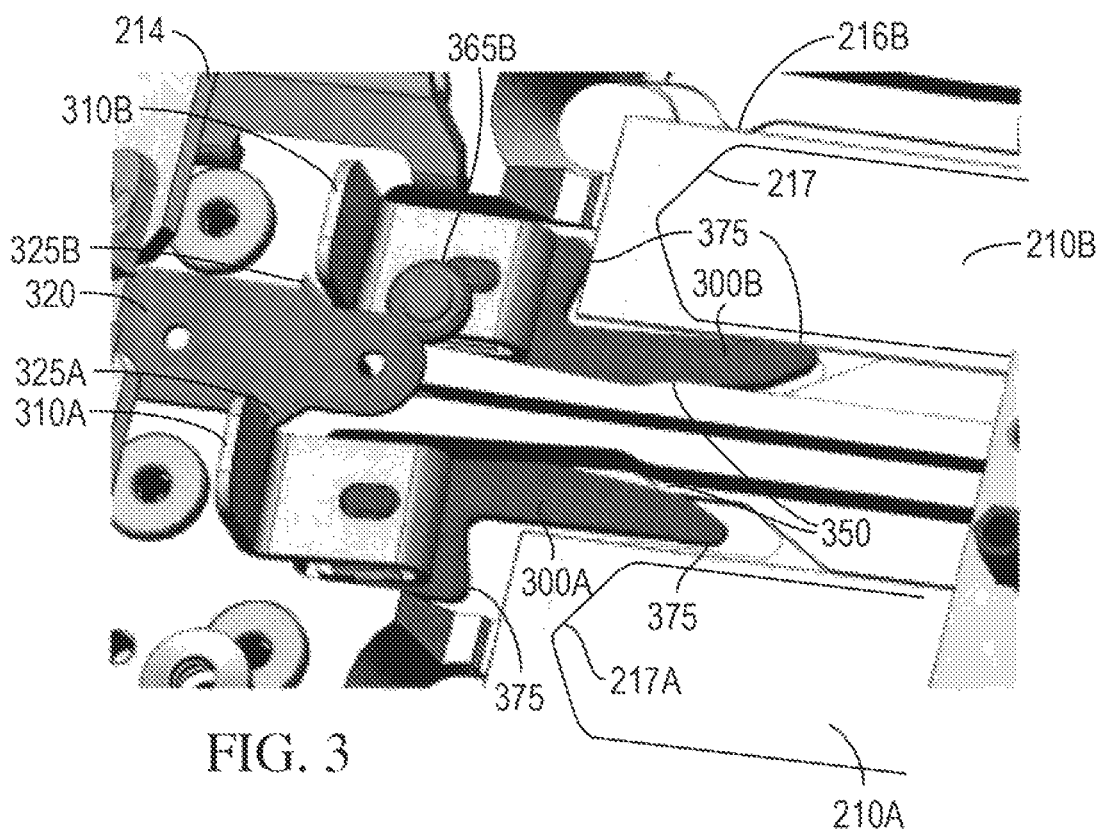
FIGS. 3 and 4 are partial plan views of an exemplary embodiment of retaining clips for holding a sample substrate within a flow cell chamber in accordance with the present teachings.

Referring now to FIG. 3, a partial close-up view of each of the cover 214 with substrates 210A and 210B mounted thereto illustrates an exemplary embodiment of retaining mechanisms 300A and 300B that may be used to clamp substrates 210A and 210B, which in various exemplary embodiments may be microscope slides with a microarray of template nucleic acids thereon, to cover 214 and in respective alignment with the optically transparent regions 217A and 217B (shown in outline in FIG. 3)

The retaining mechanisms 300A and 300B are configured to provide a force acting on the substrates 210A and 210B that push the substrates 210A and 210B toward the lower left and lower right corners, respectively, of the recessed regions provided in the cover 214. More specifically, the retaining mechanisms 300A and 300B may be biased to exert a force on the substrates 210A and 210B to push the substrates 210A and 210B into engagement with protrusions (e.g., protrusions 216B shown in FIGS. 2B, 3 and 4) so as to clamp the substrates 210A and 210B between the respective retaining mechanisms 300A and 300B and the protrusions. Those having skill in the art would understand that, although not shown in the view of FIGS. 2B, 3, and 4, the flow cell 200A may have protrusions similar in configuration and position to protrusions 216B shown in FIGS. 2B, 3, and 4. However, the protrusions of flow cell 200A are positioned on the left side and bottom edges of the recessed region housing substrate 210A; the retaining mechanism 300A thus pushing the substrate 210A downward and toward the left of the recessed region to clamp the substrate 210A into position.

Figure 4:
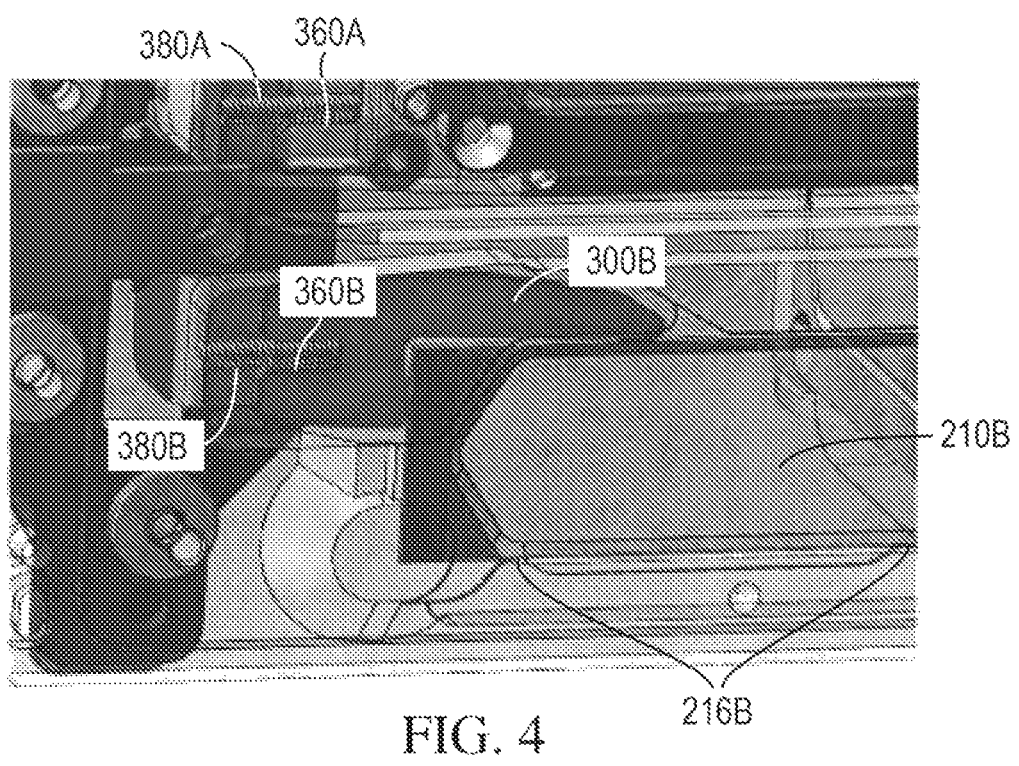

As mentioned above, the retaining mechanisms 300A and 300B are biased in the direction toward the substrates 210A and 210B in FIG. 3 (e.g., toward the right in the orientation of the drawing of FIG. 3 and downward in the orientation of the drawing in FIG. 2B). In various exemplary embodiments, as depicted in FIG. 4 which illustrates a partial view taken from underneath the view of FIG. 3, an upper portion of the retaining mechanisms 300A and 300B may be provided with a grooved region 360A and 360B configured to respectively retain a coiled spring 380A and 380B. One end of the springs 380A and 380B engage with the retaining mechanisms 300A and 300B, respectively, while the opposite ends are attached the cover 214. On their upper surfaces, each of the retaining mechanisms 300A and 300B may be provided with a flanged member 310A and 310B that projects upwardly from the retaining mechanisms 300A and 300B. The flange members 310A and 310B may provide a convenient surface to facilitate grasping of the retaining mechanisms 300A and 300B to pull the retaining mechanisms 300A and 300B against the force of the springs 380A and 380B and out of engagement with the substrates 210A and 210B.

To keep the retaining mechanisms 300A and 300B in a disengaged position, a catch element 320 may be provided on the cover 214 between the retaining mechanisms 300A and 300B. The catch element 320 may have ramped catches 325A and 325B on opposite sides thereof. The ramped catches 325A and 325B may be configured and positioned such that exerting a force on the flanged members 310A and 310B against the bias force of the springs 380A and 380B permits the flanged members 310A and 310B to move up the ramped surfaces of the catches 325A and 325B and past the catches 325A and 325B. The flanged members 310A and 310B may then be released such that they engage with the catches 325A and 325B, as shown by the position of flanged member 310A and catch 325A in FIG. 3, to prevent the retaining mechanisms 300A and 300B in a position out of engagement with the substrates 210A and 210B.

Applying a force on the upper and right side surfaces, and upper and left side surfaces, respectively, of the substrates 210A and 201B facilitates pushing the substrate 210A downward and to the left and the substrate 210B downward and to the right. Thus, the retaining mechanisms 300A and 300B have a substantially inverted L-shaped configuration with regions 375 on the base and long leg of the L that act as pressure points on the substrates 210A and 210B. As shown in the clamped position of the retaining mechanism 300B in FIG. 3, the regions 375 engage with the upper and left side surfaces of the substrate 300B to exert force (e.g., pressure) on those surfaces and push the substrate 300B down and to the right into clamped engagement with the protrusions 316B. Since the springs 380A and 380B provide a force acting substantially along a lengthwise direction of the substrates 300A and 300B (e.g., downward in the orientation of FIG. 2B and to the right in the orientation of FIG. 3), the recessed region that houses the retaining mechanisms 300A and 300B may be provided with a cammed surface 350 to provide a force on the retaining mechanisms 300A and 300B that pushes the long leg of the retaining mechanisms 300A and 300B into engagement with the right side edge and left side edge, respectively, of the substrates 210A and 210B.

To maintain the retaining mechanisms 300A and 300B sliding substantially in a plane parallel to the large surface area of the substrates 210A and 210B shown in FIG. 3, a grooved button 365B may be pressed between the catch element 320 and the retaining elements 300A and 300B. The grooved button corresponding to the retaining element 300A is hidden in the view of FIG. 3.

In various exemplary embodiments, the retaining mechanisms 300A and 300B may be made of, for example, stainless steel. However, those having skill in the art would recognize other suitable materials from which the retaining mechanisms could be made without departing from the scope of the present teachings.

In some cases, it may be awkward for a user to mount the substrate vertically within a flow cell. Moreover, when initially mounting the substrate in a vertical position, substance (e.g., liquid) on the substrate may run off the substrate and onto other components (e.g., the microscope stage) due to the open position of the flow cell during initial loading of the substrate. In addition, once mounted vertically, the side of the substrate that faces the microscope stage is not accessible and thus any contamination or drips may not be wiped off, which can affect detection and analysis. It may be desirable, therefore, to provide a dual door flow cell arrangement in which the substrate may be mounted horizontally by a user (e.g., with the larger surface area surface of the substrate substantially parallel to the ground) and from that mounted position, moved to a substantially vertical orientation (e.g., with the larger surface area of the substrate substantially parallel to the ground) upon closing the flow cell chamber to commence reactions therein. An issue that may arise in designing such a flow cell arrangement is how to ensure that the substrate is positioned appropriately within the flow cell reaction chamber such that correct focusing of the optics and detection mechanism occurs. In other words, it is important to ensure that the distance between the large surface area of the substrate and the various optics and detection elements is maintained relatively precisely for each reaction run of the flow cell in order to achieve accurate analyses and detection.

Various exemplary embodiments of dual flow cells that are independently accessible and that permit a user to mount a substrate for analysis in a horizontal position initially will now be described.

With reference to FIGS. 5-10, an exemplary embodiment of a dual flow cell arrangement wherein the flow cells are configured to completely detach from the microscope stage is depicted. Those having skill in the art would understand that the detachable flow cell arrangement described with reference to FIGS. 5-10 also could be implemented, using obvious design modifications, in a single flow cell arrangement or an arrangement wherein there are more than two flow cells on a common translation stage. The arrangement of FIGS. 5-10 permits a user to mount the slide horizontally, for example, at a workstation remote from the microscope stage, and inspect and clean the side of the substrate facing the user after the substrate has been mounted and before the flow cell is attached to the microscope stage.

Figure 5A:
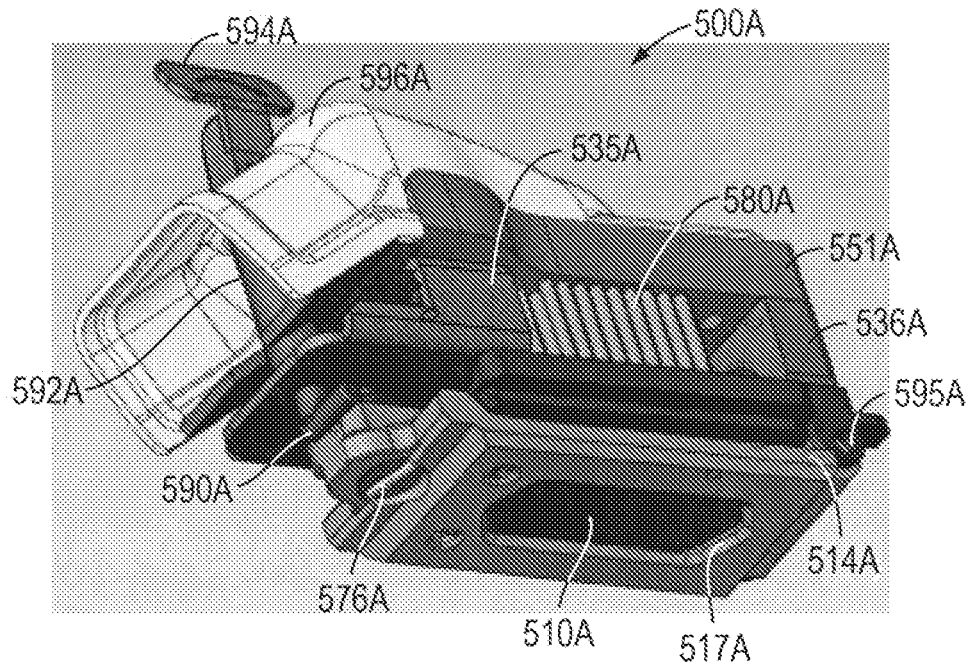
FIG. 5A is a perspective view of an exemplary embodiment of a detachable flow cell in a closed position accordance with the present teachings.
Figure 5B:
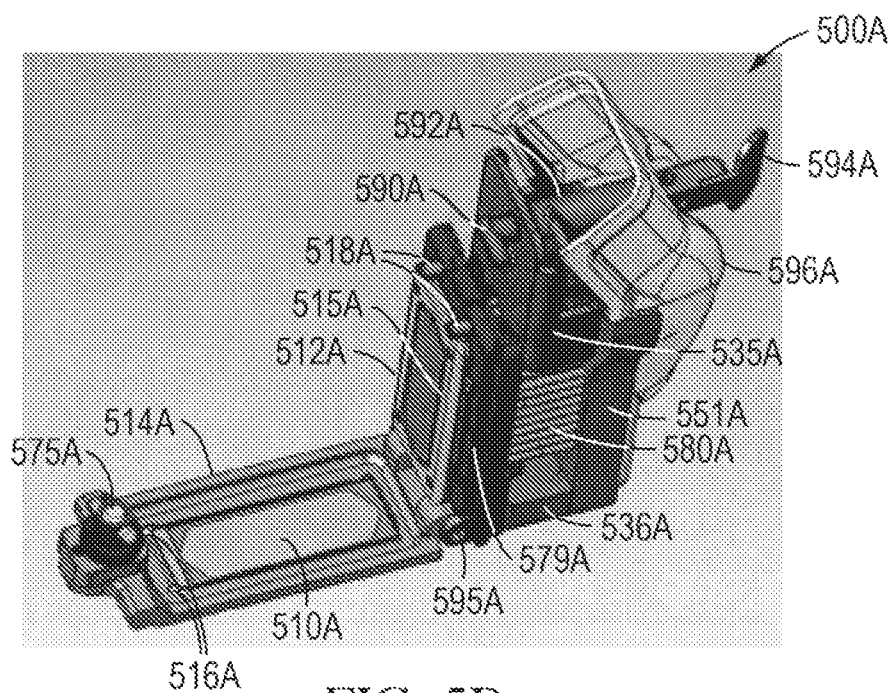
FIG. 5B is a perspective view of the flow cell of FIG. 5A in an open position.

FIGS. 5A and 5B show a detachable flow cell (labeled 500A) in a closed and open position, respectively. The flow cell 500A may have a configuration similar to the flow cells 200A and 200B described above with the exception of the various modifications discussed below. In a manner similar to the flow cells 200A and 200B, the flow cell 500A may have a heater block 512A with a sealing mechanism 515A thereon that ultimately is supported on support frame elements 535A, 536A, and 551A, forming a substantially U-shaped support frame. Also, similar to the flow cells 200A and 200B, the support frame element 536A may be attached via a hinge 595A to a cover 514A provided with an optically transparent region 517A. In the exemplary embodiment of FIGS. 5A and 5B, the transparent region 517A may be an opening over which a substrate for processing may be placed, as explained in more detail below. However, in the exemplary embodiment of FIGS. 5A and 5B, the cover 514A is separate from the microscope stage and each flow cell (e.g., 500A and 500B shown in FIG. 6) has its own cover 514A or 514B, rather than a common cover frame as in cover 214 of FIG. 2. The cover 514A may have a recessed region configured to receive the substrate 510A, which because of the detachable configuration of the flow cell, may be mounted by a user in a horizontal position as shown in FIG. 5B. Small holes 516A, the function of which is explained in more detail below, are provided in the cover proximate the corners of the substrate 510A when the substrate 510A is seated in the cover 514A. The holes 516A may receive pins 518A on a frame 579A when the cover 514A is placed in the closed position of FIG. 5A.

To close the flow cell 500A, the support frame elements 535A, 536A, and 551A, with the sample block 512A, thermal components (e.g., heat sink 580A), and a duct 596A for circulating cooling air to the flow cell 500A, may be pivoted around the hinge 595A such that the sealing mechanism 515A comes into contact with the substrate 510A arranged within the recess of the cover 514A. A rotatable closure mechanism 575A may be provided on the cover 514A that engages with a mating feature on frame 535A (as best shown in FIG. 5A) to lock the cover 514A in the closed position. The rotatable closure mechanism 575A may be actuated by turning a shaft with a rotating head 576A accessible from an exterior of the cover 514A. A more detailed explanation of how the closure mechanism 575A is actuated is provided below with reference to the description of FIGS. 11-13. Once in the closed position, the entire flow cell 500A is ready to be mounted to a frame on a microscope stage, an exemplary embodiment of which is described in further detail below with reference to FIGS. 6-10.

Referring now to FIGS. 6-9, individual detachable flow cells 500A and 500B are designed to be removably secured to a frame 519 that is configured to be attached (e.g., permanently attached) to a microscope stage (not shown) mounted in a vertical orientation. Flow cell 500B has the same configuration as flow cell 500A described above, and like parts are designated by a B after the reference numerals. As shown in the exemplary embodiments of FIGS. 6 and 7, the frame 519 also is attached at a top end thereof via a plate 521 to main duct 596 that is configured to receive air from a remotely positioned fan (not shown) and mate with the ducts 596A and 596B associated with each flow cell 500A and 500B to provide cooling air to each flow cell 500A and 500B, as has been described above.

Figure 6:
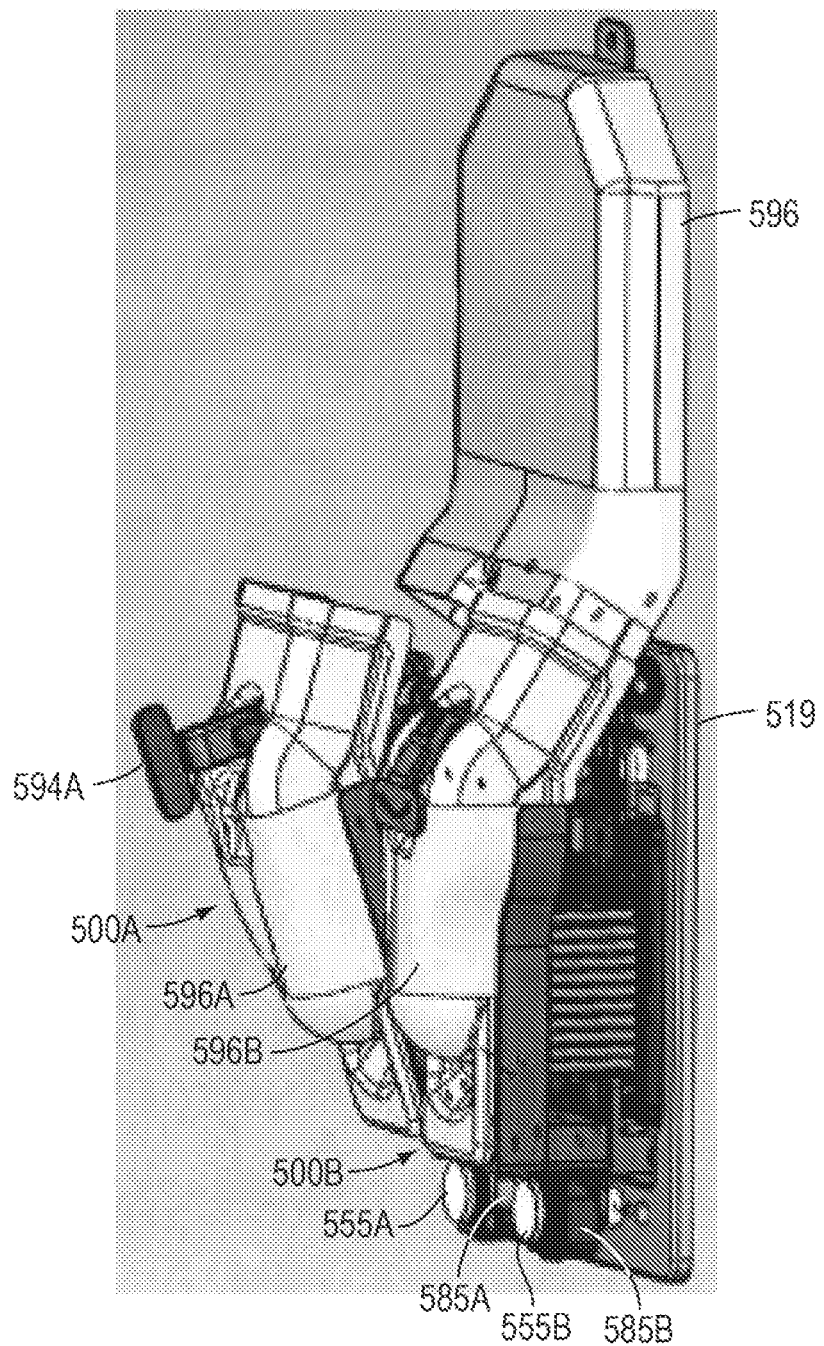
FIG. 6 is a perspective view of an exemplary embodiment of a dual detachable flow cell system with one flow cell fully inserted in position relative to a microscope stage and one flow cell partially inserted in position relative to the microscope stage.
Figure 7:
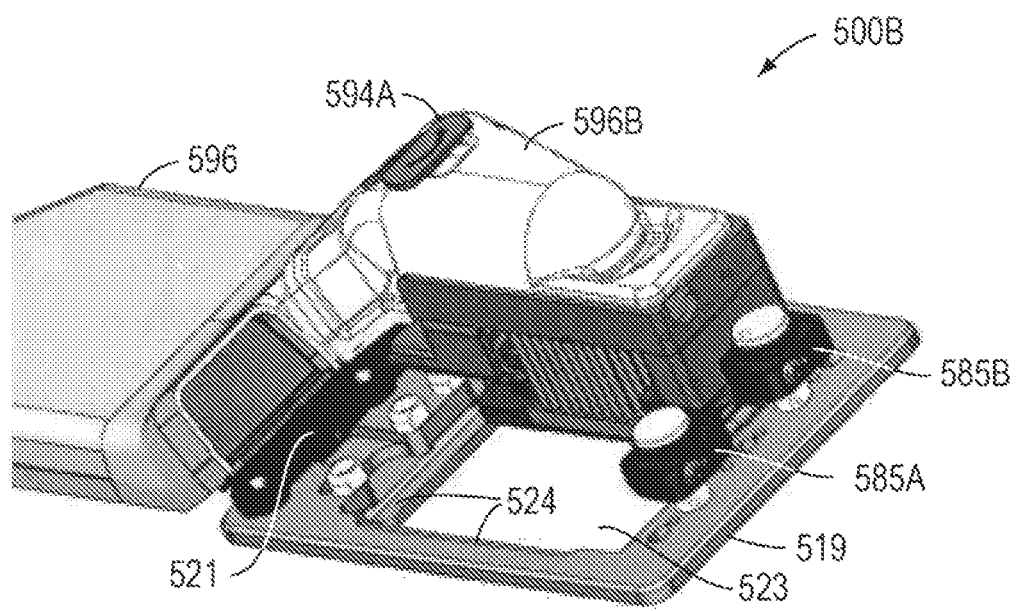
FIG. 7 is a perspective view of the exemplary embodiment of FIG. 6 showing one of the detachable flow cells removed from the microscope stage.

In FIG. 6, flow cell 500B is shown in its fully inserted and locked position in frame 519, while flow cell 500A is shown partially inserted. FIG. 7 shows a view of the frame 519 with flow cell 500A removed entirely and flow cell 500B fully inserted and locked in position relative to the frame 519. The frame 519 may define a relatively large opening 523 configured to receive both the flow cells 500A and 500B. The outer perimeter of the opening 523 may have a stepped profile 524 configured to support the support plate on which the heater block rests. The configuration of the opening 523 permits locking pins 590A and 590B provided on the flow cells 500A and 500B and the covers 514A and 514B with the substrates 510A and 510B positioned in the opening thereof to extend through the opening 523 to the opposite side from the side of insertion of the flow cells 500A and 500B.

Spring-loaded blocks 585A and 585B that have a central opening configured to be slidable along a respective positioning shaft 586A and 586B may be provided on the frame 519 proximate a bottom of the opening 523. The shafts 586A and 586B may have a head 589A and 589B on one end thereof and a spring (588A shown in FIG. 8) may be fitted between the blocks 586A and 586B and the heads 589A and 589B. The size of the heads 589A and 589B is larger than the size of the openings of the blocks 585A and 585B such that the blocks 585A and 585B cannot move off the shafts 586A and 586B past the heads 589A and 589B. The blocks 585A and 585B and shafts 586A and 586B may be positioned substantially in a center of each side of the opening 523 into which each flow cell 500A and 500B is received so as to cooperate with locating shoes 555A and 555B disposed at the bottom of each of the flow cells 500A and 500B. This helps to position and insert the flow cells 500A and 500B into the frame 519. In various exemplary embodiments, the locating shoes 555A and 555B may define a U- or C-shaped surface the concave side of which is configured to engage with and move along the positioning shafts 586A and 586B.

Figure 8:
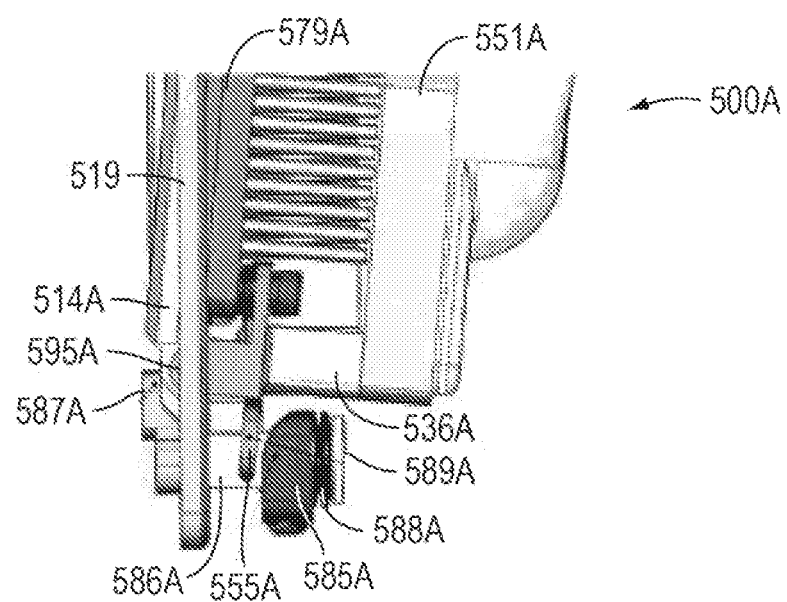
FIG. 8 is a close-up partial side view of the exemplary embodiment of FIG. 6 showing an exemplary step in the insertion of a detachable flow cell to the microscope stage.

With reference now to FIG. 8, a partial side view of an exemplary embodiment of the flow cell 500A during insertion into the frame 519 is depicted. It should be understood that the insertion of the flow cell 500B follows the same methodology. To insert the flow cell 500A, the entire flow cell 500A may be tilted as shown in FIG. 8 such that the locating shoe 555A engages around the shaft 586A between the spring-loaded block 585A and the frame 519. In this tilted position, the top of the flow cell 500A may be tilted outwardly away from the frame 519. On a side of the frame 519 opposite to the block 585A, a support member defining a support ledge 587A may be attached to an end of the shaft 586A that extends through the plate 519 opposite from the end of the shaft 586A proximate to which the block 585A is positioned. The ledge 587A may be configured to mate with a bottom portion of the cover 514A (e.g., a portion through which a hinge pin of the hinge 595A is inserted to hingedly couple the cover 514A to the plate 579A and frame elements 535A, 536A, and 551A). As the flow cell 500A is moved from the tilted position to a substantially vertical position (e.g., the top of the flow cell 500A is moved toward the frame 519), the locating shoe 555A moves away from the frame 519 and engages with the spring-loaded block 585A. The bottom of the flow cell is thus clamped into position between the forces from the support ledge 587A and the spring-loaded block 585A.

Figure 9:
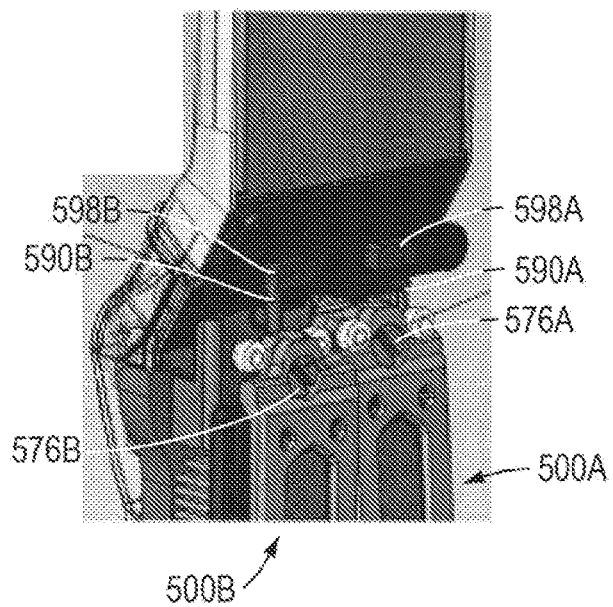
FIG. 9 is a close-up partial perspective view of the exemplary embodiment of FIG. 6.

Once the flow cell 500A is positioned substantially vertically within the frame 519, the top of the flow cell 500A may be locked into position using the rotating locking pin 590A. FIG. 9 shows a partial view of the flow cells 500A and 500B from the side of the frame 519 through which the covers 514A and 514B protrude when the flow cells 500A and 500B are inserted in the frame 519. In the view of FIG. 9, flow cell 500B is shown fully inserted and locked into position in the frame 519, while flow cell 500A is shown partially inserted in the frame 519 (e.g., the locking pin 590B is not in the locked position). The locking pins 590A and 590B may be mounted perpendicularly relative to a rotatable shaft (592A shown in FIGS. 5A and 5B). The locking pins 590A and 590B, via the rotatable shaft, can be rotated clockwise 90° from a substantially horizontal, unlocked position (e.g., substantially parallel with the ground) to a vertical, locked position (e.g., substantially perpendicular to the ground), as depicted by the position 590B in FIG. 9. When rotated into the vertical, locked position, a free end of the locking pins 590A and 590B are configured to engage with respective rubber blocks 598A and 598B mounted to the frame 519. The engagement between the locking pins 590A and 590B and the respective rubber blocks 598A and 598B is sufficient to cause a slight downward force on the respective flow cells 500A and 500B to clamp the flow cells 500A and 500B in and down.

Handles 594A and 594B may be mounted to the rotatable shafts 592A and 592B (shown in FIGS. 5A, 5B, and in cutaway in FIG. 10) opposite to the ends at which the pins 590A and 590B are mounted. So positioned, the handles 594A and 594B may provide a grasping mechanism with which a user can rotate the shafts and thus the pins 590A and 590B to lock and unlock the flow cells 500A and 500B in the frame 519. With reference to FIG. 6, handle 594A is in an unlocked position and extends outwardly from the duct 596A associated with flow cell 500A. Handle 594B in FIG. 6 is rotated 90° relative to the position of 594A in FIG. 6 and, due to a pivoting pin engagement with the shaft 592B, is brought into a position such that it lies within a recess in the outer surface of the duct 596B. Thus, to lock the flow cells 500A and 500B within the frame 519, the handles 594A and 594B may be rotated clockwise about 90° and folded downward in a pivoting motion relative to the shafts 592A and 592B and into the respective recesses in the ducts 596A and 596B. In such a position, it is clear to a user that the flow cells 500A and 500B are locked in position. Moreover, the locking pins 590A and 590B are prevented from being unlocked accidentally since to do so requires a user to lift the handles 594A and 594B and then to rotate the handle 594A and 594B. Such an exemplary configuration also may be desirable since the actuating mechanisms (e.g., handles 594A and 594B) to lock the flow cells 500A and 500B to the frame 519 are on an opposite side from the actuating mechanisms 576A and 576B to lock the covers 514A and 514B of the flow cells 500A and 500B.

Figure 10:
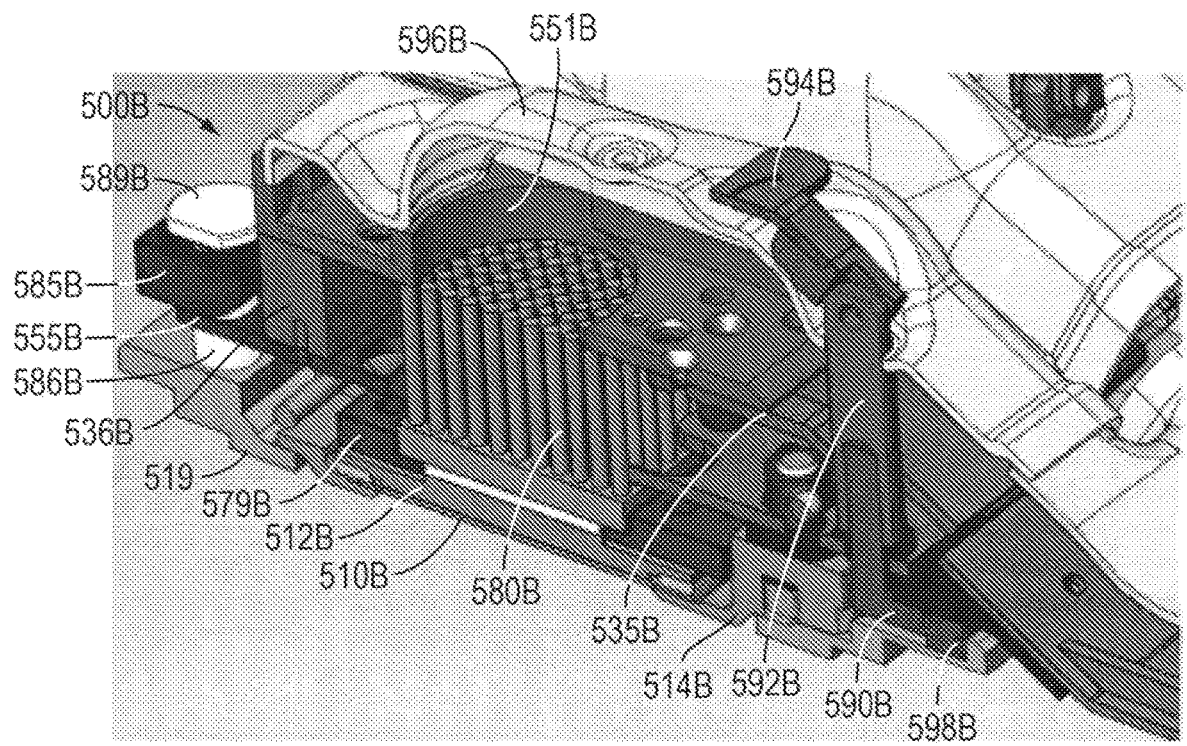
FIG. 10 is a close-up partial sectional view of the exemplary embodiment of FIG. 6.

FIG. 10 depicts a partial cutaway cross-sectional view of the flow cell 500B fully inserted in a locked position within the frame 519 adjacent flow cell 500A. The various elements of the flow cells 500A and 500B discussed above are labeled correspondingly in this cutaway view.

To facilitate loading of a substrate into a detachable flow cell, such as, for example, the detachable flow cells 500A and 500B described above, a benchtop loading fixture may be used. One exemplary embodiment of a benchtop loading fixture, and various parts thereof, useful for holding a detachable flow cell in position while a user positions a substrate therein is depicted in FIGS. 11-14.

Figure 11:
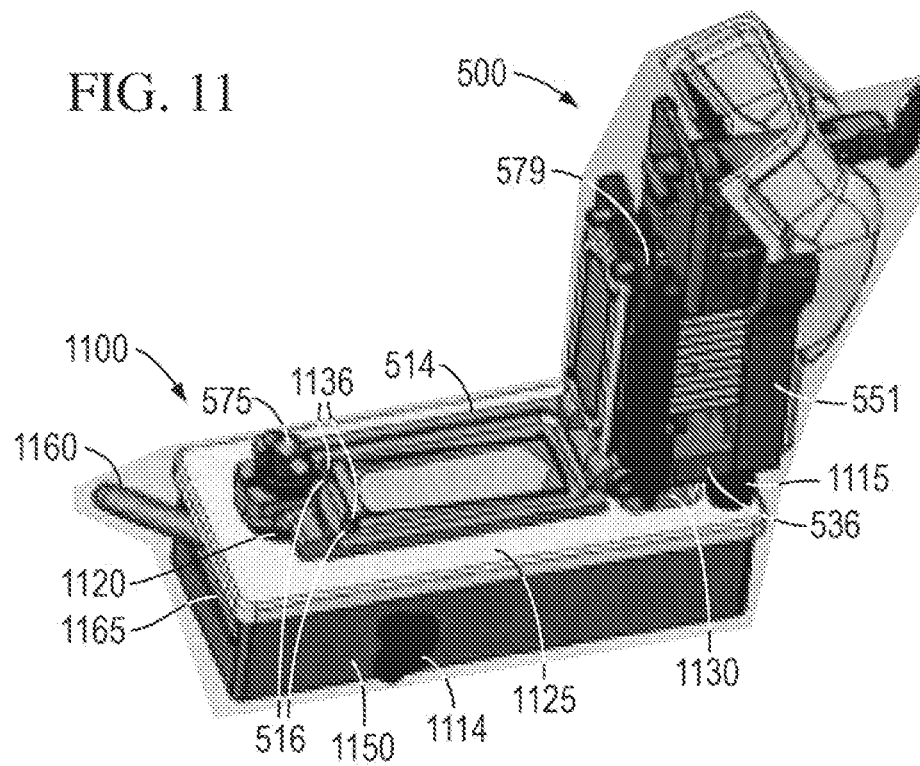
FIG. 11 is a perspective view of an exemplary embodiment of a bench top fixture with a detachable flow cell mounted thereto in accordance with the present teachings.
Figure 12:
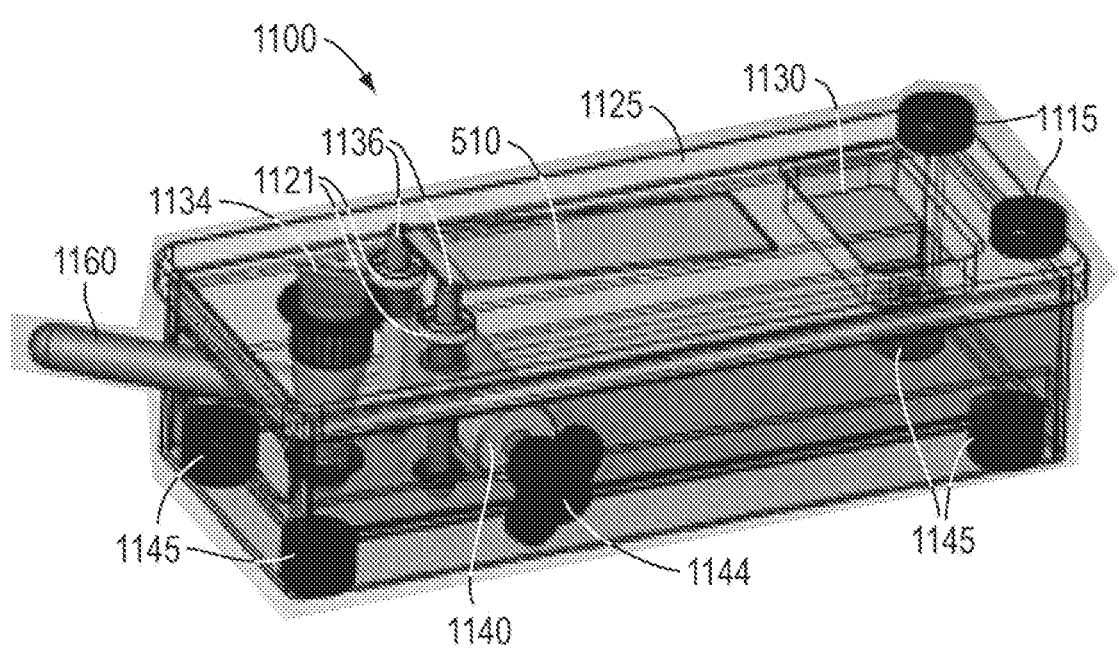
FIG. 12 shows the same view of FIG. 11 except with various parts made transparent.

Referring to FIG. 11, a bench top loading fixture 1100 is depicted with a flow cell 500 (flow cell 500 may have the configuration described above with reference to flow cells 500A and 500B of FIGS. 5-10) loaded onto the bench top loading fixture 1100 in an open position to position the substrate 510 to be subjected to reaction and/or analysis in the flow cell 500. FIG. 12 illustrates a transparent view of the bench top loading fixture 1100 with the flow cell 500 also made transparent so that only the substrate 510 is visible.

In an exemplary embodiment, the bench top loading fixture 1100 may include a housing 1150 substantially in the form of a rectangular box. The top surface 1125 of the housing 1150 may be configured to support the cover 514 of the flow cell 500, as shown in FIG. 11. More specifically, the top surface 1125 may define an opening 1120 therethrough. With reference to FIG. 12, extending through the opening 1120 may be a rotatable actuating member 1135 having an end portion 1136 configured to engage the flow cell to rotate the closure mechanism on the cover, as will be described in further detail below. Thus, the rotatable actuating member 1135 is configured to support the cover 514 of the flow cell 500 proximate the rotatable closure mechanism disposed at the free end of the cover 514, and the remaining length of the cover 514 is configured to rest on the top surface 1125 of the fixture 1150.

The top surface 1125 may also define a recess 1130 that is positioned just below the cover 514 when the flow cell 500 is in the supported position of FIG. 11. The recess 1130 is configured to receive part of the flow cell 500 (e.g., an end of frame 579) when the flow cell 500 is rotated to its open position, as shown in FIG. 11. Proximate the end of the top surface 1125 nearest the recess 1130, one or more stops 1115 may be positioned. The stops 1115 may provide a surface upon which the relatively heavier frame elements (e.g. 536 and 551) of the flow cell 500 may rest when the flow cell 500 is in the open position. The height of the stops 1115 may be sufficient to maintain the cover 514 and the remaining portions of the flow cell 500 substantially perpendicular to each other. In various exemplary embodiments, the stops 1115 may be made of rubber or other elastic material to provide a cushioned surface against which the flow cell frame elements may rest. As shown in FIG. 12, stops 1145 (e.g., rubber stops) also may be provided on the bottom surface of the fixture 1150 to help prevent sliding of the fixture 1150 relative to a surface on which it rests and to absorb motion associated with loading the flow cell 500 onto the fixture 1150.

Figure 13:
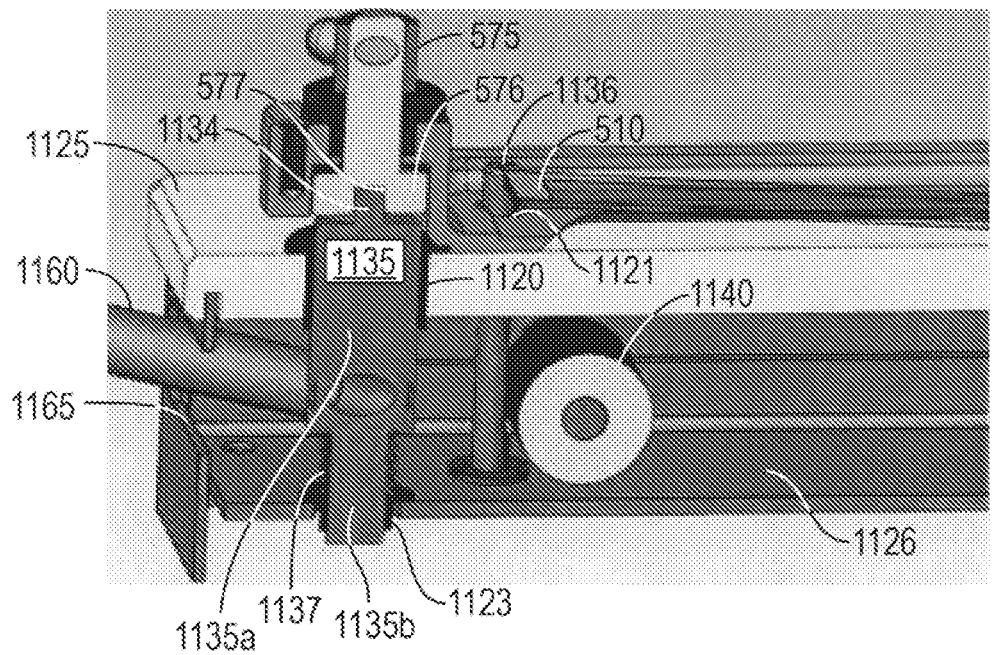
FIG. 13 is a partial sectional side view of various parts of the exemplary embodiment of FIG. 11.

Disposed proximate the opening 1120 and between the opening 1120 and recess 1130 are two holes 1121 that extend through the top surface 1125. The holes 1121 are positioned so as to substantially align with the holes 516 in the cover 514. As best seen in the views of FIGS. 12 and 13, a pair of pins 1136 extend through the housing 1150 of the fixture 1100 substantially perpendicularly to the top surface 1125. Inside the housing 1150, the lateral surfaces of the pins 1136 engage with the lateral surface of a friction roller 1140. The friction roller 1140 extends substantially perpendicular to the pins 1136. A winding member 1144 may be attached to a shaft extending through the roller 1140. The winding member 1144 may be positioned externally to the housing so that a user can grasp the winding member 1144 to rotate the roller 1140. Rotation of the roller 1140 causes the pins 1136 to move up and down through the holes 1121. Thus, as shown in FIGS. 11-13, the pins 1136 may be moved via the roller 1140 such that they extend through the holes 1121 and a substrate 510 that is desired to be loaded into the flow cell 500 may be positioned with its corners at a top edge thereof resting on the pins 1136 and the corners at the opposite edge thereof seated in the recess of the cover 514. Using the roller 1140, the pins 1136 may gradually be lowered to lower the edge of the substrate 510 resting on the pins 1136 down into the recess of the cover 514.

Figure 14:
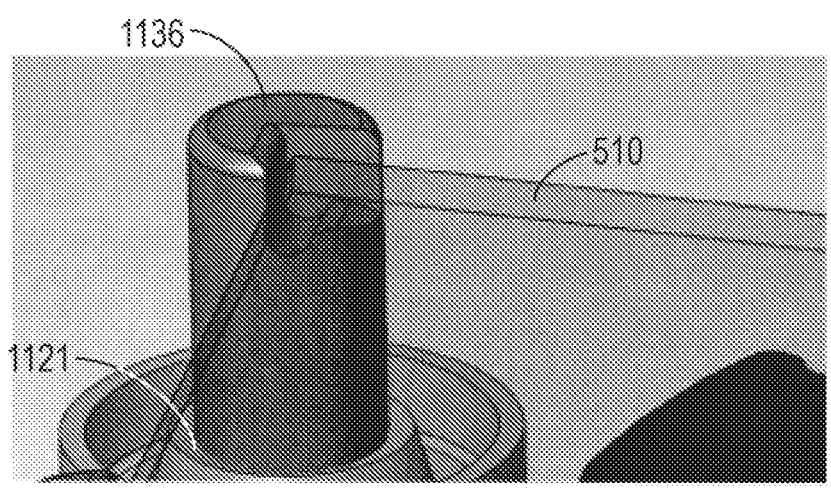
FIG. 14 is a partial close-up view of a pin used to hold a sample substrate in the exemplary embodiment of FIG. 11.

With reference to the close up view of FIG. 14, each pin 1136 may have a cut-out recessed segment that is configured to receive a corner of the substrate 510. The cut-out recess may be formed with relatively smooth surfaces so as to avoid the surface of the substrate 510 contacting sharp edges. Further, as the pins 1136 are lowered, the recessed surfaces of the pins 1136 may push against the respective corners of the substrate 510 to push the substrate 510 toward and eventually against the bottom edge of the recess in the cover 514 that receives the substrate 510.

With reference again to FIG. 13, operation of the actuating member 1134 will now be described. As mentioned above, the end of the actuating member 1134 that extends out of the hole 1120 to an exterior of the top surface 1125 has a protruding structure 1134 configured to engage with the actuation mechanism 576 of the flow cell 500. By way of example, the actuation mechanism 576 may comprise a substantially rectangular recess 577 and the protrusion 1134 may have a similar shape and be of a size configured to be received in the recess 577 in a mating engagement. In this way, the flow cell 500 can be supported at one end thereof by the actuation mechanism 576 resting on the protrusion 1134. The actuating member 1135 may have a larger upper region 1135a and a smaller bottom region 1135b. The smaller bottom region 1135b may be configured to be received in a hole 1123 that extends through a bottom surface of the housing disposed substantially opposite to the top surface 1125. The actuating member 1135 may be configured to be biased in an upward direction via a spring 1137 which is positioned around the smaller bottom region 1135b of the actuating member 1135 between an interior of the bottom surface 1126 and the larger upper region 1135a of the actuating member 1135. The spring 1137 may be configured to absorb some of the weight of the flow cell 500 when the flow cell is engaged with the actuating member 1135.

When it is desired to lock the cover 514 to the remainder of the flow cell 500, the flow cell 500 can be placed in the closed position and the actuating member 1135 may be rotated, which in turn causes rotation of the actuating mechanism 576 and rotatable closure mechanism 575. A lever 1160 may be coupled to the actuating member 1135 within the housing and may extend substantially perpendicular or at a slight angle relative to the longitudinal axis of the actuating member 1135. A slot 1165 may be provided on a lateral end surface of the housing and the lever 1160 may extend through the slot 1165. The lever 1160 may thus be moved along the slot 1165 to rotate the actuating member 1135 as desired.

Aside from a detachable flow cell arrangement that permits positioning a substrate in a horizontal position in the flow cell prior to closing the flow cell, it may be desirable to provide an independently accessible multiple (e.g., dual) flow cell arrangement permanently mounted to the microscope translation stage that is configured to permit positioning of a substrate by a user prior to closing the flow cell chamber to perform reactions and/or analysis on the substrate. Such an arrangement may permit loading the substrate and beginning reactions in the flow cell to be accomplished more quickly than in an arrangement wherein the flow cells are loaded in a detached position from the microscope stage. Moreover, since the flow cell may be connected to various reservoirs, pumps, and other flow mechanisms to flow substances for reaction and/or analysis into and out of the flow cell, it may be cumbersome to remove the flow cell from the microscope stage, requiring disconnection of the flow cell from various flow structures. Also, by permanently attaching a flow cell to the microscope stage and loading the substrate into such an attached flow cell, it may be possible to achieve better control over the positioning of the substrate and thus to focus the optics and other detection mechanisms more accurately.

In various exemplary embodiments, therefore, a flow cell may be configured to be loaded with a substrate in a horizontal position while the flow cell is mounted to a microscope stage. For example, in accordance with various exemplary embodiments, a user may load a substrate onto the sample block of the flow cell with the flow cell in an open position and, after the substrate is loaded on the sample block, close the flow cell such that the substrate is in a substantially vertical position in the formed flow cell reaction chamber for performing reactions and/or analysis. When utilizing a flow cell arrangement in which a substrate is loaded in a horizontal position, but moved to a vertical position for performing reactions and/or analysis when the flow cell is closed, it is desirable that the flow cell is configured to precisely position the substrate such that accurate imaging and detection of the substrate occurs. Thus, for example, it is desirable that the plane of the sample block on which the substrate is mounted and the plane of the substrate surface being imaged is substantially parallel to a focal plane of the microscope (e.g., including the various imaging optics and detection elements used to image the substrate). Moreover, since in some case the focal range of the microscope optics is somewhat limited, placing the substrate in a substantially predictable position when the flow cell is closed may make focusing on the substrate more efficient.

Figure 15:
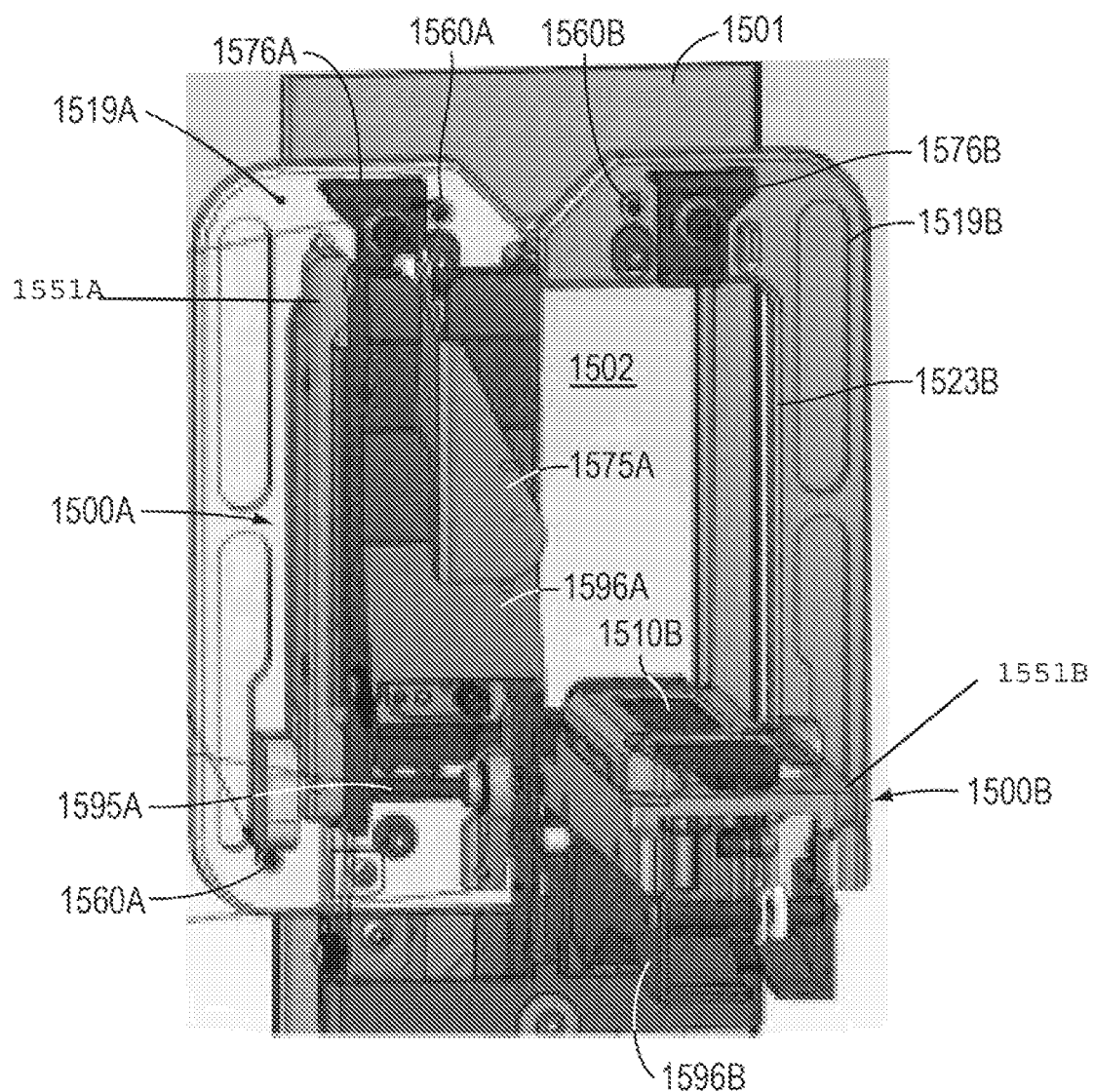
FIG. 15 is a perspective view of yet another exemplary embodiment of a dual flow cell system in accordance with the present teachings.

One exemplary embodiment of an independently accessible dual flow cell biological analysis instrument that permits a user to load a substrate into the flow cell in a horizontal position (e.g., with the large surface area of the substrate substantially parallel to the ground) is depicted in FIG. 15. In that exemplary embodiment, one or more frames, such as frames 1519A and 1519B having a substantially C-shaped configuration, may be affixed to the microscope stage 1501 and used to achieve appropriate positioning of a substrate being analyzed in a flow cell mounted to the frame when the flow cell is in a closed position, as will be explained in more detail below.

Figure 15A:
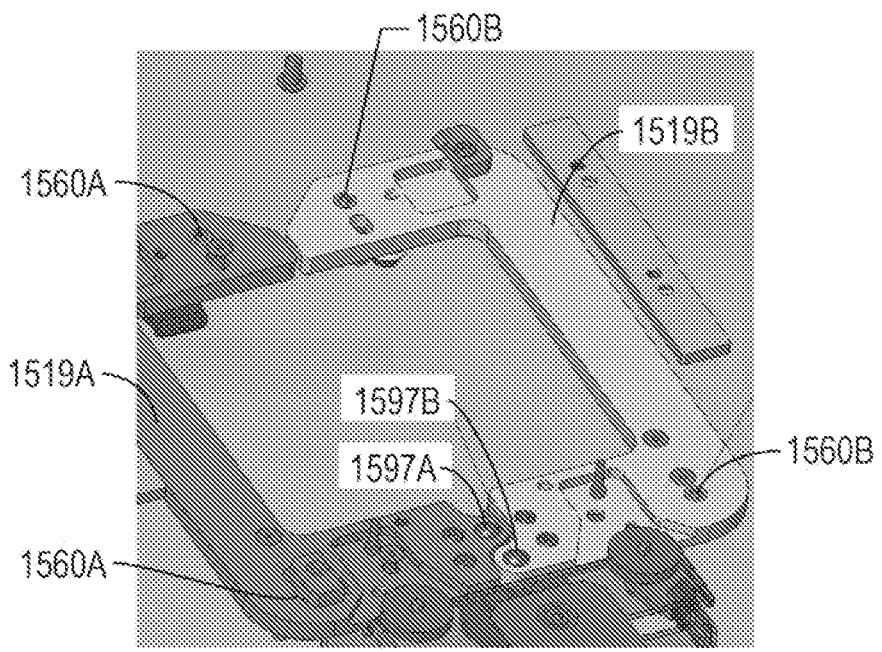
FIG. 15A is a partial top perspective view of an exemplary embodiment of C-shaped frames for mounting to a microscope stage for use with the exemplary embodiment of FIG. 15.

With reference to FIG. 15, in the independently accessible dual flow cell configuration shown, two substantially symmetrical C-shaped frames 1519A and 1519B (e.g., cover members) may be mounted to a microscope stage 1501. The flow cells 1500A and 1500B may be mounted to the respective frames 1519A and 1591B and placed in an open position (shown by flow cell 1500B) and closed position (shown by flow cell 1500A) by rotating (e.g., pivoting) the flow cells 1500A and 1500B relative to the frames 1519A and 1519B. A substantially rigid hinge shaft, shown by element 1595A in FIG. 15, may be used to mount the flow cells 1500A and 1500B to the frames 1519A and 1519B. A fixed ball rest, shown by elements 1597A and 1597B in FIG. 15A, also may be provided on each frame 1519A and 1519B. The fixed ball rests are configured to provide a support surface for the flow cells 1500A and 1500B in an open position such that the flow cell remains substantially horizontal (e.g., parallel to the ground). With reference to FIG. 15A, the frames 1519A and 1519B utilize the fixed balls 1597A and 1597B in conjunction with top and bottom jack screws 1560A and 1560B may be used to support the frames 1519A and 1519B relative to the microscope stage and also to adjust the frames 1519A and 1519B so that their lateral surfaces are substantially parallel to the microscope stage.

Figure 15B:
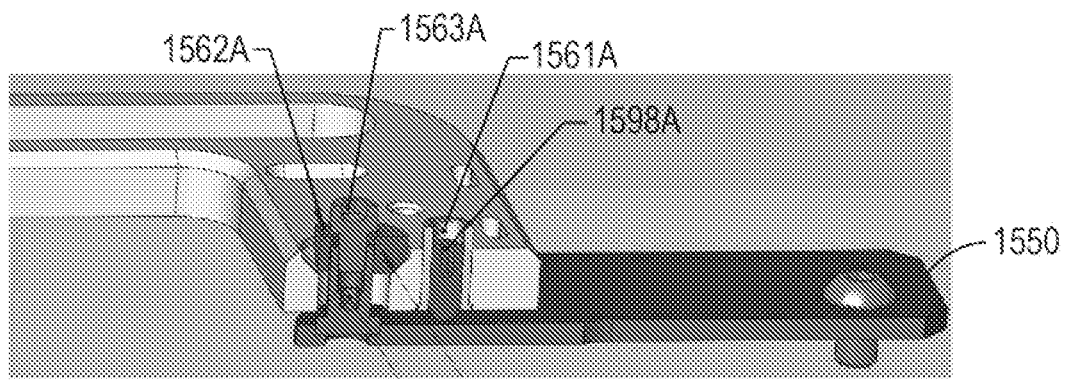
FIG. 15B is a partial cross-sectional perspective view of FIG. 15A and an exemplary embodiment of an adaptor bracket for mounting a C-shaped frame to a microscope stage.

FIG. 15B depicts a partial perspective cross-sectional view of frame 1519A showing the top jack screw 1560A mounted in a threaded sleeve 1561A for adjusting the frame 1519A relative to an exemplary embodiment of an adaptor bracket 1550 that may be bolted to the microscope stage. Alternatively, the frames 1519A and 1519B may be mounted directly to the microscope stage.

When mounted to the microscope stage 1501, the frames 1519A and 1519B define openings (1523B being shown in FIG. 15) that are configured to receive the faces of the flow cells 1500A and 1500B that hold the substrates 1510A and 1510B and sample blocks (not shown). In various exemplary embodiments, the substrate may be held in a carrier that is configured to be removably engaged with the sample block of the flow cell, which will be described below in more detail with reference to the exemplary embodiments of FIGS. 22-30 and 39-43. The openings of each frame 1519A and 1519B substantially align with the optically transparent region 1502 (e.g., opening) of the microscope stage 1501 to permit imaging of the substrates loaded in the flow cells 1500A and 1500B when the flow cells 1500A and 1500B are in the closed position.

The flow cells 1500A and 1500B may include a frame element 1551A and 1551B configured to support the sample blocks (not shown) on which the substrates are mounted. The frame elements 1551A and 1551B also may have various thermal components (e.g., a Peltier device, not shown, and/or a heat sink, shown by element 1580B) mounted to the frame elements 1551A and 1551B for providing heating and/or cooling of the reaction chambers formed by the flow cells 1500A and 1500B between the sample blocks and the mounted substrates (e.g., 1510B shown in FIG. 15); the formation of the reaction chamber between the sample block and the substrate is described above and therefore is not being described In this section. In various exemplary embodiments, for example, as depicted in FIG. 15, a duct 1596A and 1596B also may be supported by the frame element 1551A and 1551B and configured to mate with main ductwork (not shown) to deliver cooling fluid (e.g., air) from a remote cooling source (e.g., a fan) to cool the flow cell reaction chambers.

In an exemplary embodiment, as shown in FIG. 15, the ducts 1596A and 1596B may have open ends that are configured to mate with main ductwork to receive the cooling fluid positioned so as to face a bottom of the flow cells 1500A and 1500B when the flow cells are in a closed position (for example, to face toward a location of where the flow cells 1500A and 1500B attach to the frames 1519A and 1519B). Such a positioning of the ducts 1596A and 1596B may permit the cooling fluid delivered from the remote cooling source to be delivered from the bottom of the flow cells 1596A and 1596B and into the heat sink, as opposed to from a top of the flow cells 1596A and 1596B. This may permit the cooling fluid to be delivered while the flow cells 1500A and 1500B are in an open position without the cooling fluid flowing over the substrate, thereby reducing the risk of the substrates drying out. Those having ordinary skill in the art would understand that the various thermal components depicted in FIG. 15, including the ducts 1596A and 1596B, may be replaced or used in combination with various other thermal components to heat and cool the flow cell reaction chambers. Such thermal components that may be used include, but are not limited to, recirculating cooling liquid systems, heat pipes, evaporative cooling, and various other thermal systems such as those described in U.S. application Ser. No. 11/757,286, incorporated by reference herein.

To place the flow cells 1500A and 1500B in a closed, locked position, each flow cell 1500A and 1500B may include a lever lock 1575A and 1575B having a configuration and operational principles similar to lever locks 275A and 275B described above with reference to the exemplary embodiment of FIGS. 2A and 2B. The lever locks 1575A and 1575B are positioned substantially toward a top center of the flow cells 1500A and 1500B and include a handle portion that can be grasped by a user to lock the flow cells 1500A and 1500B. In the closed, locked position of lever lock 1575A illustrated in FIG. 15A, a length of the lever lock handle extends substantially vertically and parallel to the flow cell 1500A and serves as an obvious indication that the flow cell is in the closed, locked position. To open the flow cell, the handle portion of the lever lock 1575A is lifted upward.

Figure 44:
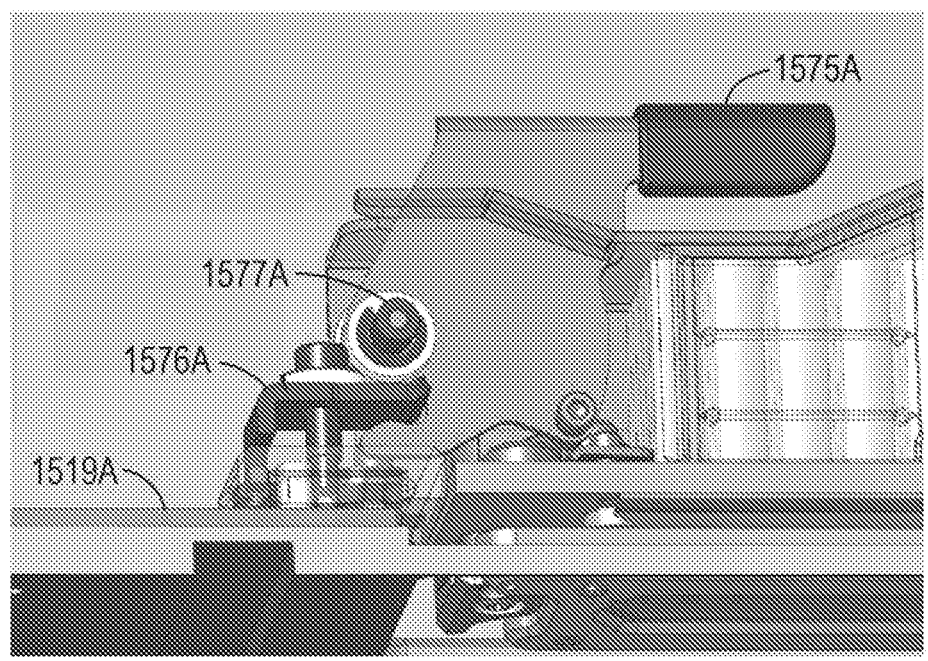
FIG. 44 is a partial cross-sectional view showing an exemplary embodiment of the lever lock of FIG. 15.

FIG. 44 illustrates a partial cross-sectional view of the flow cell 1500A of FIG. 15 illustrating lever lock 1575A in a locked position. In the closed position, a hook on the end of the lever lock 1575A engages with a flange member 1576A mounted to the C-shaped frame 1519A. As described above, lifting the handle portion of the lever lock 1575A upward in FIG. 15 rotates the lever lock 1575A about a pin and 1577A and moves the hook portion out of engagement with the flange member 1576A, thereby permitting the flow cell 1500A to be rotated to the open position shown by flow cell 1500B.

Once the flow cells 1500A and 1500B are in a closed position and mated with the frames 1519A and 1519B, the pair of leveling screws 1560A and 1560B provided on the frames 1519A and 1519B, for example one screw positioned proximate a top of the flow cell and one screw positioned proximate a bottom of the flow cell, may be adjusted to adjust the frames 1519A and 1519B, and thus the flow cells 1500A and 1500B, relative to the microscope stage. According to various exemplary embodiments, the leveling screws 1560A and 1560B, which may be jack screws, may work in conjunction with a mounting screw (shown by element 1563A in FIG. 15B). The mounting screws may be used to mount the frame 1519A and 1519B to the microscope stage 1501. The mounting screws may have spring washers, such as, for example, Belleville spring washers (shown by element 1562B in FIG. 15B), that permit the mounting screws to maintain a roughly constant holding force while the jack screws 1560A and 1560B are adjusted over a slight distance. The ability to adjust the leveling screws 1560A and 1560B permits adjusting the surface of the substrate in the flow cells 1500A and 1500B that is being imaged so that it is substantially parallel to the focal plane (or two-dimensional direction of travel) of the microscope stage.

In use, it is desirable that the mounting screws be appropriately adjusted relative to the range of the washer springs so that the mounting screws exert a force on the frames 1519A and 1519B and the microscope stage 1501 sufficient to substantially position the flow cells 1500A and 1500B without creating a bending force on the frames 1519A and 1519B and stage 1501.

Figure 16:
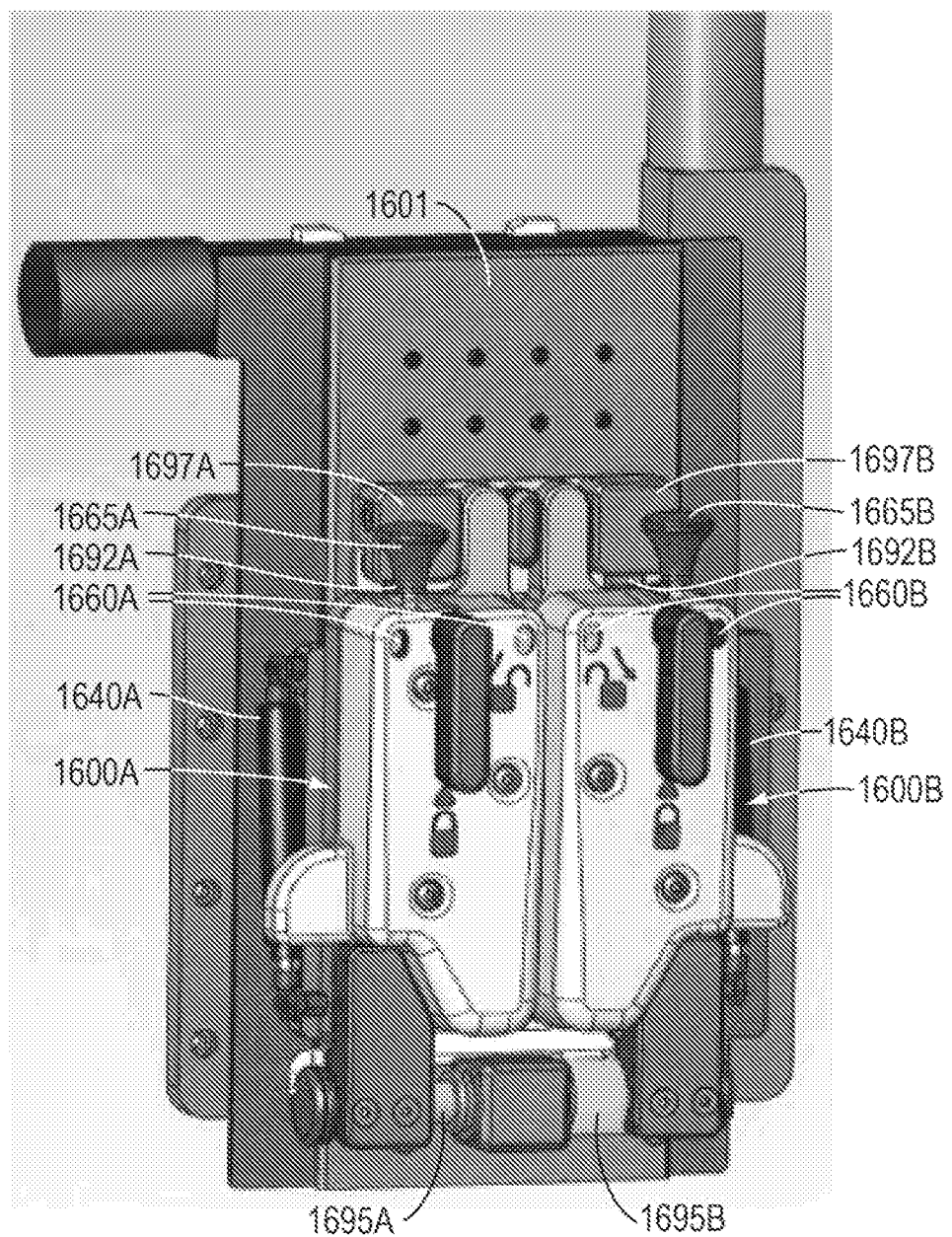
FIG. 16 is a perspective view of yet another exemplary embodiment of a dual flow cell system in accordance with the present teachings.
Figure 17:
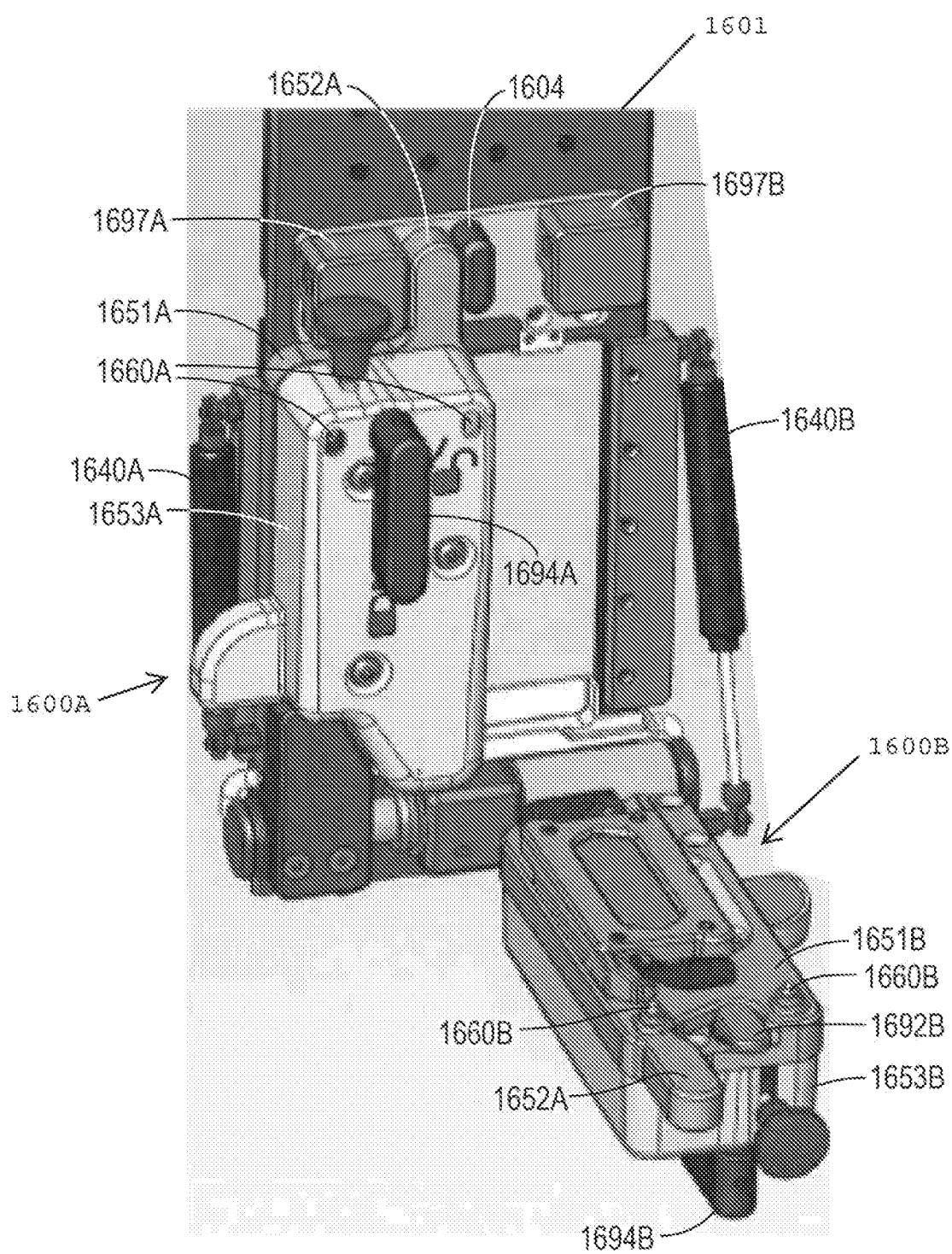
FIG. 17 is a perspective view of the exemplary embodiment of FIG. 16 showing one of the flow cells in a closed position and one of the flow cells in an open position.
Figure 18:
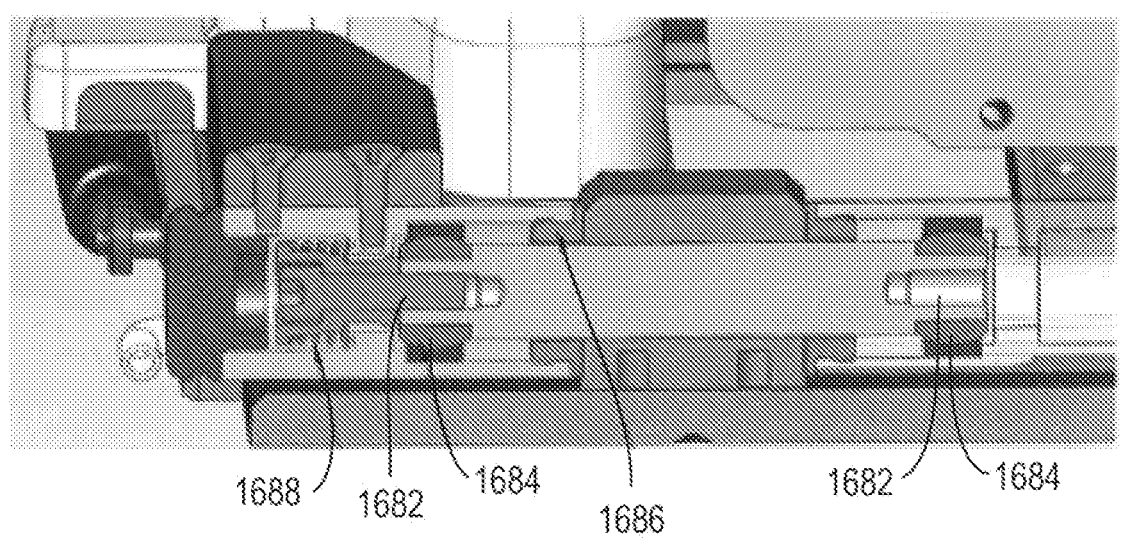
FIG. 18 is a partial sectioned view showing a hinge mechanism of the exemplary embodiment of FIG. 16.

Another exemplary embodiment of a flow cell arrangement configured to permit loading of the substrate into the flow cell in a horizontal position while the flow cell is mounted to the microscope stage is depicted in FIGS. 16-18. In the exemplary embodiment of FIGS. 16 and 17, flow cells 1600A and 1600B may be mounted directly to a microscope stage 1601, rather than to a frame that is mounted directly to the microscope stage like in the exemplary embodiment of FIG. 15 described above. In various exemplary embodiments, the microscope stage 1601 may be a microscope stage made commercially available by Ludl Electronic Products, Ltd., however, various microscope stages known to those skilled in the art may be employed in conjunction with the present teachings without departing from the scope thereof. FIG. 16 depicts both flow cells 1600A and 1600B in a closed position for performing reactions and/or analysis within the flow cell chambers. FIG. 17 depicts flow cell 1600A in a closed position and flow cell 1600B in an open position for loading a substrate, substrate 1610B shown in FIG. 17, in the flow cell 1600B. In the illustration of FIG. 17, the bottom portion of the microscope stage 1601 is not shown.

In the exemplary configuration of FIGS. 16 and 17, the flow cells 1600A and 1600B are mounted directly to the microscope stage 1601 via hinges 1695A and 1695B that include spherical bearings. As set forth in more detail below, the spherical bearing hinges 1695A and 1695B may provide a relatively wide range of motion (e.g., rotational motion) of the flow cells 1600A and 1600B relative to the microscope stage 1601, but also serve as a fixed rest point for the flow cells 1600A and 1600B when they are in the open position, as shown by flow cell 1600B in FIG. 17.

Details of the hinge mechanism 1695A are depicted in the close-up, sectioned view of the hinge mechanism 1695A shown in FIG. 18. The view of FIG. 18 shows the interior of the hinge 1695A with the flow cell 1600A being removed therefrom. The hinge mechanism 1695B has the same structure as hinge 1695A, but is oppositely configured such that the two are mirror images of each other. The hinge 1695A includes two shafts 1682 disposed at substantially opposite ends and on which the flow cell 1600A is configured to be rotatably mounted. A spherical bearing 1684 surrounds each shaft 1682 to permit the shafts 1682, and thus the flow cell 1600A, to move rotationally and at an angle. An outer bushing 1686 may be used to limit the tilt of the spherical bearings 1684. The outer bushing 1686 may be configured to permit the spherical bearings 1684 to have a range of motion sufficient for leveling the flow cell in the closed position (e.g., for adjusting the large surface area of the substrate in the flow cell such that it is substantially parallel with the focal plane of the microscope optics), but limit the range of motion such that the flow cell 1600A does not move significantly (e.g., clockwise or counterclockwise) during loading of the flow cell 1600A when in the open position. It is desirable that the bearings 1684 return to substantially the same position when moving the flow cell 1600A from the open to the closed position. In various exemplary embodiments a preloaded spring 1688 may be used to return the bearings 1684 to substantially the same position each time the flow cell 1600A is moved to the closed position. As such, the force applied by the spring 1688 may be selected such that it is at least equal to the weight of the flow cell and any other forces that tend to deflect the position of the bearing 1684 when the flow cell is closed.

In addition to the spherical bearing hinges 1695A and 1695B to control the motion of the flow cells 1600A and 1600B as they move between the open and closed positions, dampers 1640A and 1640B may be attached at one end to the microscope stage 1601 and at the opposite end to the flow cells 1600A and 1600B to facilitate smooth operation and control over the opening and closing of the flow cells 1600A and 1600B. Those having skill in the art would understand a variety of suitable configurations for the dampers 1640A and 1640B. By way of example only, the dampers 1640A and 1640B may be either hydraulic or pneumatic dampers. In an alternative embodiment, since the flow cells are relatively light, a friction-based damping mechanism may be employed since the friction needed to stop the motion of a flow cell is less than a user could relatively easily exert.

Although, as discussed above, the spherical bearings of the hinges 1695A and 1695B serve to return the flow cells 1600A and 1600B to substantially the same position each time the flow cells 1600A and 1600B are moved from the open to the closed position, it may also be desirable to provide a mechanism for fine-turning the adjustment (e.g., level) of the flow cells 1600A and 1600B in the closed position to accurately position the substrates therein such that the surface of larger area of the substrate is parallel to and in the focal plane of the optics and detection mechanisms of the microscope. To achieve this fine-tuning of the position of the flow cells 1600A and 1600B, one or more leveling screws disposed toward a top of the flow cells 1600A and 1600B in the closed position may be used.

With reference to the exemplary embodiment of FIGS. 16 and 17, a pair of leveling screws 1660A and 1660B may be provided proximate the end of each of the flow cells 1600A and 1600B opposite to the end at which the flow cells 1600A and 1600B are hinged to the microscope stage 1601. The leveling screws 1660A and 1660B may be configured to adjust the position of the flow cells 1600A and 1600B in a direction substantially perpendicular to the plane of the drawing sheet to alter the position of the substrates within the flow cells within and parallel to the focal plane of the microscope. The leveling screws 1660A and 1660B may be actuated from external the flow cells 1600A and 1600B when they are in the closed position. For example, a screwdriver or other tool designed to engage with a head of the leveling screws, may be used to turn the leveling screws 1660A and 1660B to achieve desired positioning of the flow cells 1600A and 1600B and thus the substrates loaded therein.

In various exemplary embodiments, a force exerted by the leveling screws 1660A and 1660B to move the flow cells 1600A and 1600B outwardly from the microscope stage 1601 during adjusting of the position of the flow cells 1600A and 1600B may act against the a closure mechanism (e.g., a latch) configured to lock the flow cells 1600A and 1600B in a closed position (e.g., as shown in FIG. 16). It may be desirable therefore to configure the latch to provide a relatively constant closure force over a relatively wide range of adjustment of the flow cells 1600A and 1600B (in other words, a relatively wide range of force exerted against the closure mechanism by the leveling screws 1660A and 1660B). In the exemplary embodiments of FIGS. 16 and 17, and as shown in more detail in the detailed, sectioned view of FIG. 19 and the close-up views of FIGS. 20 and 21, a closure mechanism that includes a latch element and compression spring may be used to permit a relatively wide range of adjustment by the leveling screws 1660A and 1660B without risk of overcoming the closure force.

Figure 19:
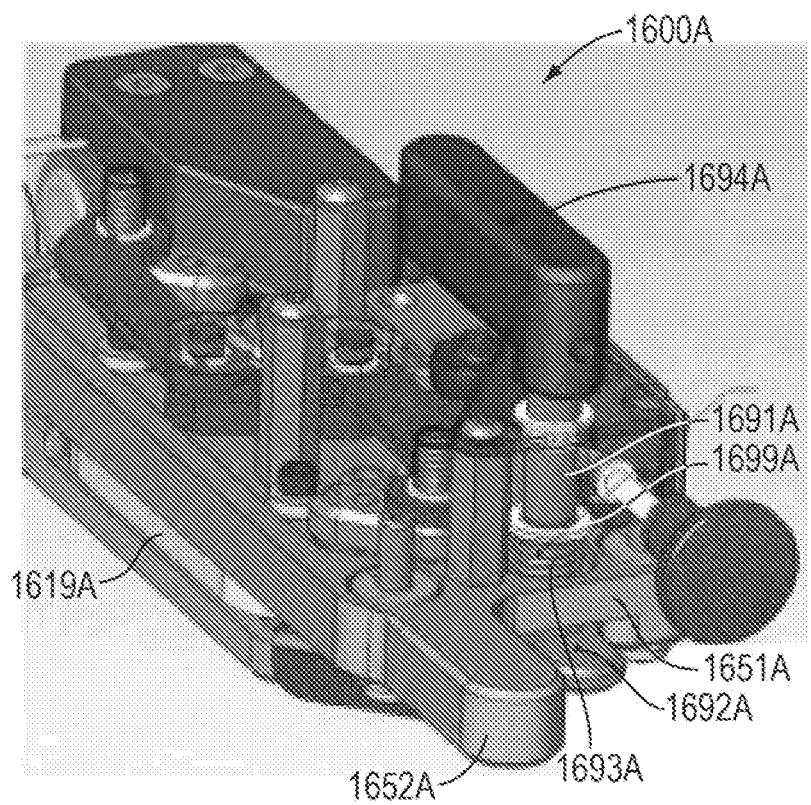
FIG. 19 is a view of a flow cell of the exemplary embodiment of FIG. 16 showing interior portions of the flow cell housing.
Figure 20:
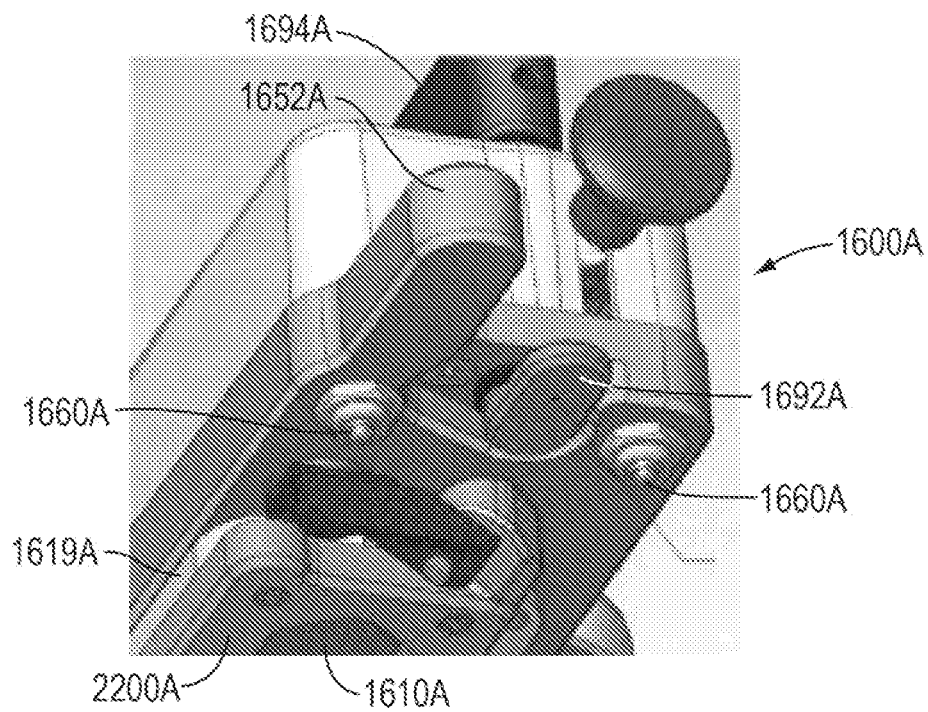
FIG. 20 is a partial bottom perspective view of a flow cell of the exemplary embodiment of FIG. 16.
Figure 21:
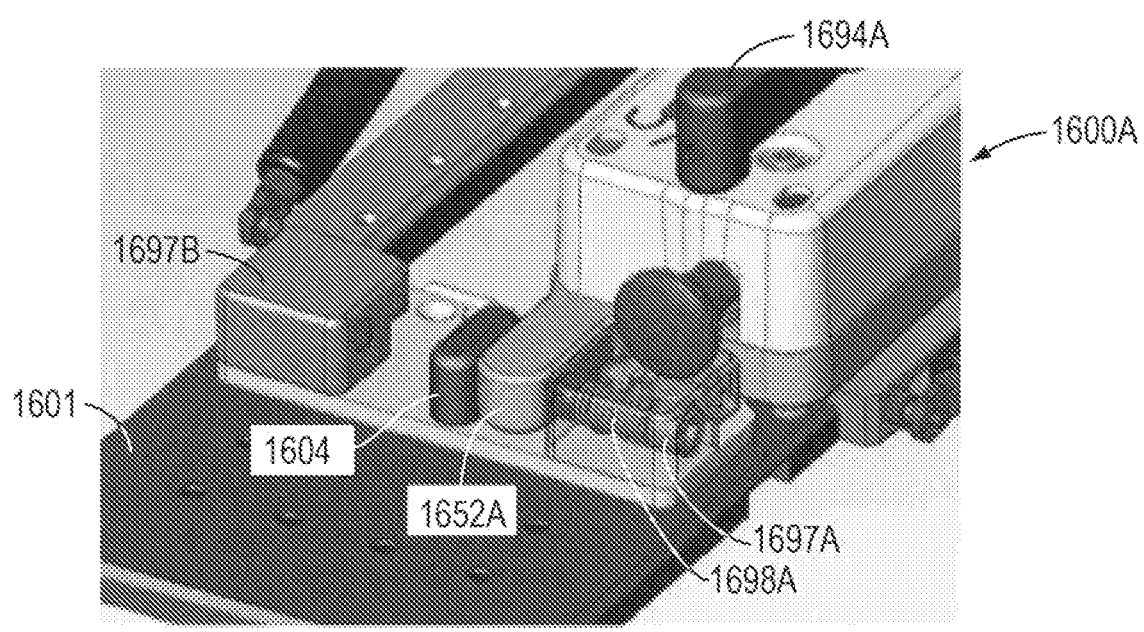
FIG. 21 is a partial top perspective view of the exemplary embodiment of FIG. 17.

With particular reference to FIGS. 19, 20, and 21, a closure mechanism in accordance with various exemplary embodiments will be described with reference to the flow cell 1600A, though it will be understood that the flow cell 1600B also may be provided with such a closure mechanism. The closure mechanism may comprise a rotatable latch 1692A that extends from an end of a rotatable shaft 1691A in a direction substantially perpendicular to the longitudinal axis of the shaft 1691A. A handle 1694A may be provided on an end of the shaft 1691A opposite to the latch 1692A and may be positioned externally to the housing of flow cell 1600A, as best shown in FIGS. 16, 17, 20, and 21. The handle 1694A may be pivotably mounted at one end to the flow cell 1600A and configured to rotate approximately 90° from a substantially horizontal position (e.g., parallel to the ground) to a substantially vertical position, shown in the figures, to lock the flow cell 1600A into position relative to the microscope stage 1601 when the flow cell 1600A is in the closed position. Rotation of the handle 1694A causes rotation of the shaft 1691A and latch 1692A. Rotating the latch 1692A moves the latch 1692A into and out of engagement with a cooperating lip on a closure block 1697A (shown in FIG. 16, 17, and in a transparent view in FIG. 21; closure blocks 1697B configured to cooperate with the latch (1692B) on flow cell 1600B also are shown in those figures) mounted to the microscope stage 1601. Those having skill in the art are familiar with various types of suitable configurations exemplifying the type of latching mechanisms described above.

The closure mechanism also may include a compression spring 1693A disposed around the rotatable shaft 1691A between a washer 1699A and the frame 1651A. A bushing (not shown) surrounds the shaft 1691A within the frame 1651A, permitting the shaft 1691A to rotate and move up and down relative to the frame 1651A The spring 1693A may be configured to provide the force that maintains the flow cell 1600A in the locked, closed position relative to the microscope stage 1601. Further, the spring 1693A may permit a relatively wide range of adjustment of the flow cell 1600A by the leveling screws 1660A and 1660B in a direction substantially perpendicular to the plane of the drawing sheet of FIG. 16 while maintaining a substantially constant closing force between the latch 1692A and the closure lip on block 1697A. By utilizing the compression spring 1693A, the latch 1692A need not be in an exact position relative to the closure block 1697A to lock the flow cell 1600A.

In contrast to other closure mechanisms such as, for example, a thumb screw, the closure mechanism described above with reference to FIGS. 19-21 permits a user to easily determine whether the corresponding flow cell is in a locked position or unlocked position, and also controls the closure force independent of user operation. However, those of ordinary skill in the art would understand a variety of differing types of closure mechanisms could be used to lock the flow cells in a closed position, including but not limited to, thumbscrews and/or other similar mechanisms, without departing from the scope of the present teachings.

With reference in particular to FIGS. 19-21, additional elements that may be associated with the flow cells 1600A and 1600B to facilitate locking the flow cells 1600A and 1600B and appropriately positioning the flow cells 1600A and 1600B such that the substrates therein are in the focal plane of the microscope imaging elements will now be described. FIGS. 19-21 again depict flow cell 1600A, but it should be understood that flow cell 1600B can be similarly configured. In various exemplary embodiments, the frame 1651A may include a protrusion 1652A (e.g., tongue) that extends upwardly from an end of the frame 1651A when the flow cell 1600A is in the closed position (e.g., the protrusion 1652A extends upwardly in the orientation shown in FIG. 16). More specifically, in the closed and locked position, the protrusion 1652A is configured to be positioned between the closure block 1697A on one side and a stop 1604 (which may be made of rubber or other suitable elastic material configured to provide a compression against the protrusion 1655A) on the other side. The protrusion 1652B of flow cell 1600B (depicted, for example, in FIG. 16) may similarly be configured to be positioned between the closure block 1697B and the stop 1604 in the closed position of the flow cell 1600B.

A spring-loaded shaft 1698A housed in the closure block 1697A may be biased so as to extend out of the closure block 1697A and into contact with a side of the protrusion 1652A. The protrusion 1652A may thus be clamped between the stop 1604 and the shaft 1698A. In various exemplary embodiments, the shaft 1698A may have a ball or other element on the end thereof that contacts the protrusion 1652A so as not to cause damage thereto. For example, the ball or other contact element may be made of a material, such as rubber, for example, that minimizes damage to the protrusion 1652A. In addition to the force applied by the shaft 1698A, the action of rotating the latch 1692A also may push the protrusion 1652A against the stop 1604 to provide an additional clamping force.

When the flow cells 1600A and 1600B are placed in a closed and locked position, as has been described above, the respective spherical bearing hinges and leveling screws may cooperate to adjust the flow cells 1600A and 1600B such that the substrates therein are positioned in the appropriate focal plane of the microscope (e.g., the larger area surface of the substrate that is being images is positioned within and parallel to the focal plane). The spherical bearing hinges and protrusions may then cooperate to position the flow cells 1600A and 1600B in a particular position within the focal plane (e.g., move the flow cells 1600A and 1600B in a direction parallel to the focal plane). As long as the flow cells 1600A and 1600B remain in the same position within the focal plane of the imaging instrumentation throughout a reaction and/or analysis procedure, the exact position of the flow cells 1600A and 1600B along the focal plane is not critical.

A flow cell configuration that enables a user to load the substrate or other sample holder into the flow cell in a substantially horizontal position may facilitate the loading of the substrate as the substrate is easier to manipulate onto a horizontal surface than a vertical surface. Further, as discussed above, mounting a substrate in the substantially horizontal position may provide an opportunity for a user to clean any contamination or other substances at least from the surface of the substrate that faces the user after the substrate has been loaded in the flow cell. In addition, loading the substrate in a substantially horizontal position may hinder substance adhered to the substrate, such as, for example, glycerol that is placed on the slide to prevent the slide from drying out, from flowing down the surface of the substrate and dripping onto other components of the flow cell. Also, handling and loading the substrate in a horizontal position may permit the substrate to be loaded more rapidly, thereby decreasing the time that the substrate is exposed to the air and the risk of the substrate drying out.

Aside from providing a flow cell arrangement in which a sample substrate can be loaded in a horizontal position, it may be desirable to minimize direct handling of the substrate by a user loading the substrate and/or transporting the substrate from one workstation to a flow cell for performing reactions and/or analysis of the sample substrate. It also may be desirable to minimize contact between clamping equipment and the substrate when mounting the sample substrate in a flow cell.

To achieve at least some of these desirable features, in various exemplary embodiments, a slide carrier may be configured to hold the sample substrate during loading of the flow cell and within the flow cell while reactions and/or analysis of the substrate is performed. FIGS. 22-29 and 39-43 depict various views of some exemplary embodiments of a slide carrier and how that carrier may be configured to be coupled to a frame and sample block of a flow cell configured for enabling loading of a substrate in a horizontal position (such as, for example, the flow cells 500A, 500B, 1500A, 1500B, 1600A, or 1600B described above).

Figure 22:
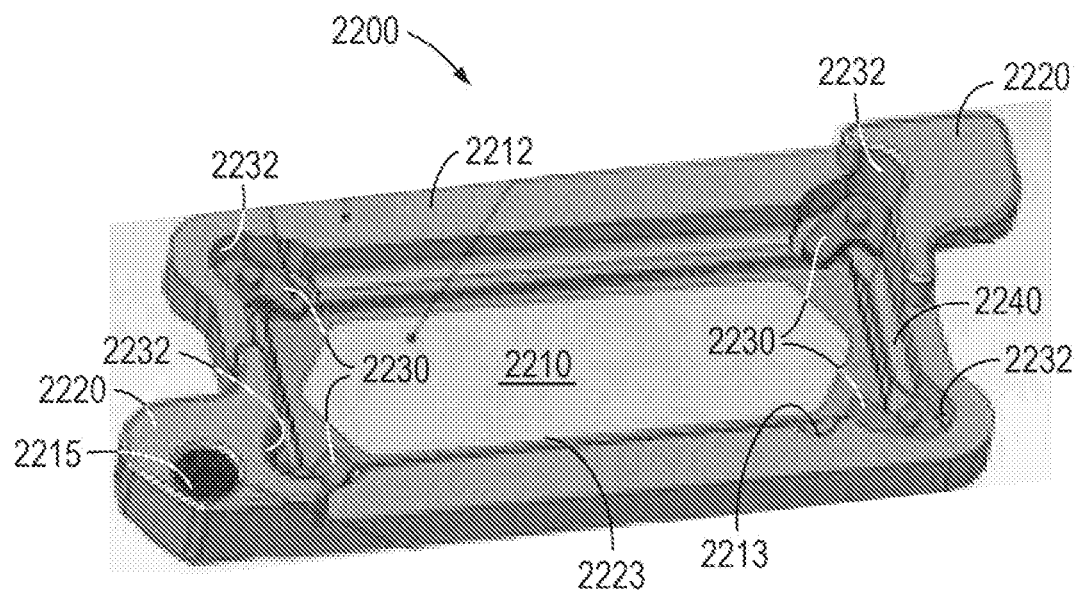
FIG. 22 is a perspective view of an exemplary embodiment of a substrate carrier in accordance with the present teachings.

With reference to FIG. 22, one exemplary embodiment of a slide carrier is depicted. The slide carrier 2200 is in the form of a frame 2212 configured to surround the substrate 2210. In various exemplary embodiments, carrier frames in accordance with exemplary embodiments may be made of machined aluminum. Other suitable materials for the carrier frames disclosed herein may include materials that are stiff enough to withstand a force required to compress the sealing mechanism on the heater block without flexing. The frame 2212 defines a relatively large opening 2223 that is configured to substantially align with a portion of the large surface area of the sample substrate 2210 when the sample substrate 2210 is positioned therein. Surrounding the opening 2223, the frame 2212 has a stepped profile, the lower portion of which in the view of FIG. 22 is configured to support the sample substrate 2210 substantially around a perimeter region of the substrate 2210. In various exemplary embodiments, for reasons that will become apparent in the description that follows, the substrate 2210 may be received in the frame 2212 such that the surface of the substrate 2210 facing up in the orientation of FIG. 22 is the surface that carries the sample to be analyzed and/or reacted. As shown in FIG. 22, the thickness of the frame 2212 may be larger than the thickness of the substrate 2210. A radiused region 2240 may be formed in the frame 2212 and extend around the perimeter of the substrate 2210 when the substrate 2210 is mounted in the carrier 2200. The radiused region 2240 may collect any substance that may drip off of the mounted substrate 2210 when the substrate 2210 is placed in a substantially vertical position upon closing the flow cell.

Retaining fingers 2230 may be pivotably mounted to the slide carrier frame 2212. In various exemplary embodiments, four retaining fingers 2230 may be positioned to engage with the substrate 2210 proximate the four corners of the sample substrate 2210. Operation and additional details regarding the retaining fingers 2230 are described below.

The slide carrier 2200 also may include, in various exemplary embodiments, clamping extensions 2220 (e.g., ears) on two diagonally opposing corners thereof, the purpose of which will become apparent from the more detailed explanation set forth below. In accordance with various exemplary embodiments, one of the clamping extensions 2220 may be provided with an indicator 2215, such as, for example, a bar code label, radio-frequency identification (RFID) tag, and/or other indicator useful for identifying the carrier and/or containing information about the sample on a given slide held by the carrier.

Figure 23:
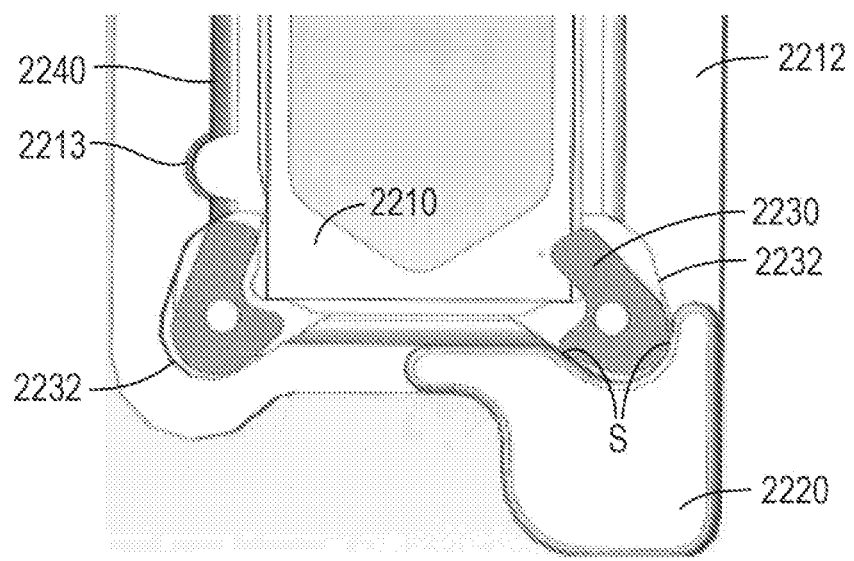
FIG. 23 is a partial close-up plan view of the substrate carrier of FIG. 23.

Referring now to FIG. 23, two of the retaining fingers 2230 are depicted, with the one on the left of the figure illustrating a disengaged position of the retaining finger 2230 relative to the substrate 2210 and the one on the right illustrating an engaged position of the retaining finger 2230 in which the retaining finger 2230 clamps the substrate 2210. The retaining fingers 2230 may be positioned in respective recessed regions 2232 of the carrier frame 2212. The recessed regions 2232 and the retaining fingers 2230 may have cooperating profiles such that one or more surface portions of the recessed regions 2232 engages with one or more surface portions of the retaining fingers 2230 as the fingers 2230 are rotated into the clamping position shown by the right retaining finger 2230 in FIG. 23. The engagement of the one or more surface portions of the retaining fingers 2230 and recessed regions 2232 stops further rotation of the retaining fingers 2230. In the exemplary embodiment of FIG. 23, the surface portions of the retaining finger 2230 and the recessed region 2232 that engage are identified by S.

Rotation of the retaining fingers 2230 out of engagement with the recessed regions 2232 permits the retaining fingers 2230 to be move entirely away from the surface of the substrate 2210 to permit the substrate 2210 to be removed from the carrier frame 2212. The retaining fingers 2230 may be rotated via screws or other mechanisms familiar to those skilled in the art (not shown). It may be desirable to configure the retaining fingers 2230 and recessed regions 2232 such that each of the retaining fingers 2230 is configured to be rotated in the same direction to place the retaining fingers 2230 in a clamping position and likewise to place the retaining fingers 2230 in a disengaged position. Those having ordinary skill in the art would understand various modifications that could be made to the exemplary embodiments shown herein to achieve such common direction of rotation.

In various exemplary embodiments, the retaining fingers in accordance with various exemplary embodiments of the present teachings may be made of stainless steel with the tips coated with rubber to provide a soft surface between the fingers and the substrate. Other materials that may be used for retaining fingers include materials that are soft enough so as not to damage the substrate when placed in contact therewith, yet strong enough to withstand wear and tear.

Once the substrate 2210 for which reaction and/or analysis is desired is positioned and clamped in the carrier 2200, the entire carrier 2200 with the substrate 2210 therein may be loaded into a flow cell, as depicted in the exemplary embodiment of FIGS. 24-29. Although the configuration of the flow cell depicted in FIGS. 24 and 26-29 is like that of the flow cells 1600A and 1600B described above, it should be understood that the manner in which the substrate carrier 2200 is loaded may also be implemented in a flow cell having a configuration like that of flow cell 1500A or 1500B, or other flow cells described herein, with appropriate modifications to such flow cells to include mechanisms for holding the substrate relative to the heater block, for example. In FIGS. 24-29, the flow cell being described is flow cell 1600A; it should be understood that the various parts of the flow cell 1600A applies to the flow cell 1600B, with orientation and positioning of the various elements being modified as appropriate.

To load the carrier 2200, the position of the assembly shown in FIG. 23 is inverted such that the recess defined by the frame 2212 receives the sample block 1612A, causing the surface of the substrate 2210 that has sample attached thereon to rest on a sealing mechanism 1615A (e.g., gasket) on the upper surface of the sample block 1612A.

In the cutaway view of the carrier 2200 shown in FIG. 23, the stepped profile of the frame 2212 is visible. That profile provides two regions, the first region 2227 for nesting with the substrate 2210 and the second region 2228 defined by the radiused portion 2240 for nesting with the sample block 1612A. Thus, the frame 2212 may be configured to envelope the sample block 2212, surrounding it entirely around its perimeter and surface facing away from the sample block 1612A. The outer perimeter of the frame 2212 may be supported upon a support plate 1619A to which the sample block 1612A is mounted on one side. The opposite side of the support plate 1619A faces the frame element 1651A of the flow cell and the support plate 1619A may be mounted to the frame element 1651A. In various exemplary embodiments, the support plate 1619A may cover any gaps in the frame 1651A to enclose wires and prevent splashed liquid from entering the interior of the flow cell.

Mounting the carrier 2220 and substrate 2210 in this manner forms a reaction chamber between the substrate 2210 and the sample block 1612A into which various substances (e.g., samples, reagents, buffers, etc.) may be introduced for the purpose of reacting with a sample on the substrate 2210 and/or performing analysis of the substrate 2210. Those ordinarily skilled in the art would understand various flow structures and flow control mechanisms (e.g., ports, conduits, valving, pumps, etc.) that can be used to introduce substances into the reaction chambers of the flow cells described herein; details regarding such flow mechanisms therefore are not provided.

Figure 24:
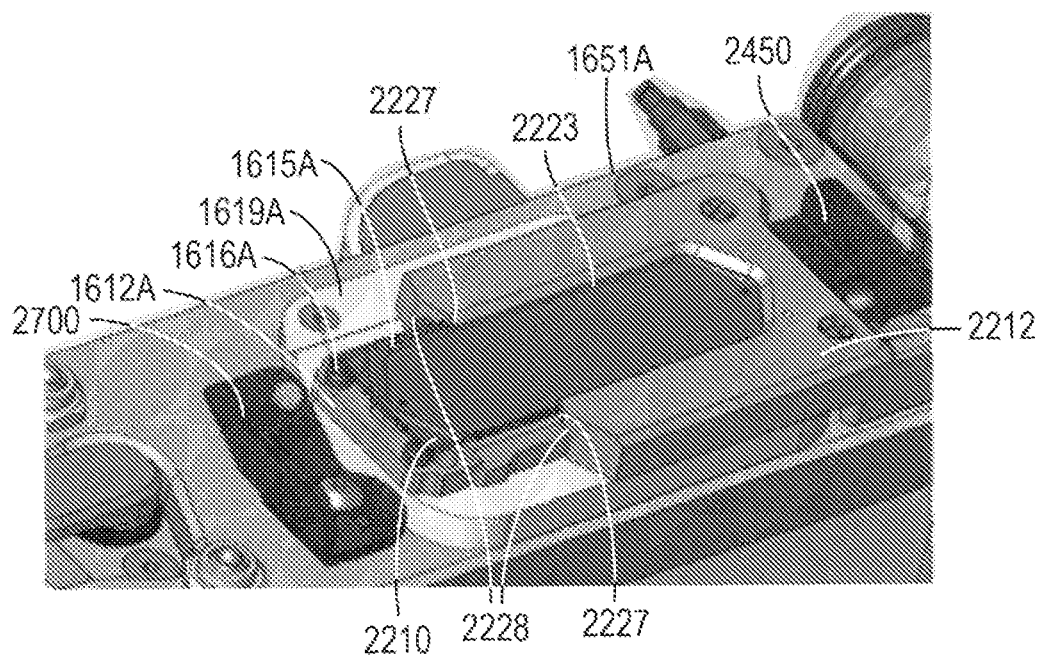
FIG. 24 is a partial perspective view showing the substrate carrier of FIG. 23 loaded in a flow cell of FIG. 16.
Figure 25:
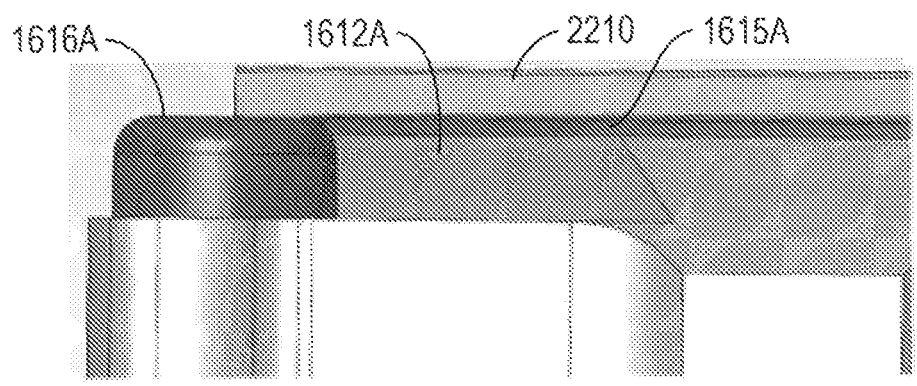
FIG. 25 is a close-up view of an exemplary embodiment of a spacer used to support a substrate mounted in a flow cell in accordance with the present teachings.

As shown in FIG. 24, and in the close-up elevational view of FIG. 25 (the view of FIG. 25 is a partial side view taken from a long side of the substrate 2210), spacers 1616A may project up from the surface of the sample block 1612A to engage and support the substrate 2210. The spacers 1616A (only two of which are shown in FIGS. 24 and 25) are disposed to support the four corners of the substrate 2210. As best seen in FIG. 25, the surfaces of the spacers 1616A on which the substrate 2210 rests are slightly higher than the surface of the sample block 1612A with which the substrate 2210 forms the reaction chamber. The spacers 1616A may thus be configured to fix the gap between the sample block 1612A and the substrate 2210 to determine the volume of the reaction chamber formed therebetween and thus the volume of liquid that may be held in the reaction chamber. In various exemplary embodiments, the spacers 1616A may be parts that are separate from the sample block 1612A so that at least the top surface of the sample block 1612A that defines the flow cell reaction chamber may be lapped and polished. The spacers 1616A may be made of, for example, stainless steel and/or other suitable materials offering sufficient rigidity. It is desirable for the spacers 1616A to be relatively hard and not deformable (e.g., compressible) so that resting the substrate 2210 on the spacers 1616A determines the position of the substrate 2210 when the flow cell is in the closed position; in other words, the focal plane of the substrate 2210 may be set by resting the substrate 2210 on the spacers 1616A.

Figure 26:
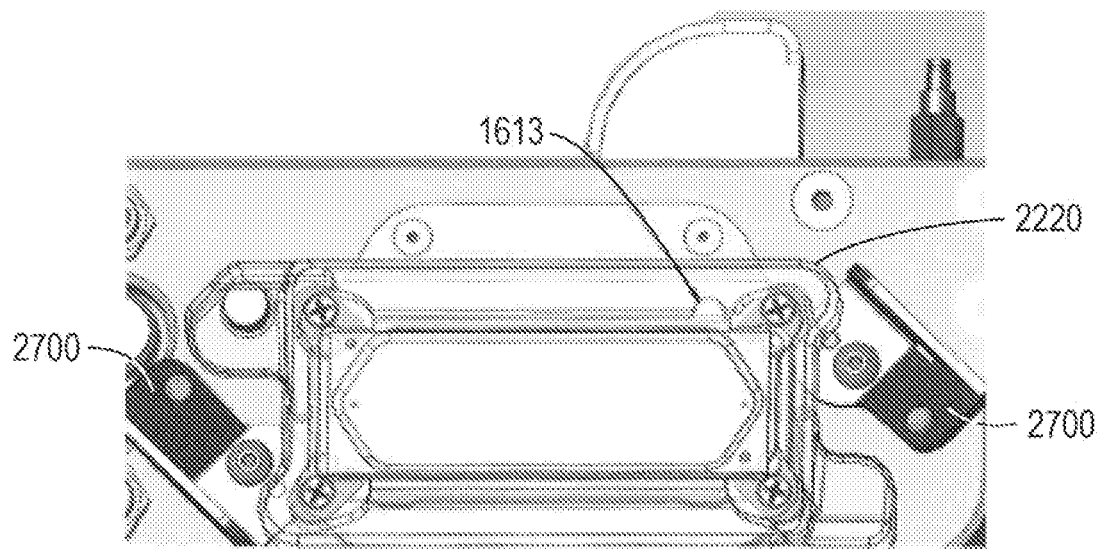
FIG. 26 is a top plan view of the substrate carrier of FIG. 22 loaded in a flow cell of FIG. 16 in an unclamped position with various elements made transparent to reveal other elements.

In various exemplary embodiments, lateral positioning of the substrate 2210 relative to the sample block 1612A may be facilitated by providing a registration member 1613A, shown in FIG. 26, on the sample block 1612A. The registration member 1613A may be a small projection that is configured to mate with a similarly shaped recess (e.g., notch) 2213 (shown in FIGS. 22 and 23) formed in the stepped profile region of the carrier frame 2212 that engages with the sample block 1612A.

To keep the carrier 2200 and substrate 2210 in the mounted position over the heater block 1612A a clamping mechanism may be used. It may be desirable to provide a clamping mechanism that does not extend over the surface of the carrier frame 2212 that faces the microscope when the flow cell is in a closed position (i.e., the surface of the carrier frame 2212 visible and facing upward in FIG. 24) to avoid contacting, and potentially damaging, the microscope objective lens, internal parts of the microscope stage, and/or other optics/detection mechanisms positioned for imaging the substrate 2210.

Figure 27:
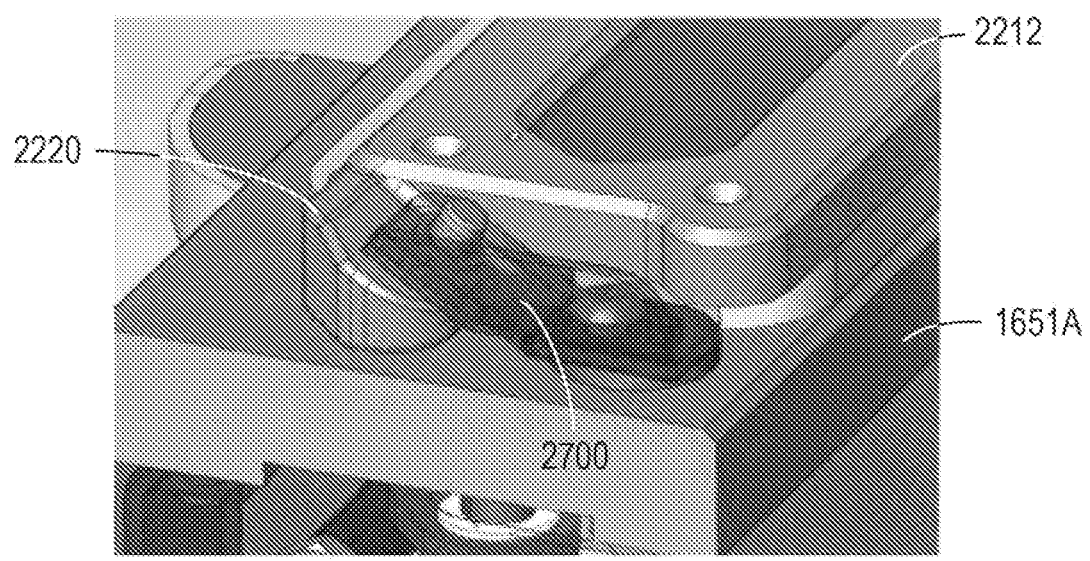
FIG. 27 is a partial close-up view of an exemplary embodiment of the substrate carrier of FIG. 22 loaded in a flow cell of FIG. 16 in a clamped position.
Figure 28:
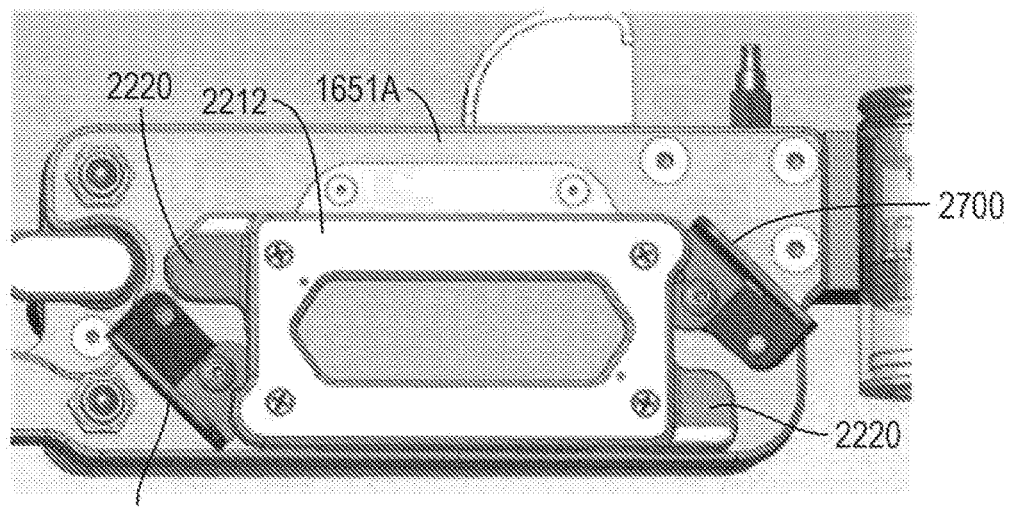
FIG. 28 is a top plan view of the substrate carrier of FIG. 22 loaded in a flow cell of FIG. 16 in an unclamped position.
Figure 29:
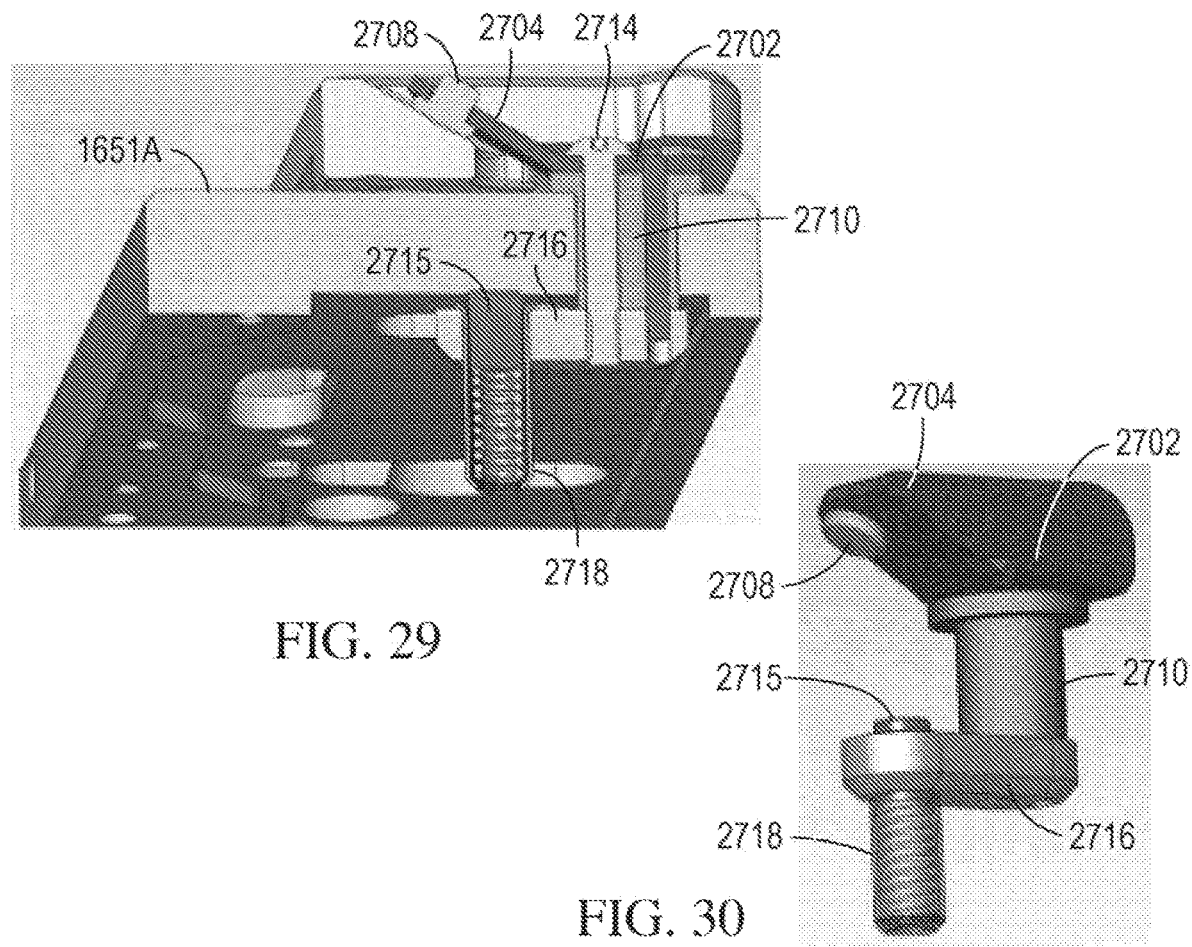
FIG. 29 is a sectioned side view showing the substrate carrier of FIG. 22 loaded in a flow cell of FIG. 16 in a clamped position.

With reference now to FIGS. 24 and 26-30, differing views of an exemplary embodiment of a clamping mechanism comprising rotatable clamping arms 2700 are illustrated. As will be explained in further detail below, the clamping arms 2700 engage with the clamping extensions 2220 provided on each end of the slide carrier frame 2212 at diagonally positioned corners of the frame to provide a clamping force on those extensions 2220 and retain the carrier 2200 and substrate 2210 held therein in position in the flow cell 1600A. As best shown in the views of FIGS. 27 and 29, the extensions 2220 may have a ramped surface with which the arms 2700 are configured to engage and provide a clamping force. The height of the ramped surface of the extensions 2220 may be such that, in the engaged position, the arms 2700 are not positioned beyond (e.g., above) the upper surface of the carrier frame 2212 (e.g., the surface of the carrier frame 2212 facing upward in FIGS. 27-29). FIGS. 26 and 28 illustrate the arms 2700 rotated in a disengaged (e.g., unclamped) position from the extensions 2220, and FIGS. 27 and 29 illustrate the arms 2700 rotated into an engaged (e.g., clamped) position with the extensions 2220.

Referring now to the partial sectioned side view of FIG. 29 and the isolation view of the clamping mechanism comprising clamping arm 2700, the clamping arm 2700 may comprise a base portion 2702 and an engagement portion 2704. The base portion 2702 may be mounted to one end of a rotatable shaft 2710 that extends through the thickness of the frame 1651A. The base portion 2702 may be secured to the end of the shaft 2710 that is on the side of the frame 1651A that supports the sample block (not shown). A securing member 2714 (e.g., a button head screw) extending along a length of the shaft 2710 may be used to secure the base portion 2702 to the shaft 2710. The entire clamping assembly depicted in FIG. 30 rotates together via rotation of the shaft 2710 relative to the frame 1651A. The engagement portion 2704 is disposed at an angle off of the base portion 2702 such that when rotated toward the carrier frame 2212, the engagement portion 2704 travels up the ramped surface of the extensions 2220 and exerts a substantially downward force on the extension 2220.

To provide a constant clamping force, a spring-loaded plunger 2715 in a housing tube 2718 may be used that engages the surface of the frame 1651A opposite to the surface that faces the arm 2700. The spring-loaded plunger 2715 is attached to the rotatable shaft 2710 via a holding plate 2716 that extends substantially perpendicularly to the shaft 2710. The securing member 2714 extends through the holding plate 2716 to secure the holding plate 2176 to the end of the shaft 2710 opposite to the end at which the base portion 2702 is mounted. The holding plate 2716 thus positions the spring-loaded plunger 2715 in substantial alignment with the engagement portion 2704 so that the plunger 2715 and engagement portion 2704 can exert a clamping force on the extension 2220 to clamp the slide carrier 2200 in place in the flow cell. The spring-loaded plungers 2715 cooperate with each of the clamping arms 2700 to exert a substantially constant clamping force on each end of the slide carrier 2200. The clamping mechanisms depicted in the exemplary embodiment of FIGS. 24 and 26-30, may provide a substantially uniform clamping force that is not user-dependent.

Figure 30:
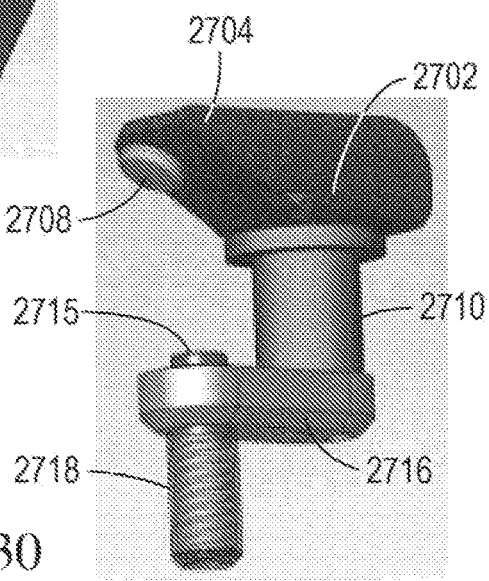
FIG. 30 is a perspective view of an exemplary embodiment of a clamping arm in accordance with the present teachings.

As shown in FIGS. 29 and 30, a foot 2708 may be associated with the engagement portion 2704 of the engagement arm 2700. The foot 2708 may be made of a plastic (e.g., a relatively hard plastic such as PEEK (polyetheretherketones)) or other suitable material configured to reduce friction and wear so that the foot 2708 may engage with the extension 2220 without scratching or otherwise damaging the extension 2220.

Figure 39:
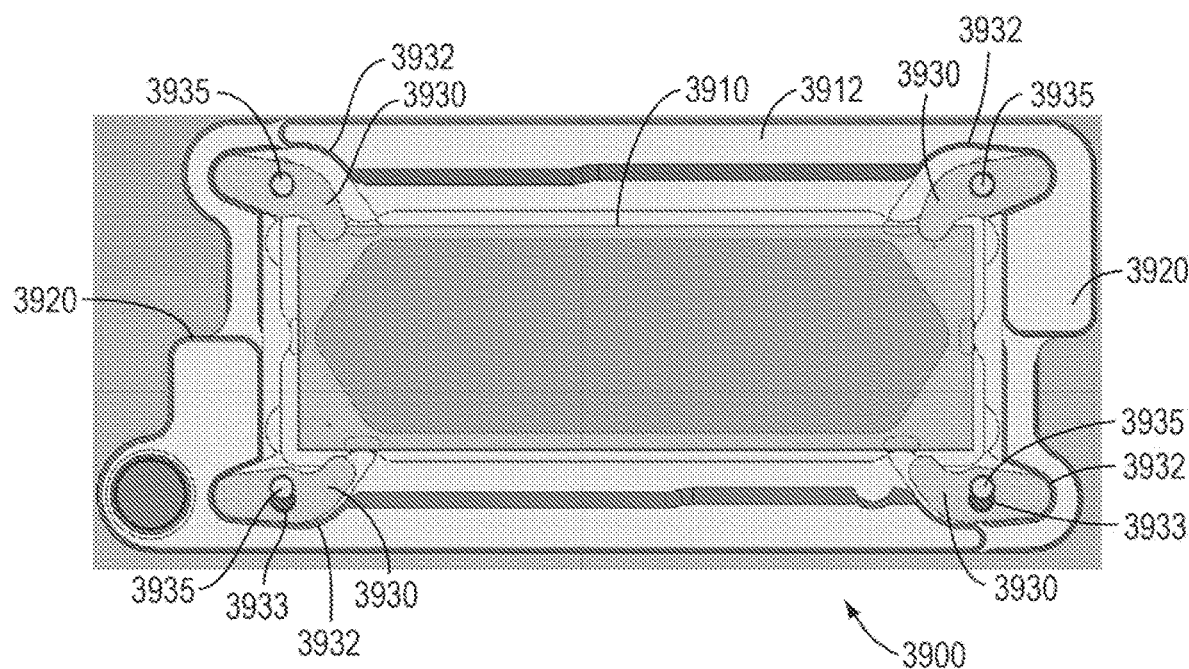
FIG. 39 is a plan view of another exemplary embodiment of a slide carrier in accordance with the present teachings.
Figure 40:
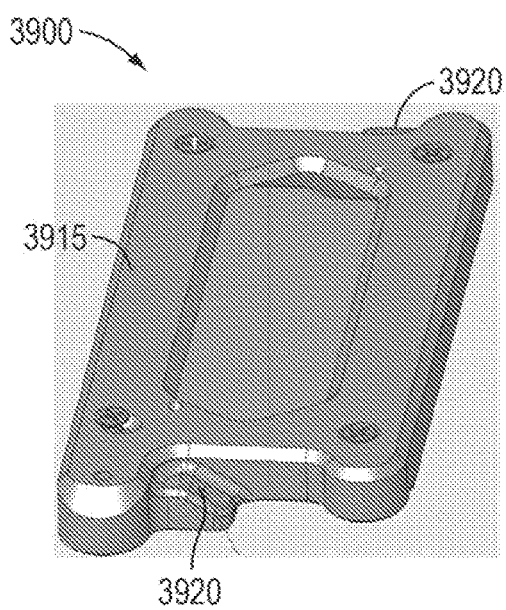
FIG. 40 is a top perspective view of the substrate carrier of FIG. 39.
Figure 41:
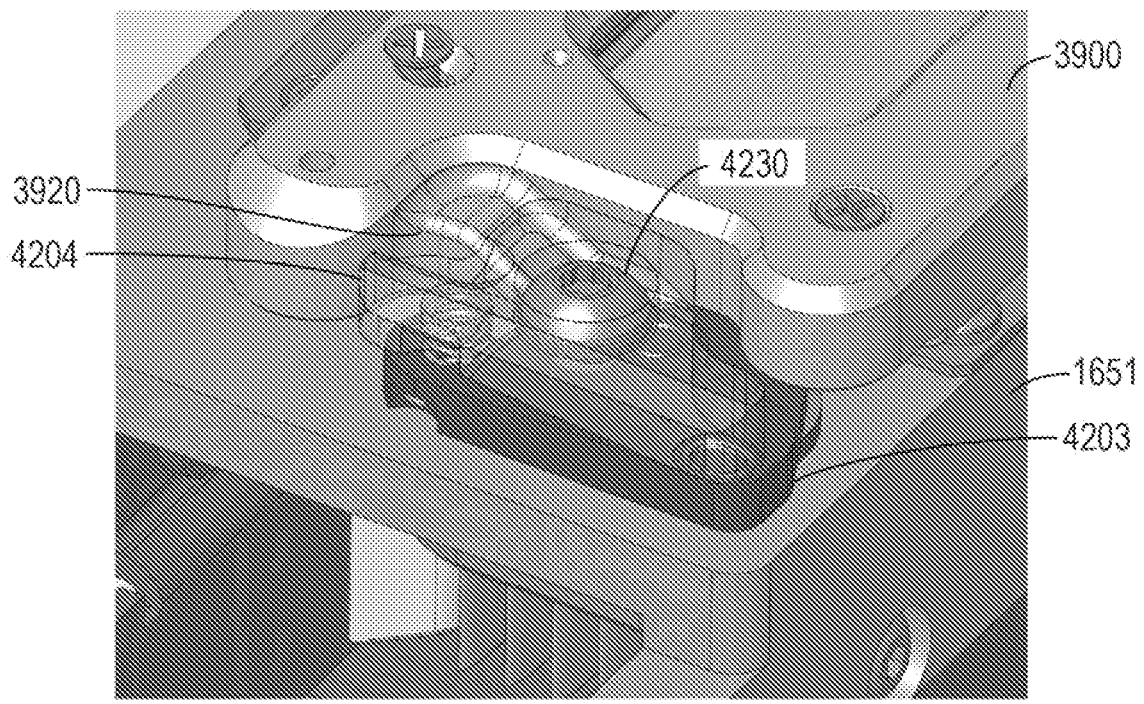
FIG. 41 is a partial perspective view of the substrate carrier of FIG. 39 in a clamped position in a flow cell according to the present teachings.

FIGS. 39-43 illustrate other exemplary embodiments of a slide carrier and a clamping arm in accordance with the present teachings. The slide carrier of the exemplary embodiment of FIGS. 39-41 is similar to that described above with reference to FIGS. 22-28 with modifications to the retaining fingers and clamping surfaces that engage with the clamping arm of the exemplary embodiment of FIGS. 41-43.

More specifically, the slide carrier 3900 in FIGS. 39-41 may comprise retaining fingers 3930 and corresponding recesses 3932 having a different configuration than those in the exemplary embodiment of the slide carrier 2200 described above. In the view of FIG. 39, the retaining fingers 3930 at the top of the slide carrier 2200 are in the clamped, engaged position to hold a substrate 3910 in place and the retaining fingers 3930 at the bottom of the slide carrier 2200 are in the unclamped, disengaged position. The retaining fingers 3930 of FIG. 39 are configured to pivot around a heel rather than a screw as in the exemplary embodiment of the slide carrier 2200. As shown in FIG. 39, the retaining fingers 3930 may include an opening 3933 configured to receive a screw 3935. The size of the opening 3933 is sufficient to allow the retaining fingers 3930 to pivot into and out of the engaged position, as shown by the top and bottom sets of retaining fingers 3930 respectively. To move the retaining fingers 3930, the screw 3935 may be loosened and the fingers 3930 moved. A countersink (not shown) may be used so that when the retaining fingers 3930 are moved into the engaged position and the screw 3935 is tightened, the retaining fingers 3930 are automatically moved to the correct, engaged position and the screw 3935 centers in the countersink.

Figure 42:
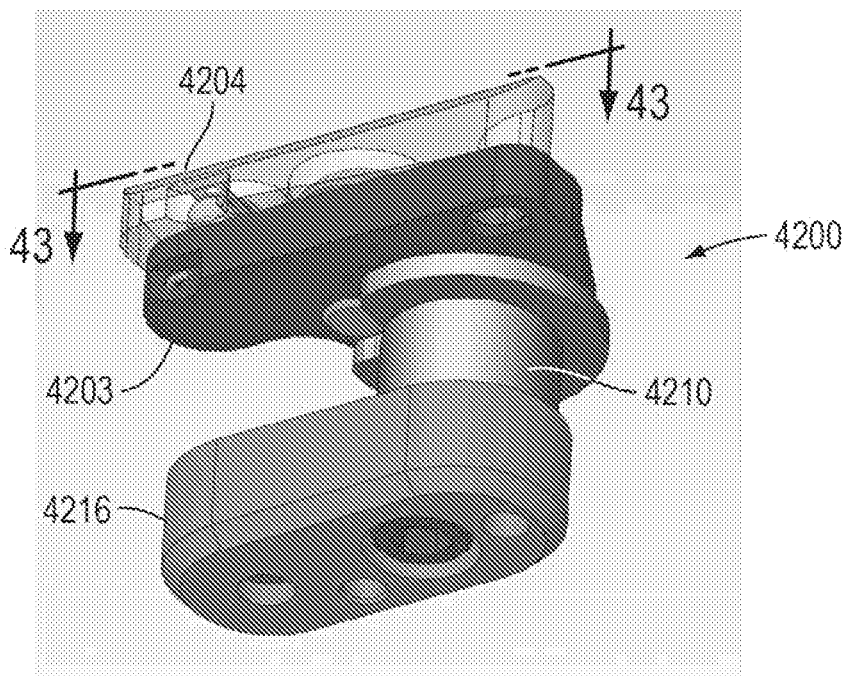
FIG. 42 is a perspective view of another exemplary embodiment of a clamping arm in accordance with the present teachings.
Figure 43:
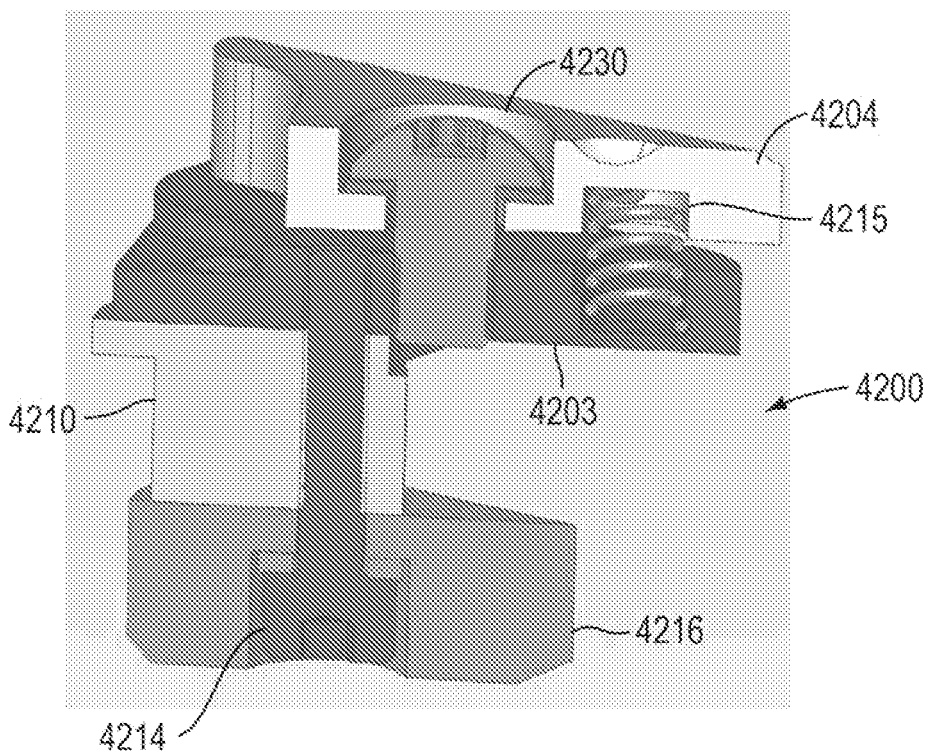
FIG. 43 is a cross-sectional view of the clamping arm of FIG. 42 taken through line 43-43.

With reference now to FIG. 40, the clamping extensions 3920 of the slide carrier 3900 also are modified from those of the exemplary embodiment of slide carrier 2200. In particular, the clamping extensions 3920 have been moved slightly inward closer to the center of the frame 3912 of the carrier 3920. FIGS. 41-43 depict an exemplary embodiment of a clamping arm 4200 that may be used to clamp the substrate carrier 3900 in place in the flow cell in a manner similar to that described above with reference to the exemplary embodiments of FIGS. 24-30. As with the exemplary embodiments of FIGS. 24-30, two such clamping arms 4200 may be used to respectively engage with each clamping extension 3920 on the slide carrier 3900.

The clamping arm 4200 has similar features as the clamping arm 2700 described above, including a rotatable shaft 4210 configured to pass through the frame 1651 of a flow cell. Those having ordinary skill in the art will understand that the clamping arm 4200 and substrate carrier 3900 may be used in conjunction with the flow cell embodiment of FIG. 15 and that the frame 1651 of the exemplary embodiment of FIG. 16 is used for exemplary purposes only. The clamping arm 4200 also may comprise a fixed base portion 4203 and a moveable engagement portion 4204 mounted together via a securement mechanism, such as a screw 4230, for example. The fixed base portion 4203 may in turn be mounted to one end of the rotatable shaft 4210 via a securement mechanism 4214, such as, for example, a screw, that extends through the base portion 4203, along the length of the rotatable shaft 4210, and a clamping plate 4216 disposed at the end of the shaft 4210 opposite the end at which the fixed base portion 4203 is secured. The entire clamping assembly depicted in FIGS. 42 and 43 rotates together via rotation of the shaft 4210 relative to the frame 1651.

The clamping plate 4216 and the fixed base portion 4203 thus contact opposite sides of the frame 1651. Rotation of the shaft 4210 causes the rotation of the clamping assembly 4200 and can move the engagement portion 4204 into and out of engagement with a clamping extension 3920 of the slide carrier 3900, as depicted in the outline portion of FIG. 41. A surface of the engagement portion 4204 configured to engage with the clamping extension 3920 of the slide carrier 3900 may be angled (e.g., ramped) such that when rotated toward the carrier frame 3912, the engagement portion 4204 travels up the ramped surface of the extension 3920 and exerts a substantially downward force on the extension 3920.

To provide a constant clamping force, in lieu of the spring-loaded plunger 2715 of the exemplary slide carrier 2200, the screw 4230 may be adjusted to move the engagement portion 4204 closer to the fixed portion 4203 to a position to provide a sufficient clamping force on the carrier 3900. A compression spring 4215 may be received in opposing recesses in the engagement portion 4204 and fixed base portion 4203 so that when the screw 4230 is loosened, the compression spring 4215 lifts the engagement portion 4204 up and away from the fixed base portion 4203 to permit rotation of the clamping arm 4200 out of engagement with the clamping extension 3920. The clamping arms 4200 for each clamping extension 3920 may be manually placed in the engaged and disengaged position to clamp or unclamp the substrate carrier 3900 in the flow cell.

Figure 31:
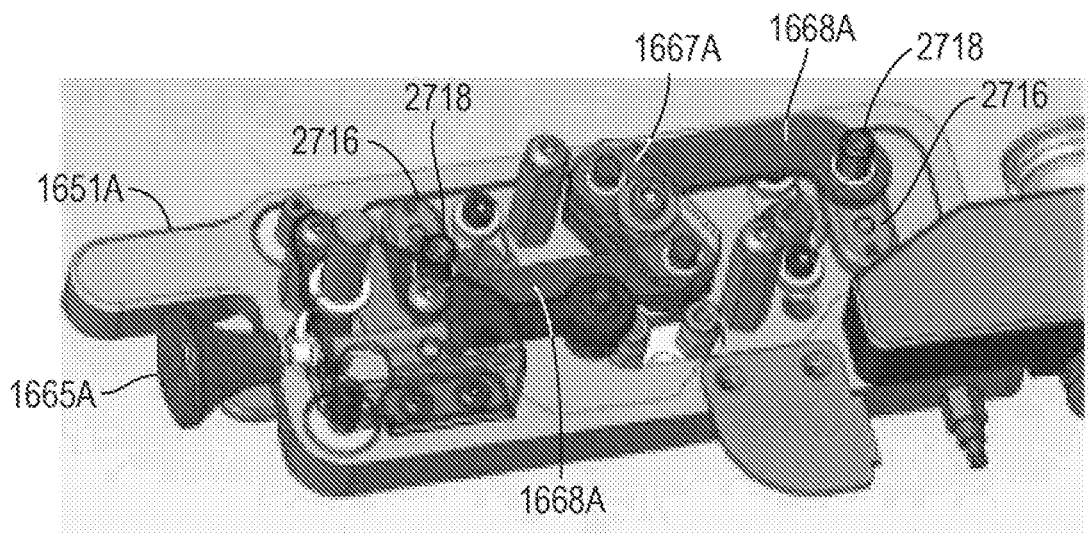
FIGS. 31 and 32 are top plan views showing an interior of the housing of a flow cell of the exemplary embodiment of FIG. 16 in accordance with the present teachings.
Figure 32:
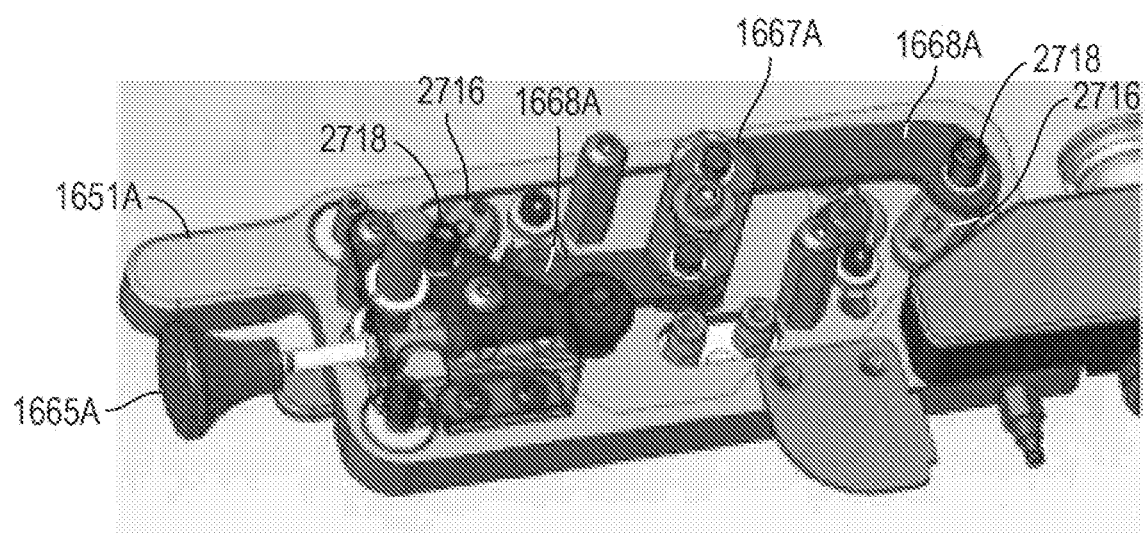

In various exemplary embodiments, the slide carrier may be clamped and unclamped into position in the flow cell manually. However, in some exemplary embodiments, to facilitate releasing and engaging the clamping arms 2700 to clamp and unclamp the carrier 2200, for example, in the flow cells 1600A and 1600B shown in FIG. 16, a push-pull knob 1665A and 1665B may be used. As shown in the view of the interior of the flow cell frame 1651A of FIGS. 31 and 32, the push-pull knob 1665A, may be coupled to a linkage system 1667A having a pair of dog-legged linkage arms 1668A. Each linkage arm 1668A is coupled to the housing tube 2718 of a respective clamping arm 2700 to rotate the clamping arms 2700 upon actuation of the linkage system 1667A. In FIG. 31, the push-pull knob 1165A and linkage system 1667A is shown with the push-pull knob 1165A pushed inward toward the frame 1651A, which places the clamping arms 2700 in an engaged (e.g., clamped) position (shown in FIGS. 24 and 27, for example). FIG. 32 shows the push-pull knob 1165A and linkage system 1667A with the push-pull knob 1165A pulled outward away from the frame 1651A, which places the clamping arms 2700 in a disengaged (e.g., unclamped) position (shown in FIGS. 26 and 28). The views of FIGS. 31 and 32 show the inner mechanical structure that is housed between the frame 1651A and flow cell housing cover 1653A (shown in FIG. 16). The linkage system 1667A and other mechanical structure shown in FIGS. 31 and 32 is thus on an opposite side of the frame 1651A as the side to which the sample block 1612 (and ultimately the substrate carrier 2200 and substrate 2210) is mounted.

In various exemplary embodiments, it may be desirable to provide a flow cell with a safety feature such that the flow cell is prevented from being closed if the substrate and/or substrate carrier are not clamped into an appropriate position within the flow cell for performing reactions and/or analysis (e.g., imaging). Likewise, it may be desirable to prevent the substrate and/or substrate carrier from accidentally being unclamped when the flow cell is in a closed position.

Figure 33:
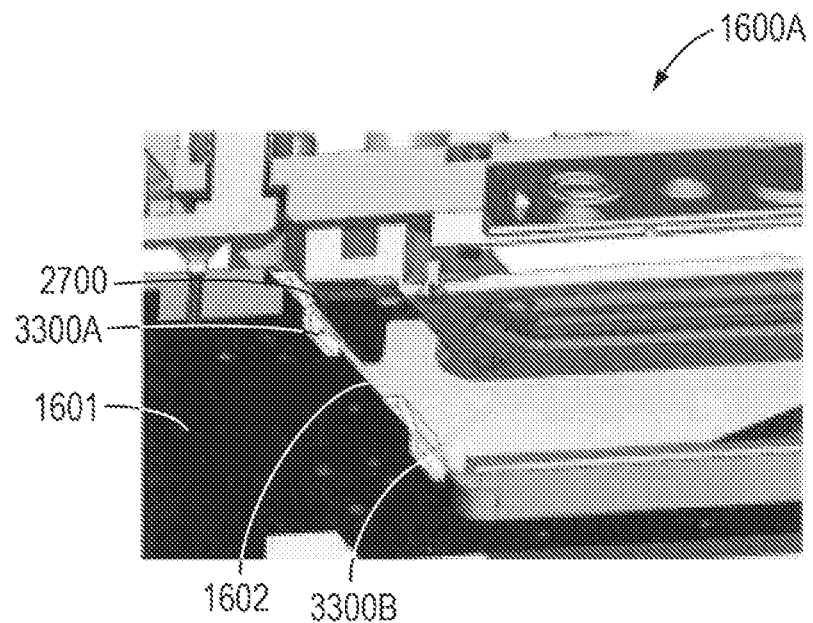
FIGS. 33 and 34 are perspective views of an exemplary embodiments of safety clips in accordance with the present teachings.
Figure 34:
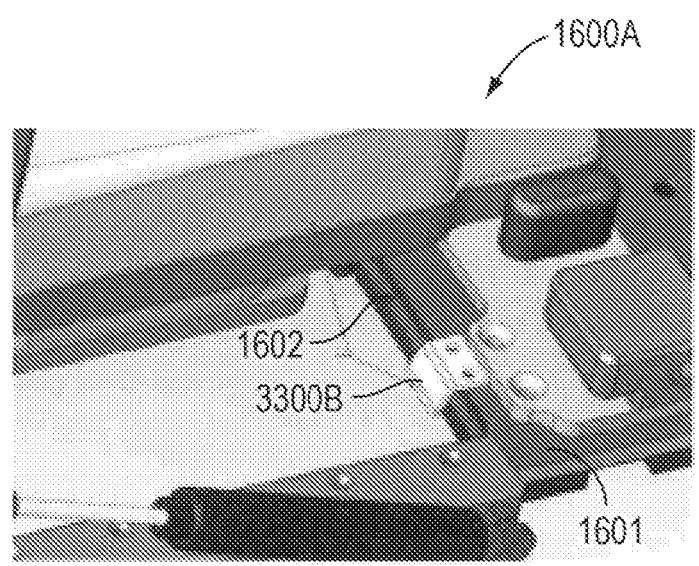

FIGS. 33 and 34 illustrate one exemplary embodiment that uses clips 3300A and 3300B positioned on the microscope stage 1601 as a safety feature for the flow cells 1600A and 1600B of the exemplary embodiment of FIG. 16. FIG. 33 is a partial, sectioned view of the exemplary embodiment of FIG. 16 shown with flow cell 1600B removed and viewing the instrument from the side of the microscope stage 1601 that faces the microscope and detection optics. FIG. 34 is a view of the instrument taken from the opposite side as FIG. 33. The clips 3300A and 3300B may be disposed on the upper part of the opening 1602 of the microscope stage 1601 so as to come into contact with clamping arms 2700 on the top of each flow cell 1600A and 1600B when the flow cells 1600A and 1600B are moved to the closed position if the clamping arms 2700 are in a disengaged position from the extensions 2220 on the substrate carriers 2200. As depicted in FIG. 33, the contact between the clip 3300A and the clamping arm 2700 prevents the flow cell 1600A from being completely closed when the clamping arm 2700 is not in a clamped position. If the clamping arms 2700 are in a clamped position to secure the substrate carrier 2200 in place within the flow cells 1600A and 1600B and the flow cells 1600A and 1600B are in the closed position, the clips 3300A and 3300B prevent the clamping arms 2700 from being able to rotate out of engagement with the extensions 2220 on carrier 2200.

Figure 35:
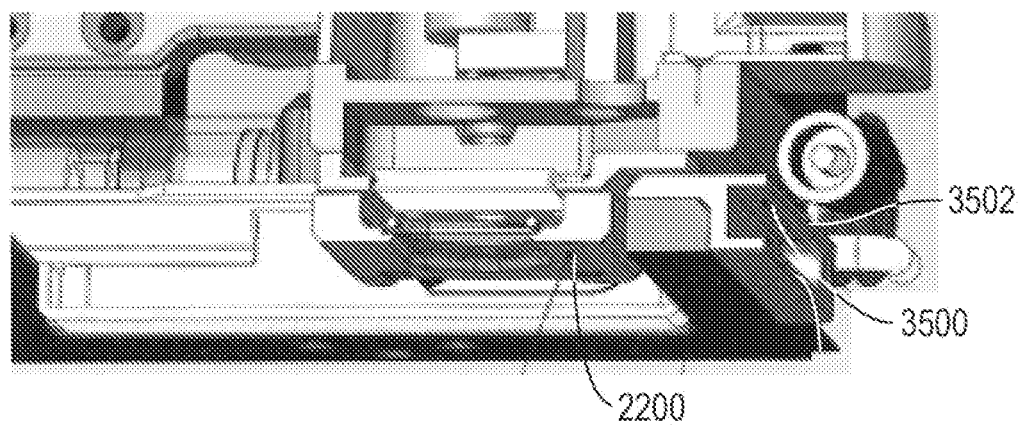
FIG. 35 is a partial sectioned view showing an exemplary embodiment of a heat sink for mounting to a microscope stage holding a flow cell in accordance with the present teachings.

In various exemplary embodiments in accordance with the present teachings, when a flow cell is in position to perform reactions and/or analysis within the flow cell chamber, heat may radiate from the flow cell chamber (e.g., during a relatively high temperature reaction (thermocycling) stage). In some cases, depending, for example, on the proximity of the flow cell reaction chamber to the microscope stage and/or the structural configuration of the microscope stage, it may be desirable to remove such radiated heat from overheating the microscope stage. By way of example, in various exemplary embodiments the microscope stage may have a relatively thin side that defines the opening in which the flow cells are mounted. One solution that may be employed is to add a brace that also serves as a heat sink to the microscope stage frame. Such a brace may supply additional support to the microscope stage proximate the opening and also may serve as a heat sink to remove heat from the microscope stage. An exemplary embodiment of a brace 3500 attached to a side portion of the microscope stage 1601 located proximate the substrate carrier 2200 of a flow cell in the exemplary embodiment of FIG. 16 is depicted in FIG. 35. FIG. 35 is a cross-sectional view of the flow cell of FIG. 16 taken in plane perpendicular to the drawing sheet of FIG. 16 at about a mid-section of the flow cell 1600A. The brace 3500 may be made of, for example, aluminum or other material offering good thermal conductivity, sufficient stiffness and light weight. The brace 3500 may include one or more fins 3502 or similar structures configured to conduct heat away from the microscope stage 1601 when the brace 3500 is mounted thereto.

As mentioned above, the various flow cells described herein in accordance with exemplary embodiments of the present teachings may include various thermal components to provide thermal cycling and/or other temperature regulation of the flow cell. U.S. application Ser. No. 11/757,286, incorporated by reference herein, provides details regarding various thermal systems and components that may be used in conjunction with the exemplary embodiments of the present teachings. The present disclosure also includes some exemplary thermal arrangements, including cooling systems, configured to cool the flow cell reaction chambers of the exemplary embodiments. For example, a cooling system comprising a remotely located cooling fan configured to blow air through ducts and onto a heat sink associated with the flow cell has been described. In other exemplary embodiments, it may be desirable to use liquid cooling of the flow cells and remove the heat sink, ducts, and fan. Such liquid cooling may be employed by using a liquid heat exchanger such as that depicted in the exemplary embodiment of FIG. 36

Figure 36:
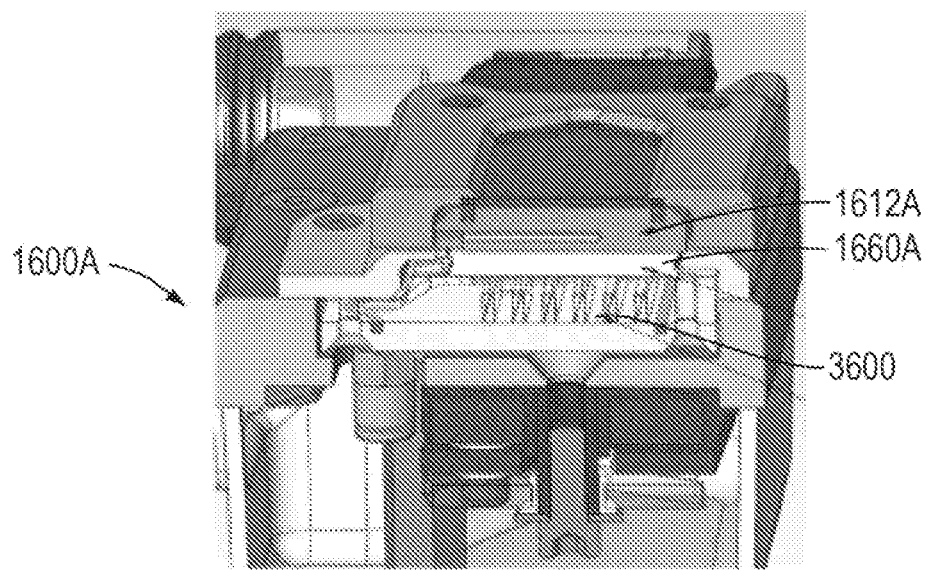
FIG. 36 is a partial sectioned view of an exemplary embodiment of a cooling element for use in cooling a flow cell in accordance with the present teachings.

FIG. 36 is a partial cross-sectional view that shows an exemplary embodiment of a liquid heat exchanger 3600 used in conjunction with the flow cell 1600A of FIG. 16. Those having skill in the art would understand, however, that the liquid heat exchanger 3600 may be used to provide cooling of the reaction chambers of a variety of flow cell configurations, including any of those shown and described herein, with obvious modifications to the flow cell structure to accommodate such a liquid heat exchanger. In various exemplary embodiments, and as shown in FIG. 36, the liquid heat exchanger 3600 may be positioned underneath a Peltier device 1660A used to heat and/or cool the sample block 1612A. The liquid heat exchanger 3600 may include a plurality of flow channels 3602 configured to flow cooling liquids, such as, for example, water, alcohol, a refrigerant, and/or other suitable cooling liquids, therein. The cooling liquid circulating through the liquid heat exchanger 3600 may absorb heat from the reaction chamber formed between the substrate 2210 and the sample block 1612A to help maintain the reaction chamber at a desired temperature. Mounted in a remote location from the flow cell may be another heat exchanger, for example, with a fan and heat sink, configured to remove heat absorbed by the liquid of the liquid heat exchanger 3600. A pump or other suitable flow mechanism may be used to circulate the liquid into and out of the heat exchanger 3600 via tube ports (not shown).

A liquid heat exchanger configured like that of the exemplary embodiment in FIG. 36 may be relatively small compared to other cooling components used to remove heat from the reaction chamber, and therefore may be desirable in situations where space is a consideration. Moreover, the liquid heat exchanger may be relatively light and thus decrease the weight of the flow cell, facilitating opening, closing, and otherwise manipulating the flow cell.

Figure 37:
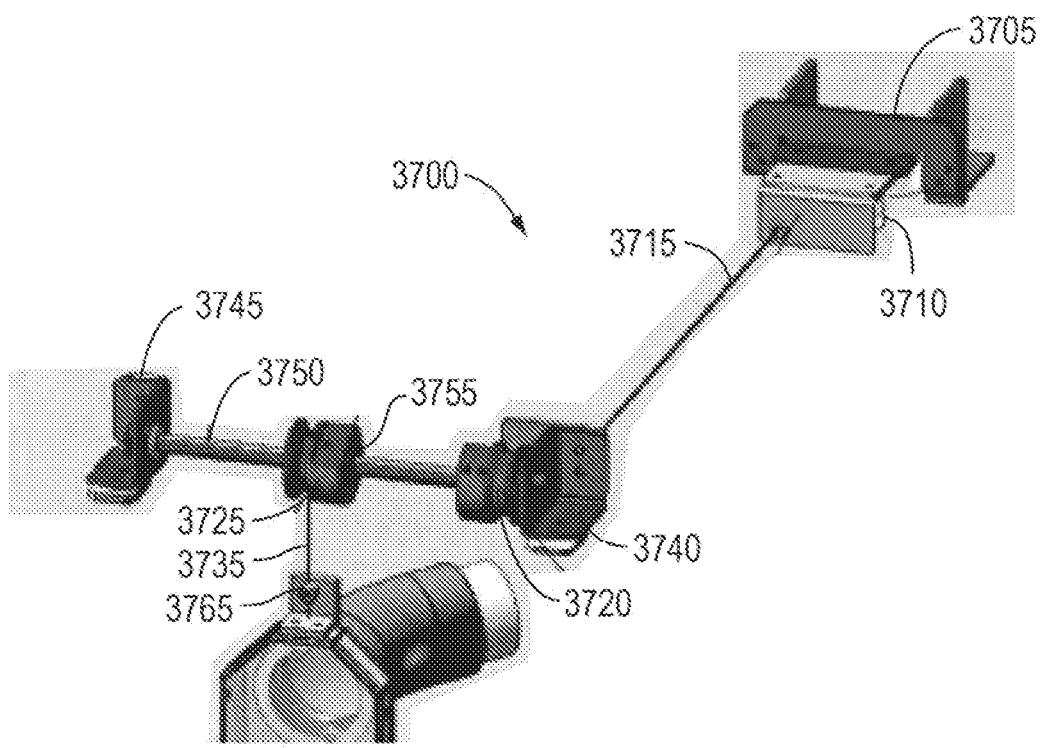
FIGS. 37 and 38 are perspective views of an exemplary embodiment of a counterbalance system in accordance with the present teachings.
Figure 38:
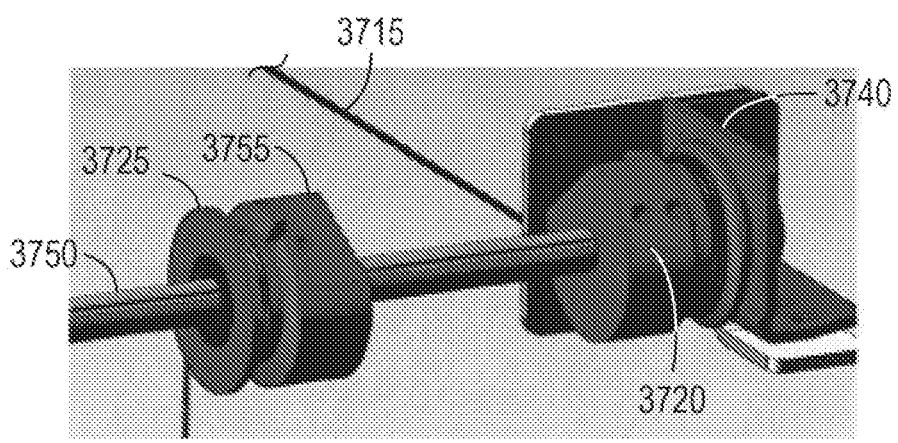

As discussed above, in various exemplary embodiments, the flow cells in accordance with the present teachings may be mounted to a vertically positioned (e.g., positioned with its largest surfaces substantially perpendicularly to the ground) microscope stage. In some embodiments, the microscope stage may be one designed to operate in a horizontal position (e.g., having its largest surfaces substantially parallel to the ground). In some cases, such stages may tend to coast downward due to the weight of the flow cell when the power is not being used to move the stage. FIGS. 37 and 38 illustrate an exemplary embodiment of a counterbalance system that may be used to hinder movement of the stage downward due to the weight of the flow cell.

In the exemplary embodiment of FIGS. 37 and 38, a cable and pulley system 3700 is used to counterbalance the weight of the flow cell. In the exemplary embodiment shown, the system 3700 may include a mounting bracket 3705 configured to mount onto a fixed surface, such as, for example, a frame associated with the biological analysis instrumentation utilizing the microscope stage and flow cell. The mounting bracket 3705 may have a spring loaded cable reel 3710 coupled thereto by way of a plate supporting the reel. A dead weight may be used in lieu of a spring-loaded cable reel, with the ultimate function being to provide a tension in a cable 3715 attached thereto sufficient to counteract the weight of the flow cell. The plate may define a throughhole configured to permit passage of the cable 3715 extending from the reel 3710. The reel 3710 in various exemplary embodiments may be a part commercially available from Ametek Electric that includes a pair of clock springs configured to provide a roughly constant pulling force on the cable 3715. The cable 3715 may be wound around a drive pulley 3720 to in turn apply a constant torque on the pulley 3720. The drive pulley 3720 may be mounted to another mounting bracket 3740 configured to be mounted to a fixed surface relative to the biological analysis instrument in closer proximity to the microscope stage than the mounting bracket 3705. A spline shaft 3750 is fixed at one end to the drive pulley 3720 and at an opposite end to a shaft mounting bracket 3745, and is configured to rotate in response to rotation of the drive pulley 3720.

A driven pulley 3725 also may be coupled to the spline shaft 3750 between the drive pulley 3720 and the mounting bracket 3745. A second cable 3735 may extend from the driven pulley 3725 and have a clip or other coupling mechanism 3765 at an end thereof that is configured to mount in a fixed manner relative to the microscope stage (not shown). In the exemplary embodiment of FIG. 37, the coupling mechanism 3765 mounts to an upper portion of a main duct configured to flow cooling air to the one or more flow cells on the microscope stage. Those ordinarily skilled in the art would understand, however, that the coupling mechanism 3765 may mount to various other portions of the flow cell or microscope stage (or peripheral elements associated therewith) as long as the cable 3735 provides a force acting an upward direction on the microscope stage.

The driven pulley 3725 may be coupled to the spline shaft 3750 via a spline bearing 3755. In this manner, the driven pulley 3725 may be configured to rotate with the shaft 3750, but also may slide along a length of the spline shaft 3750. Permitting the driven pulley 3725 to slide along the length of the spline shaft 3750 allows the cable 3735 to track the sideways motion of the microscope stage since the stage translates in all three dimensions (e.g., side-to-side and up and down).

By using the system 3700, tension in the cable 3715 can be transmitted ultimately to the cable 3735 via the pulleys 3720 and 3725 to create a lifting force on the microscope stage to counterbalance the downward force on the stage caused by the weight of the flow cell. The sizes of the drive pulley 3720 and driven pulley 3725 can be selected as desired to fine tune the amount of counterbalancing force that is needed to prevent the microscope stage from coasting downward.

Although various exemplary embodiments shown and described herein describe the use of a substrate that supports a microarray of nucleic acid templates as the sample holder introduced into the flow cell reaction chambers, it is considered within the scope of the present teachings that the flow cell reaction chambers set forth herein are configured to hold one or more biological samples for analysis that may be provided in a variety of differing types of sample holders, which may be supported by sample blocks of the flow cells. By way of example, the flow cells may be configured to receive sample holders including, for example, recesses and/or wells in a microtiter plate, capillaries, tubes/microtubes, microfluidic devices/chambers, throughhole plates, sample trays, and other types of sample holders. Sample holders may also comprise various materials having locations for holding or retaining samples such as on a microcard or sample substrate including for example glass, plastic, polymer, metal, or combinations thereof. A substrate may be configured in numerous manners, for example, as a generally planar substrate, such as a microscope slide or planar array, configured to hold an array of templates or other samples, and/or other conventional sample holders used for biological analysis processes in the form of microtiter plates, capillaries, and/or other sample holders configured to be filled with one or more biological samples and which may be supported by the sample blocks in the flow cells. Further, it also is envisioned that one or more biological samples may be introduced directly into the reaction chamber of the flow cell without being held by a substrate, microtiter plate, capillary and/or other sample holder. In one exemplary embodiment of an arrangement wherein the sample is introduced into the reaction chamber without a sample holder, the sample block may also be removed and the reaction chamber itself formed by the flow cell structure being heated and cooled.

Throughout the specification, reference is made to biological sample and/or biological samples. It should be understood that the biological analysis instruments in accordance with the present teachings are configured to perform processes on multiple amounts of sample simultaneously. Further, differing types of sample may be processed simultaneously. Thus, when reference is made to a biological sample being provided in a reaction chamber, it should be understood that the term may refer to either a single type of sample in a single amount, multiple amounts of a single type of sample, and/or multiple amounts of differing types of sample. The term also may be used to refer to a bulk amount of substance placed in the reaction chamber. Further, in its broadest sense, the term sample can include the various reagents, etc. that are introduced to the chamber to perform an analysis or other process therein.

In various exemplary embodiments described herein, the flow cells may be configured to flow reagents into the reaction chambers to react with microarrays of template nucleic acid in order to perform sequencing of the template nucleic acid residing on the substrate. Examples of various substrates holding nucleic acid templates and methods of making such substrates can be found in WO 2006/084132, which published Aug. 10, 2006, entitled "REAGENTS, METHODS, AND LIBRARIES FOR BEAD-BASED SEQUENCING," and is incorporated herein by reference in its entirety.

The term "nucleic acid" can be used interchangeably with "polynucleotide" or "oligonucleotide" and can include single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, H+, NH4+, trialkylammonium, Mg2+, Na+ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleosides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5'terminus, 3'terminus, a nucleobase, an internucleotide linkage, a sugar, amino, sulfide, hydroxyl, or carboxyl. See, for example, U.S. Pat. No. 6,316,610 B2, which issued Nov. 13, 2001 and is entitled "LABELLED OLIGONUCLEOTIDES SYNTHESIZED ON SOLID SUPPORTS," which is incorporated herein by reference. Similarly, other modifications can be made at the indicated sites as deemed appropriate.

The term "reagent" should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a DNA that hybridizes to another DNA. The term "reagent" is used synonymous with the term "reaction component."

Although in various exemplary embodiments, the flow cells described herein were described with reference to performing sequencing by synthesis on microarrayed substrates, those having ordinary skill in the art would recognize that the flow cells in accordance with various embodiments of the present teachings may be configured to perform various biological analyses and reaction processes therein, including, but not limited to, for example, nucleic acid analysis methods, such as, for example, sequencing and/or hybridization assays, protein analysis methods, binding assays, screening assays, and/or synthesis, for example, to generate combinatorial libraries, and/or other biological processes and analysis methods. It should also be understood, that any number of flow cells may be provided, with the dual embodiments shown and described herein being exemplary and nonlimiting.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," and any singular use of any word, include plural referents unless expressly and unequivocally limited to one referent. Thus, for example, reference to "a biological sample" includes two or more different biological samples. As used herein, the term "include" and its grammatical variants are intended to be non-limiting, such that recitation of items in a list is not to the exclusion of other like items that can be substituted or added to the listed items.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for performing biological sample reactions, the device comprising:
   a microscope translation stage capable of translation in a dimension of a plane;
   a main duct disposed adjacent the microscope translation stage; and
   a plurality of flow cells each configured to be separately removably mounted relative to the microscope translation stage, each flow cell of the plurality of flow cells including a cover defining an optically transparent region, a heater block disposed over the cover on an opposite side of the cover relative to the microscope translation stage, a heat sink disposed over the heater block, and a duct disposed over the heat sink and to circulate air to the heat sink, each of the plurality of flow cells configured to receive a sample holder containing at least one biological sample between the cover and the heater block in alignment with the optically transparent region, the duct having an opening to engage the main duct when the each flow cell is mounted to the microscope translation stage;
   wherein each of the plurality of flow cells is further configured to receive fluid when mounted relative to the microscope translation stage to enable a biochemical reaction of the at least one biological sample;
   wherein each of the plurality of flow cells are configured to permit a biochemical reaction of sample to occur in at least one of the plurality of plurality of flow cells with a substrate comprising an array of microparticles comprising nucleic acid templates.

2. The device of claim 1, further comprising a frame mounted to the microscope translation stage, wherein the plurality of flow cells are configured to be removably mounted to the frame.

3. The device of claim 1, wherein the heater block includes a thermal element configured to control a temperature of the at least one biological sample received by the plurality of flow cells.

4. The device of claim 1, wherein the heat sink comprises at least one forced air cooling component.

5. The device of claim 3, wherein the thermal element comprises at least one thermoelectric component.

6. The device of claim 4, wherein the forced air cooling component includes a heat sink pin.

7. The device of claim 1, wherein each of the plurality of flow cells is configured to be mounted relative to a benchtop loading fixture to receive the sample holder.

8. The device of claim 1, wherein the sample holder is a substrate comprising an array of microparticles comprising nucleic acids.

9. The device of claim 1, wherein the device is configured to perform nucleic acid sequencing.

10. The device of claim 1, wherein each of the sample holders received by the plurality of flow cells is configured to be imaged when the plurality of flow cells are mounted relative to the microscope translation stage.

11. A method for performing biological analysis, the method comprising:
respectively providing a plurality of flow cells each with a sample holder containing at least one sample for biological analysis, each flow cell of the plurality of flow cells separately mountable to a microscope translation stage and including a cover defining an optically transparent region, a heater block disposed over the cover on an opposite side of the cover relative to the microscope translation stage, a heat sink disposed over the heater block, and a duct disposed over the heat sink and to circulate air to the heat sink, each of the plurality of flow cells configured to receive the sample holder between the cover and the heater block in alignment with the optically transparent region, the duct having an opening to engage a main duct when the each flow cell is mounted to the microscope translation stage, the main duct disposed adjacent the microscope translation stage;
mounting each of the plurality of flow cells relative to the microscope translation stage capable of translation in a dimension of a plane; and
performing a biochemical reaction in each of the plurality of flow cells while the plurality of flow cells are mounted relative to the microscope translation stage,
wherein the respectively providing the plurality of flow cells with a sample holder occurs prior to the mounting of the plurality of flow cells relative to the microscope translation stage,
wherein each of the plurality of flow cells are configured to permit a biochemical reaction of sample to occur in at least one of the plurality of plurality of flow cells with a substrate comprising an array of microparticles comprising nucleic acid templates.

12. The method of claim 11, wherein the respectively providing the plurality of flow cells with a sample holder occurs while the plurality of flow cells are mounted relative to a benchtop loading fixture.

13. The method of claim 11, wherein the respectively providing the plurality of flow cells with a sample holder comprises respectively providing each of the flow cells while analysis of a reacted sample occurs in at least one other of the plurality of flow cells.

14. The method of claim 11, further comprising imaging the sample holder received by the plurality of flow cells.

15. The method of claim 11, wherein the performing biochemical reaction comprises sequencing nucleic acids.

16. The method of claim 11, further comprising performing a biochemical reaction in at least one of the plurality of flow cells while analyzing a reaction of the sample that has occurred in at least one other of the plurality of flow cells while the plurality of flow cells are mounted relative to the microscope translation stage.

17. The method of claim 11, further comprising controlling a temperature of the at least one sample.

18. The method of claim 17, wherein controlling the temperature comprises forcing air proximate the plurality of flow cells via the duct.

19. The method of claim 17, wherein the heat block includes a thermoelectric component, wherein controlling the temperature comprises controlling the temperature via a thermoelectric component.

* * * * *

UNITED STATES PATENT AND TRADEMARK OFFICE
CERTIFICATE OF CORRECTION

PATENT NO. : 11,371,093 B2
APPLICATION NO. : 16/246990
DATED : June 28, 2022
INVENTOR(S) : Dennis Lehto and Steven Boege It is certified that error appears in the above-identified patent and that said Letters Patent is hereby corrected as shown below:

In the Claims

In Column 36, Claim 1, Line 57, delete "plurality of plurality of" and insert -- plurality of --, therefor.

In Column 37, Claim 11, Line 28, delete "the cover on an opposite side of the cover relative to the" and insert the same at Line 27 after "over" as a continuation paragraph.

In Column 38, Claim 11, Line 10, delete "plurality of plurality of" and insert -- plurality of --, therefor.

In Column 38, Claim 18, Line 34, delete "proximate the" and insert -- proximate to the --, therefor.

Signed and Sealed this
Twenty-ninth Day of November, 2022

Katherine Kelly Vidal
*Director of the United States Patent and Trademark Office*